(12) United States Patent
Chen et al.

(10) Patent No.: US 10,159,674 B2
(45) Date of Patent: *Dec. 25, 2018

(54) BENZATHINE ANALOGS

(71) Applicants: University of Pittsburgh—Of the Commonwealth System of Higher Education, Pittsburgh, PA (US); The United States of America as represented by the Department of Veterans Affairs, Washington, DC (US)

(72) Inventors: Beibei Chen, Wexford, PA (US); Rama K. Mallampalli, Sewickley, PA (US)

(73) Assignees: University of Pittsburgh—Of the Commonwealth System of Higher Education, Pittsburgh, PA (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/138,137

(22) Filed: Apr. 25, 2016

(65) Prior Publication Data

US 2016/0237040 A1    Aug. 18, 2016

Related U.S. Application Data

(63) Continuation of application No. 14/406,189, filed as application No. PCT/US2013/030995 on Mar. 13, 2013, now Pat. No. 9,359,284.
(Continued)

(51) Int. Cl.
| | |
|---|---|
| *C07C 211/53* | (2006.01) |
| *C07D 207/06* | (2006.01) |
| *A61K 31/137* | (2006.01) |
| *A61K 31/132* | (2006.01) |
| *A61K 31/402* | (2006.01) |
| *A61K 31/506* | (2006.01) |
(Continued)

(52) U.S. Cl.
CPC .......... *A61K 31/506* (2013.01); *A61K 31/137* (2013.01); *A61K 31/341* (2013.01); *A61K 31/381* (2013.01); *A61K 31/402* (2013.01); *A61K 31/4155* (2013.01); *A61K 31/4178* (2013.01); *A61K 31/427* (2013.01); *A61K 31/435* (2013.01); *A61K 31/444* (2013.01); *A61K 31/4418* (2013.01); *A61K 31/5375* (2013.01); *C07C 211/01* (2013.01); *C07C 211/53* (2013.01); *C07C 229/38* (2013.01); *C07D 207/06* (2013.01); *C07D 211/14* (2013.01); *C07D 213/06* (2013.01); *C07D 213/36* (2013.01); *C07D 213/38* (2013.01); *C07D 231/12* (2013.01); *C07D 233/61* (2013.01); *C07D 233/64* (2013.01); *C07D 239/26* (2013.01); *C07D 265/30* (2013.01); *C07D 277/28* (2013.01); *C07D 295/135* (2013.01); *C07D 401/12* (2013.01); *C07D 403/12* (2013.01)

(58) Field of Classification Search
CPC ... C07C 211/53; C07D 207/06; A61K 31/137; A61K 31/132; A61K 31/402
USPC .................. 564/462, 337, 384; 514/650, 655
See application file for complete search history.

(56) References Cited

U.S. PATENT DOCUMENTS

| | | | |
|---|---|---|---|
| 4,010,282 | A | 3/1977 | Binning et al. |
| 2003/0013772 | A1 | 1/2003 | Murphy et al. |
(Continued)

FOREIGN PATENT DOCUMENTS

| | | |
|---|---|---|
| EP | 1127883 | 6/2005 |
| JP | 20011278869 | 10/2001 |
(Continued)

OTHER PUBLICATIONS

STN Registry CAS RN 1312706-27-6. Entered STN: Jul. 14, 2011. (Year: 2011).*
(Continued)

*Primary Examiner* — Matthew P Coughlin
*Assistant Examiner* — Sagar Patel
(74) *Attorney, Agent, or Firm* — Klarquist Sparkman, LLP

(57) ABSTRACT

A compound, or a pharmaceutically acceptable salt or ester thereof, having a structure of:

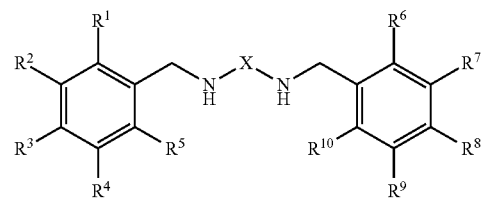

wherein X is a divalent linking moiety; and
$R^1$-$R^{10}$ are each individually H, optionally-substituted alkyl, optionally-substituted alkoxy, optionally-substituted aryl, optionally-substituted cycloalkyl, optionally-substituted heterocyclic, halogen, amino, or hydroxy, provided that at least one of $R^3$ or $R^8$ is an optionally-substituted alkyl, a substituted alkoxy, optionally-substituted aryl, optionally-substituted cycloalkyl, optionally-substituted heterocyclic, or halogen.

11 Claims, 72 Drawing Sheets
Specification includes a Sequence Listing.

Related U.S. Application Data

(60) Provisional application No. 61/657,423, filed on Jun. 8, 2012.

(51) Int. Cl.

| | | |
|---|---|---|
| A61K 31/341 | (2006.01) | |
| A61K 31/381 | (2006.01) | |
| A61K 31/4155 | (2006.01) | |
| A61K 31/427 | (2006.01) | |
| A61K 31/4418 | (2006.01) | |
| A61K 31/5375 | (2006.01) | |
| C07D 239/26 | (2006.01) | |
| C07D 213/36 | (2006.01) | |
| C07D 231/12 | (2006.01) | |
| C07D 233/61 | (2006.01) | |
| C07C 211/01 | (2006.01) | |
| C07C 229/38 | (2006.01) | |
| C07D 211/14 | (2006.01) | |
| C07D 213/06 | (2006.01) | |
| C07D 213/38 | (2006.01) | |
| C07D 265/30 | (2006.01) | |
| C07D 277/28 | (2006.01) | |
| A61K 31/4178 | (2006.01) | |
| A61K 31/435 | (2006.01) | |
| A61K 31/444 | (2006.01) | |
| C07D 233/64 | (2006.01) | |
| C07D 403/12 | (2006.01) | |
| C07D 401/12 | (2006.01) | |
| C07D 295/135 | (2006.01) | |

(56) References Cited

U.S. PATENT DOCUMENTS

| | | | |
|---|---|---|---|
| 2006/0148904 A1 | 7/2006 | Protopopova et al. | |
| 2016/0235747 A1* | 8/2016 | Chen | C07D 233/64 |
| 2016/0310447 A1* | 10/2016 | Chen | A61K 45/06 |

FOREIGN PATENT DOCUMENTS

| | | |
|---|---|---|
| WO | WO 1999/024395 | 5/1999 |
| WO | WO 2001/072685 | 10/2001 |
| WO | WO 03/096989 | 11/2003 |
| WO | WO 2008/027932 | 3/2008 |
| WO | WO 2008/142623 | 11/2008 |

OTHER PUBLICATIONS

Shen, W., H. Zhang, H. Zhang and J. Gao "Novel chiral tetraaza ligands: synthesis and application in assymmetric transfer hydrogenation of ketones" Tetrahyd. Asym. (2007), 18: pp. 729-733. (Year: 2007).*

Albano et al., "Novel chiral diamino-oligothiophenes as valuable ligands in Pd-catalyzed allylic alkylations. On the primary role of secondary interactions in asymmetric catalysis," *Advanced Synthesis & Catalysis*, 347: 1507-1512, Oct. 19, 2005.

Caterina M.C., et al., "Imidazolines are new anti-Trypanosoma cruzi agents: Biological evaluation and structure-activity relationships," *Bioorganic & Medicinal Chemistry*, 16: 2226-2234, 2008.

Chen et al., "A combinatorial F box protein directed pathway control TRAF adaptor stability to regulate inflammation," *Nature Immunology*, 14(5): 470-479, May 2013.

Chen et al., "Calmodulin Antagonizes a Calcium-Activated SCF Ubiquitin E3 Ligase Subunit, FBXL2, To Regulate Surfactant Homeostasis," *Molecular and Cellular Biology*, 31(9): 1905-1920, May 1, 2011.

Grabenko et al., "Synthesis and study of p-substituted toluoyl derivatives of ethylenediamine and piperzine," *Ukrainskii Khimicheskii Zhurnal*, 47(9): 956-959, 1981 (English translation).

Huang et al., "Syntheses, crystal structures and properties of silver (I) and copper (II) complexes with an oxazoline-containing tetradentate ligand," *New Journal of Chemistry*, 34:2436-2444, 2010.

International Search Report and Written Opinion from International Application No. PCT/US2013/030995, dated Jun. 13, 2013.

International Search Report and Written Opinion from International Application No. PCT/US2014/069368, dated Mar. 17, 2015.

Kauffman et al., "A heterocyclohexaaromatic compound with 'face-to-face' arrangement of two benzene rings," *Angewandte Chemie*, 90(10): 804-805, 1978 (English abstract only).

Khan et al., "Synthesis, anti-inflammatory and analgesic activity of new hexahydro-pyrimidine derivatives," *Pharmazie*, 57:377-383, 2002.

Lakatos et al., "Two pyridine derivatives as potential Cu(II) and Zn(II) chelators in therapy for Alzheimer's disease," *The International Journal for Inorganic, Organometallic and Bioinorganic Chemistry*, 39:1302-1315, Jan. 1, 2010.

Lexy et al., "Heterocyclopolyaromatics, X. The first cyclohexaaromatic compound with 'face-to-face' arrangement of two aromatic ring members," *Chemiste Berichte*, 113(8): 2749-2754, 1980 (English abstract only).

Mallampalli et al., "Targeting F box protein Fbxo3 to control cytokine-driven inflammation," *Journal of Immunology*, 191(10): 5247-5255, Oct. 11, 2013.

PubChem, SID 103190923, Dec. 22, 2010, http://pubchem.ncbi.nlm.nih.gov/substance103190923.

PubChem, SID 103191203, Dec. 22, 2010, http://pubchem.ncbi.nih.gov/substance/103191203.

Sharma et al., "Synthesis, antimicrobial activity, and structure-activity relationship study of N,N-dibenzyl-cyclohexane-1,2-diamine derivatives," *European Journal of Medicinal Chemistry*, 46:480-487, 2011.

Kraml et al., "Agents Affecting Lipid Metabolism. VIII. N,N-Dibenzylethylenediamine, the Key to a Novel Class of Cholesterol Biosynthesis Inhibitors," *J. Med. Chem.*, vol. 7, pp. 500-503, 1964.

Lakatos et al., "Two pyridine derivatives as potential Cu(II) and Zn(II) chelators in therapy for Alzheimer's disease," *Dalton Transactions*, 39(5): 1302-1315, Nov. 27, 2009.

Official Action issued by Japan Patent Office dated Sep. 29, 2016, for Japanese Application No. 2015-516008 (English translation).

Sundravel et al., "Synthesis, structure, spectra and reactivity of iron(III) complexes of facially coordinating and sterically hindering 3N ligands as models for catechol dioxygenases," *Dalton Transactions*, pp. 7012-7025, Nov. 3, 2008.

Yigit, "The Synthesis of Some Perhydrobenzimidazolimium Salts and Their Application Pd-Carbene Catalyzed Heck and Suzuki Reactions," *Molecules*, vol. 14, pp. 2032-2042, Jun. 5, 2009.

Cisneros et al., "Efficacy of moxifloxacin monotherapy versus gatifloxacin monotherapy, piperacillin-tazobactam combination therapy, and clindamycin plus gentamicin combination therapy: an experimental study in a rat model of intra-abdominal sepsis induced by fluoroquinolone-resistant *Bacteroides fragilis*," *Current Therapeutic Research*, 48(6): 1021-1029, 1990.

Examination Report issued for EPC application No. 13800256.3 issued by the European Patent Office dated Aug. 29, 2016.

Gakhar et al., "Anti-tumor effect of primaquine compounds in human breast cancer cells," *Proceedings of the American Association for Cancer Research Annual Meeting—98th Annual Meeting of the American Associate for Cancer Research*, 67(9), May 2007.

Hagers Handbuch der Pharmazeutischen Praxis, vol. 2, p. 828, 1998.

STN Registry No. 1209629-41-3, entered Mar. 14, 2010.

Valcke et al., "Penetration of Ampicillin and Sulbactam in the Lower Airways During Respiratory Infections," *Antimicrobial Agents and Chemotherapy*, 34(6): 958-962, 1990.

Newman et al., "Chiral metal complexes. Part 33. Coordination stereoselectivity in ternary cobalt(III) complexes of dipeptides and an optically active triamine," *Inorganica Chimica Acta*, vol. 183, pp. 145-155, Oct. 10, 1990.

* cited by examiner

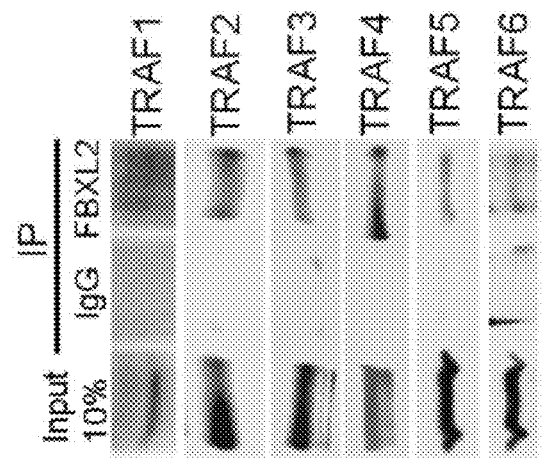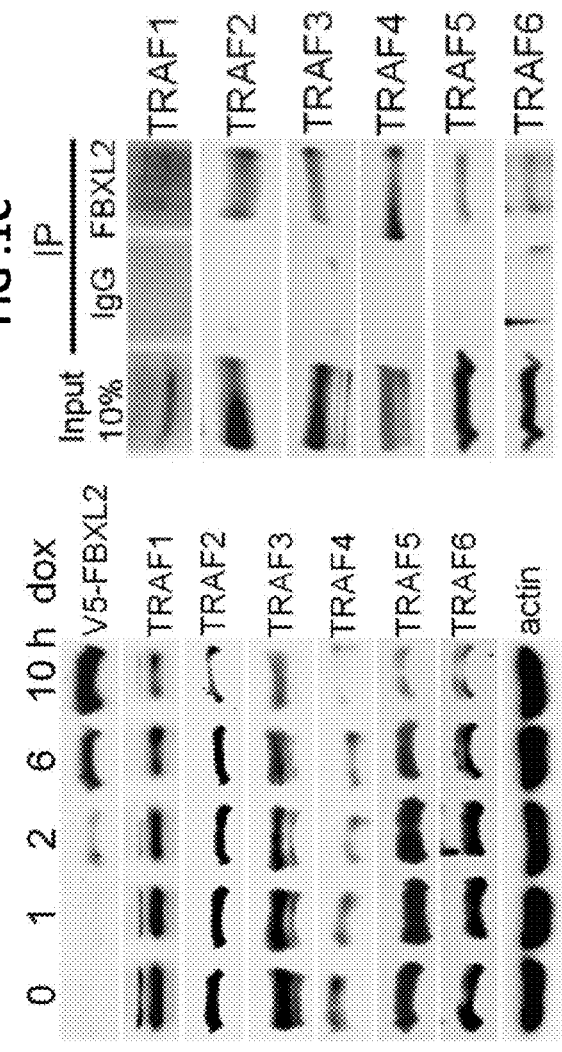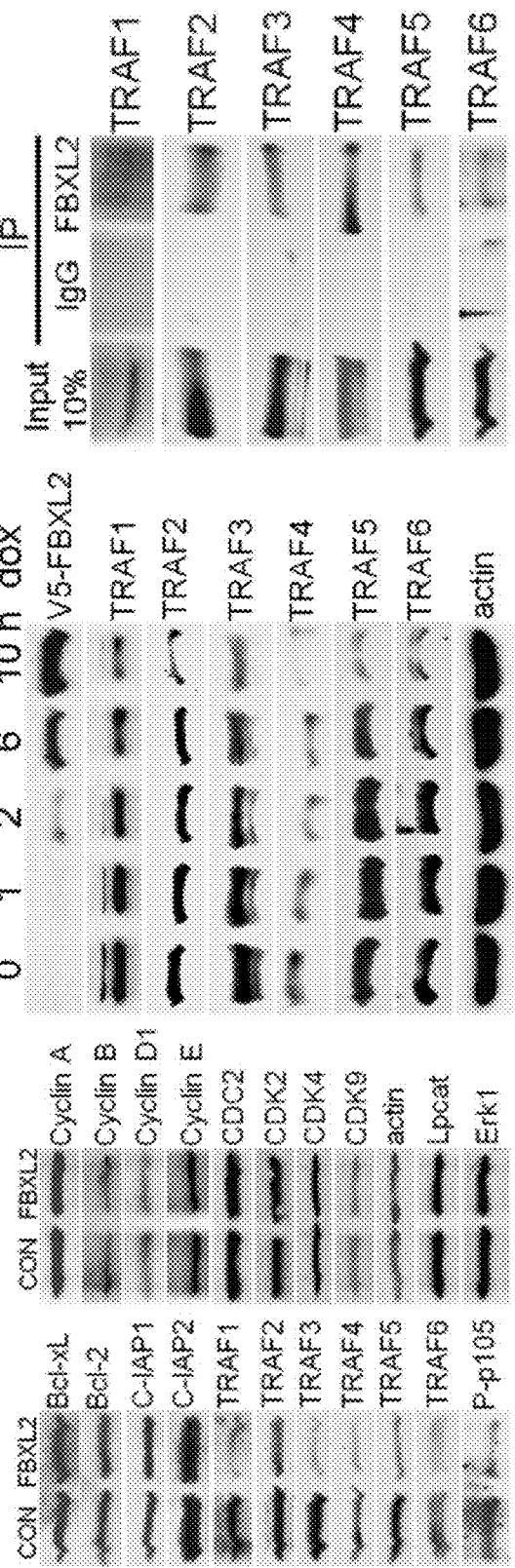

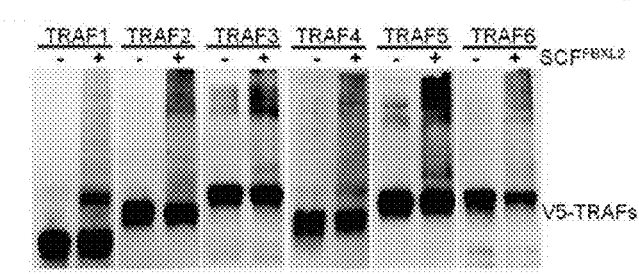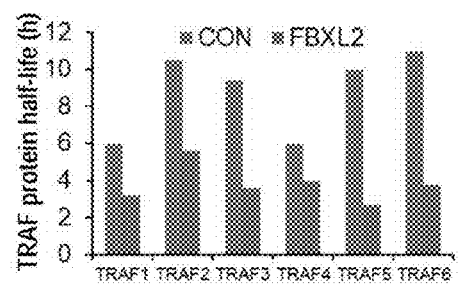
FIG .1D
FIG .1E

FIG. 2C
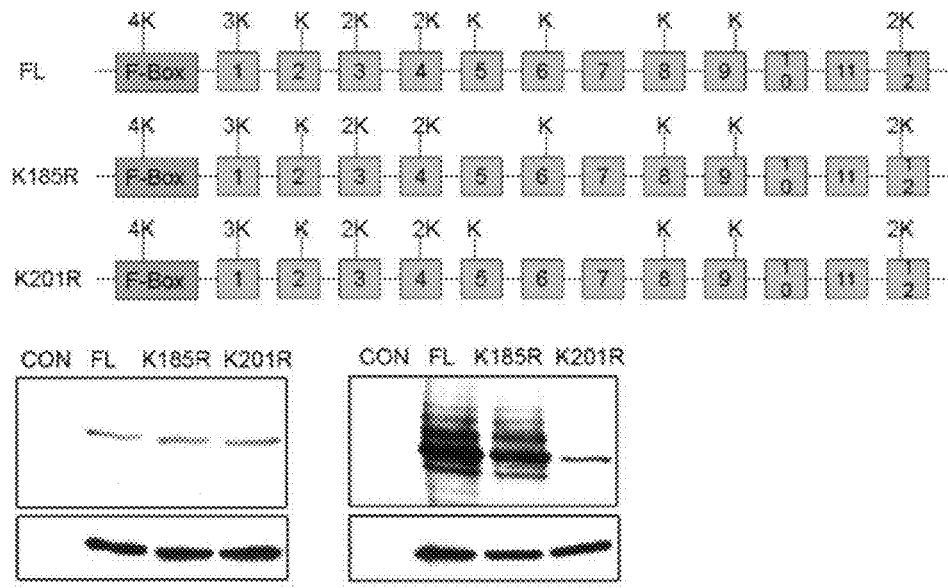
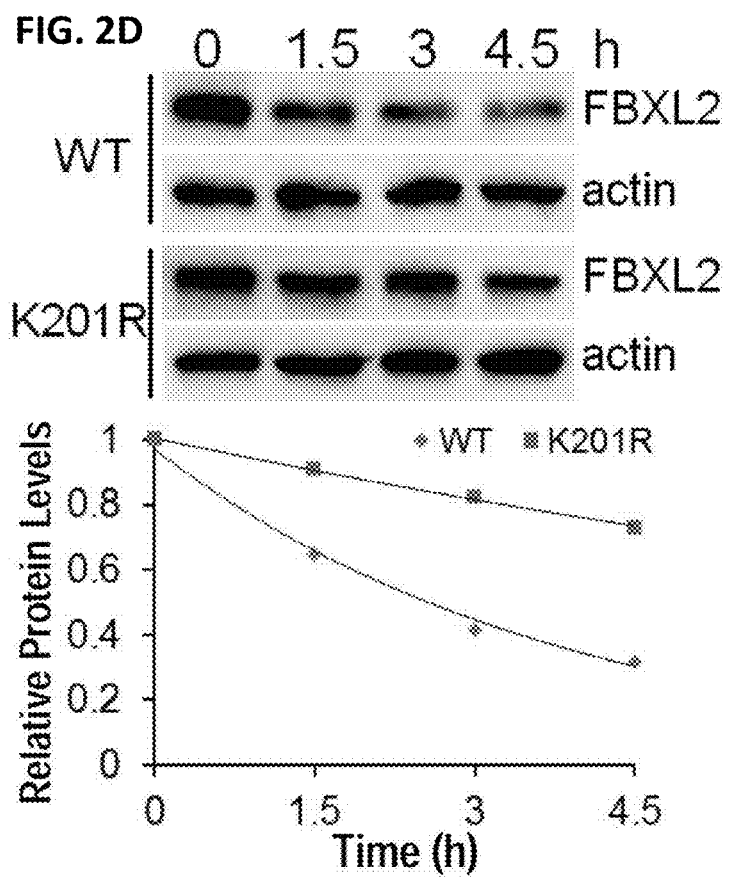
FIG. 2D

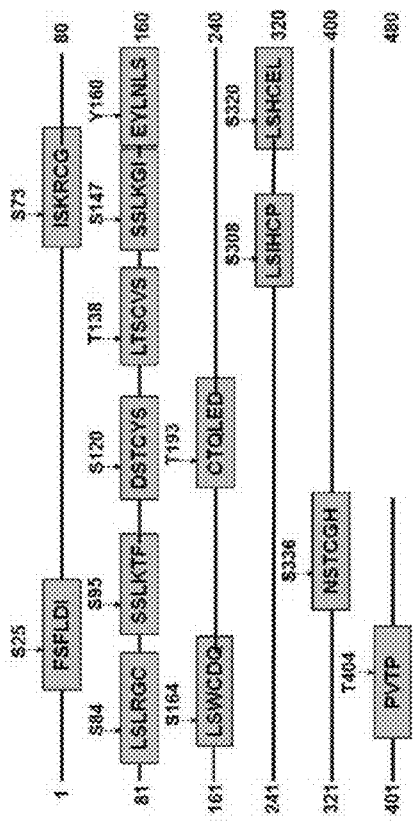
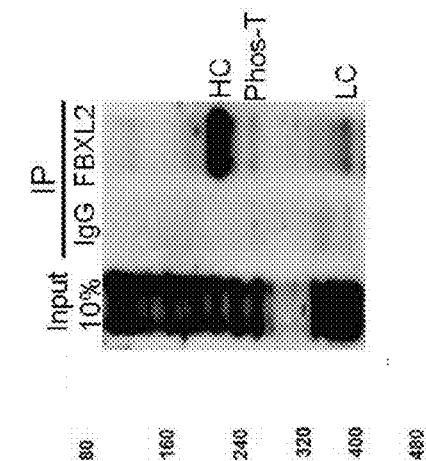
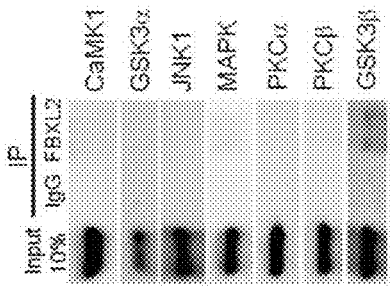
FIG. 3A
FIG. 3B
FIG. 3C

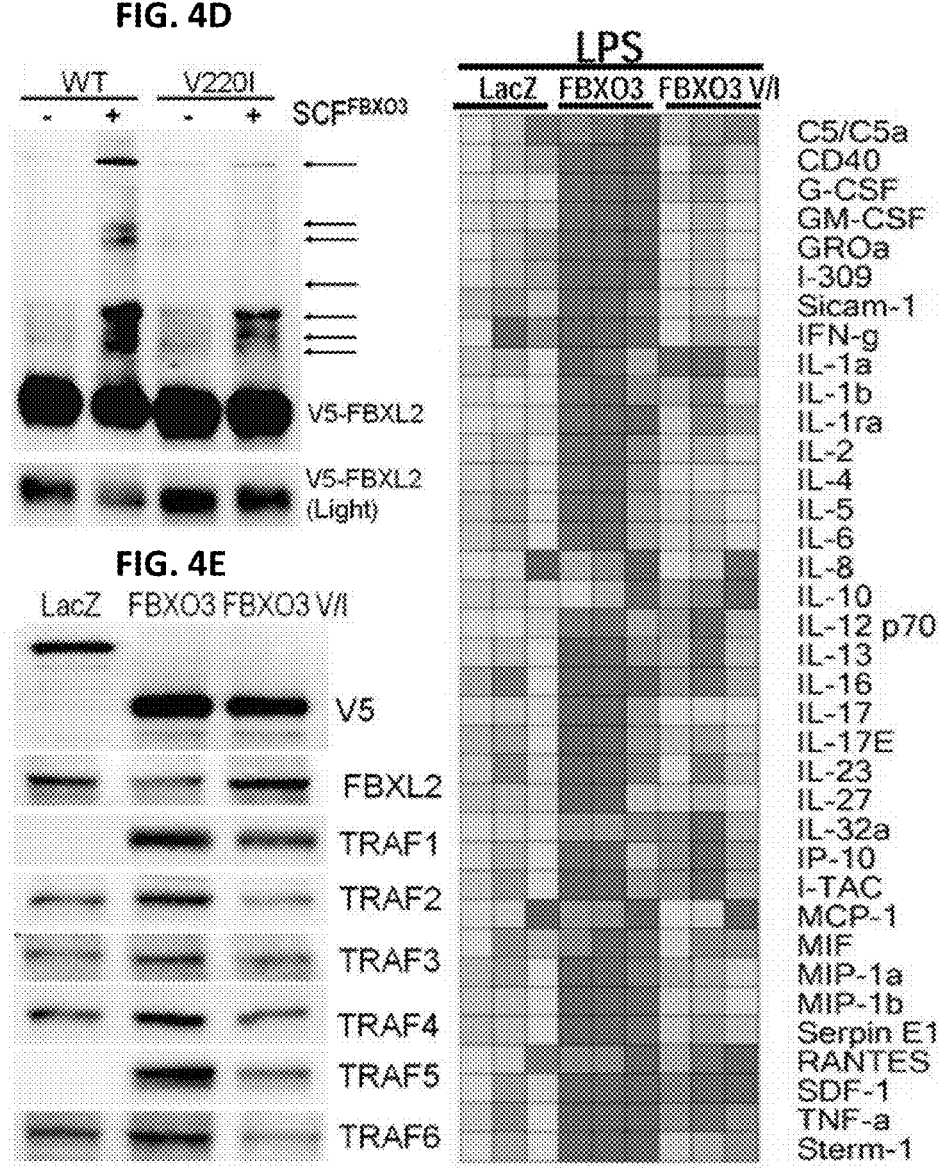

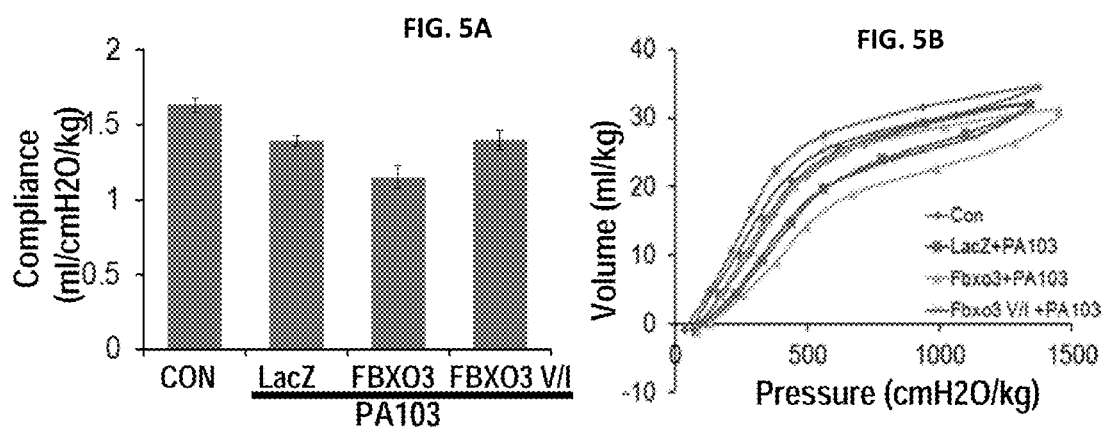

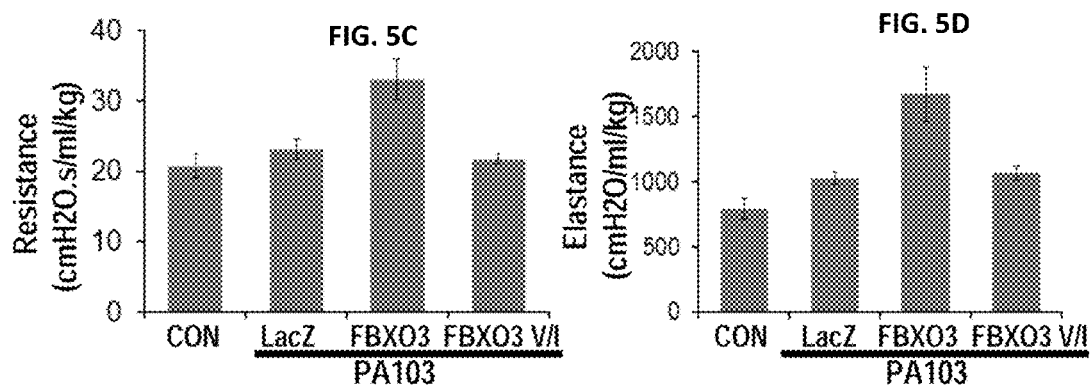

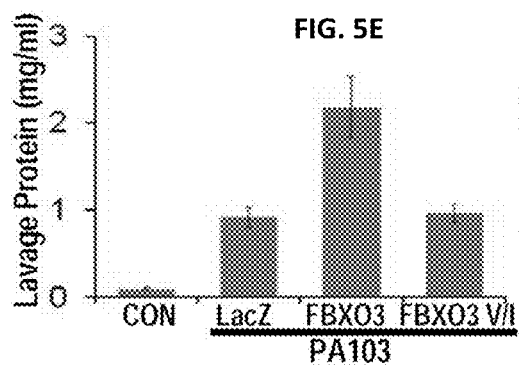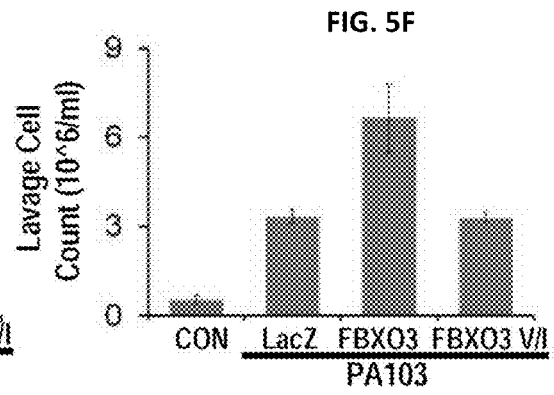

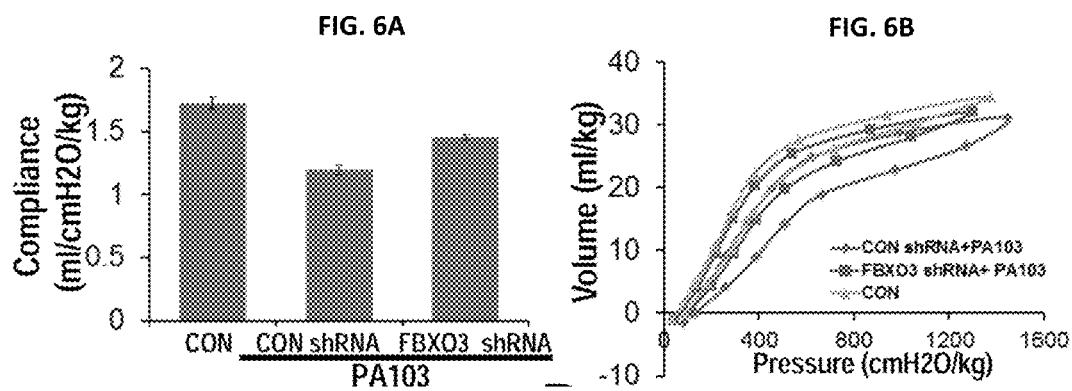

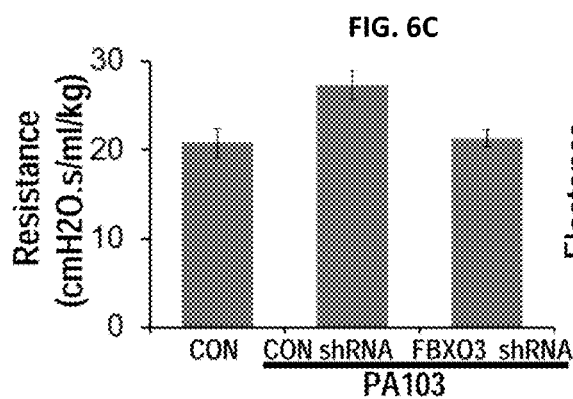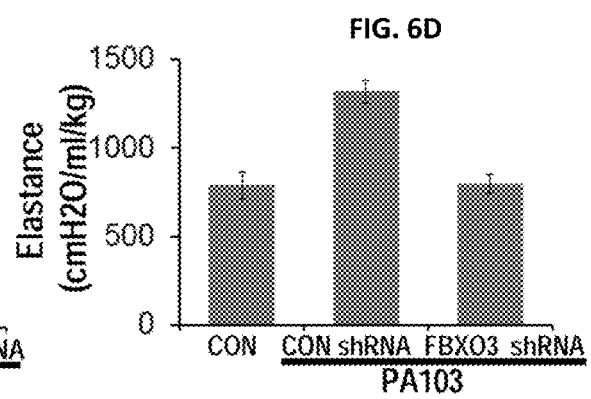

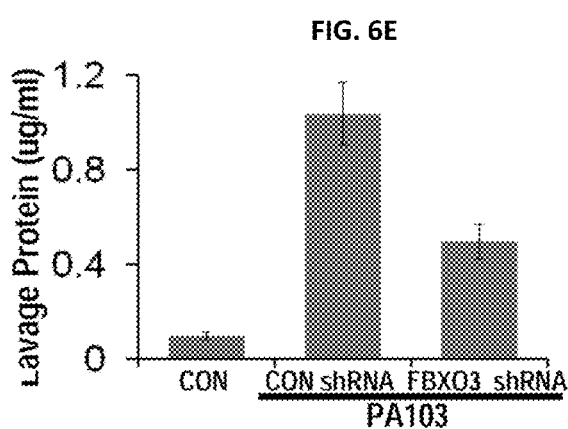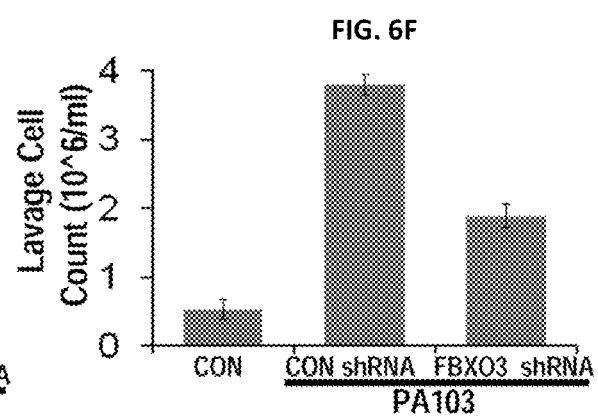

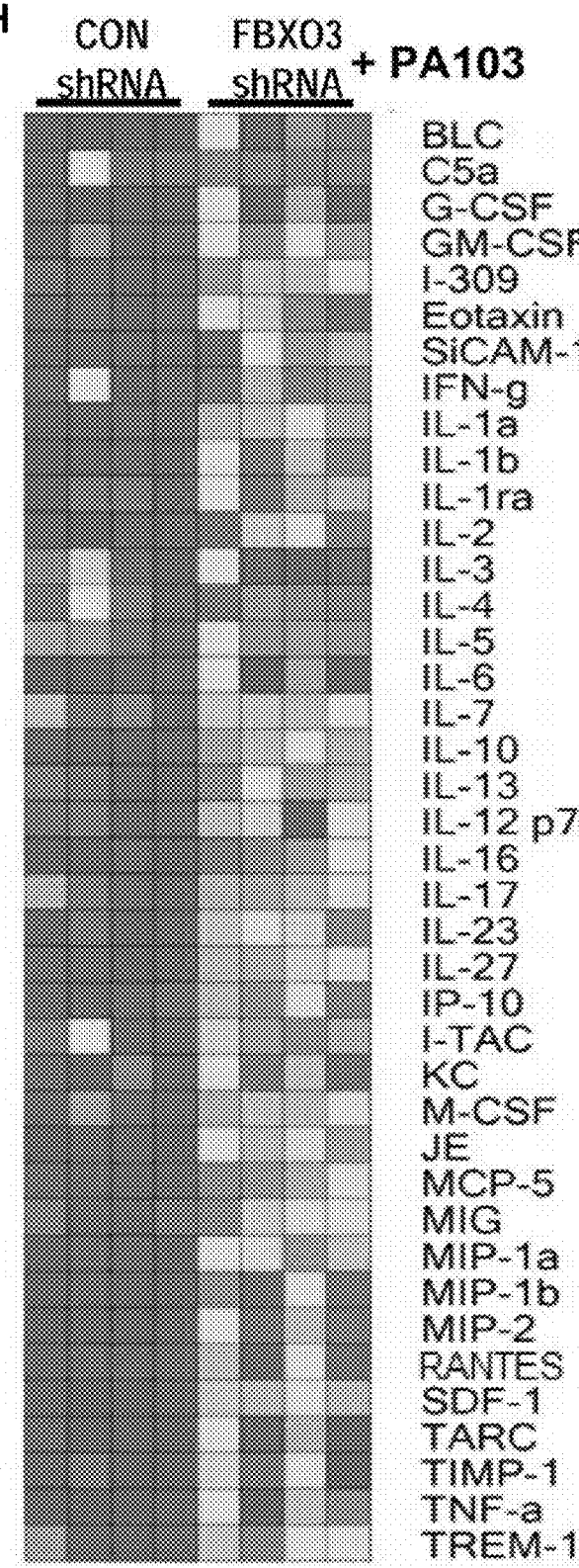

Benzathine

BC-1215

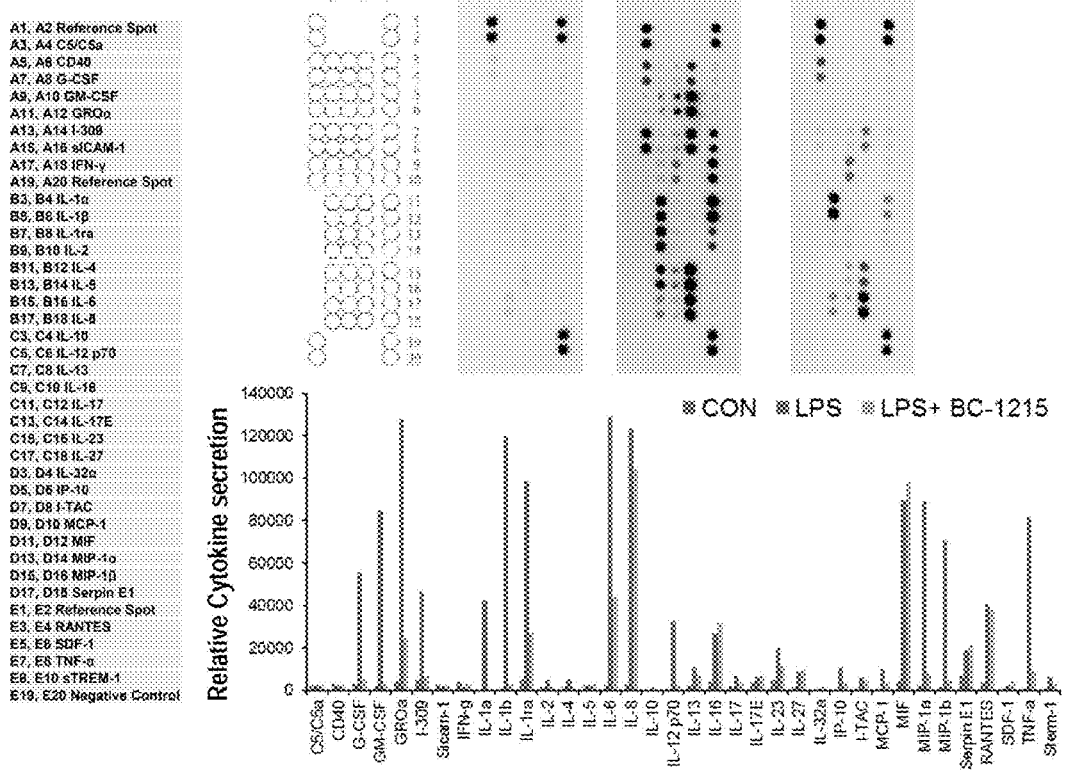

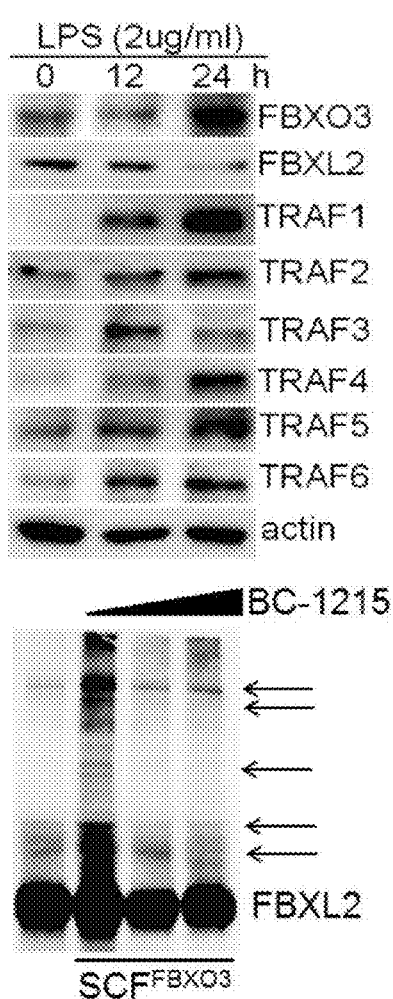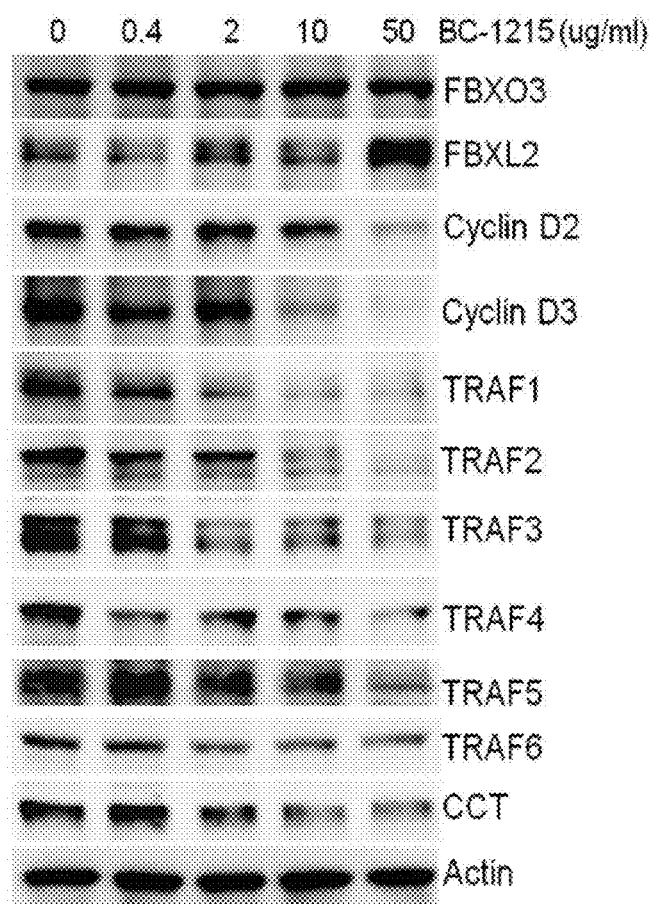
FIG. 10A
FIG. 10B
FIG. 10C

*In vivo* LPS induced sepsis model

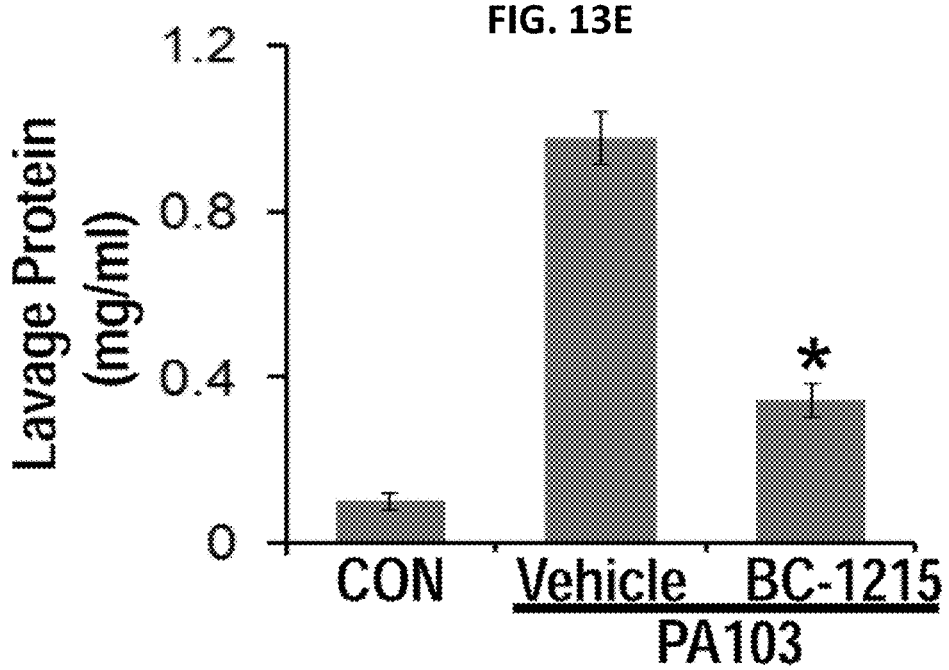
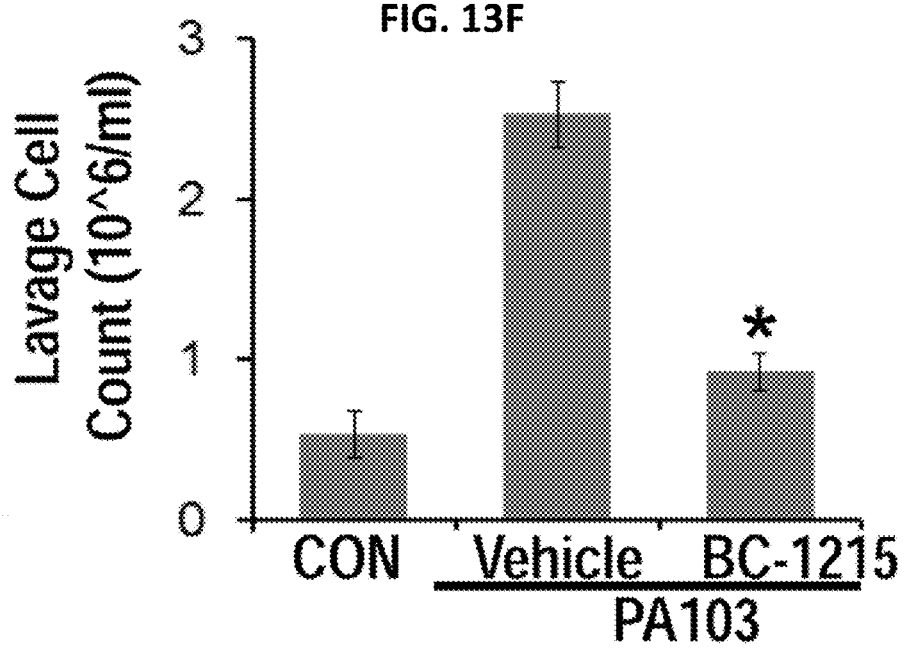

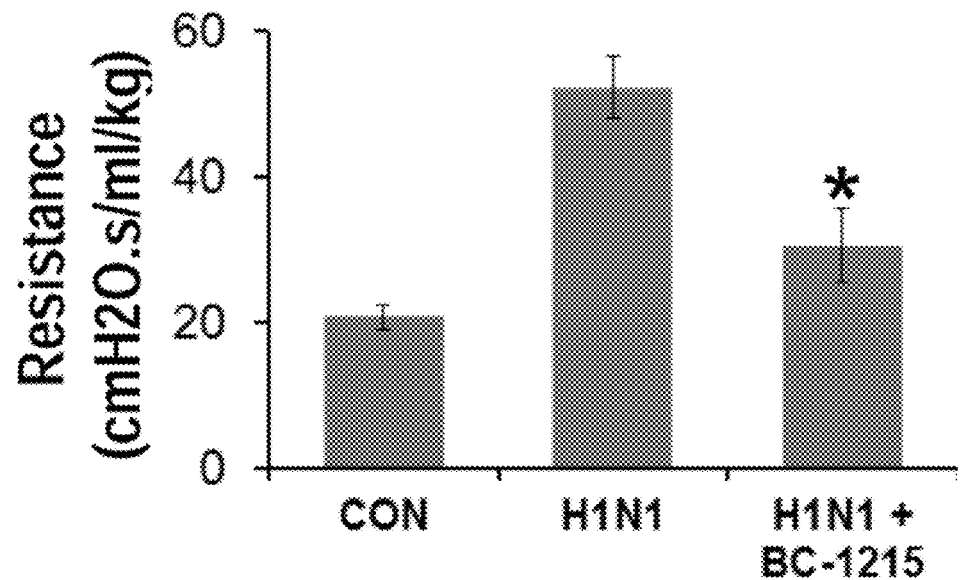
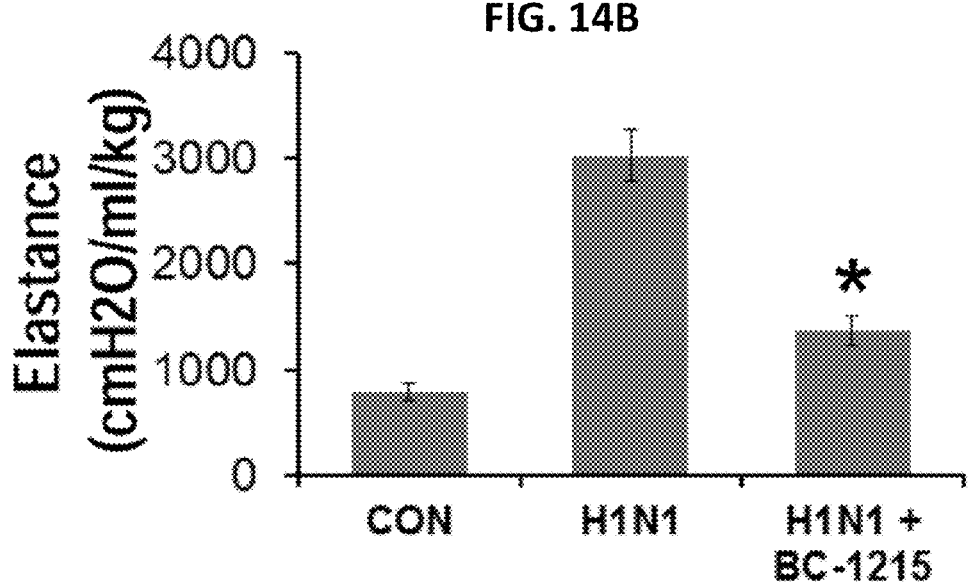

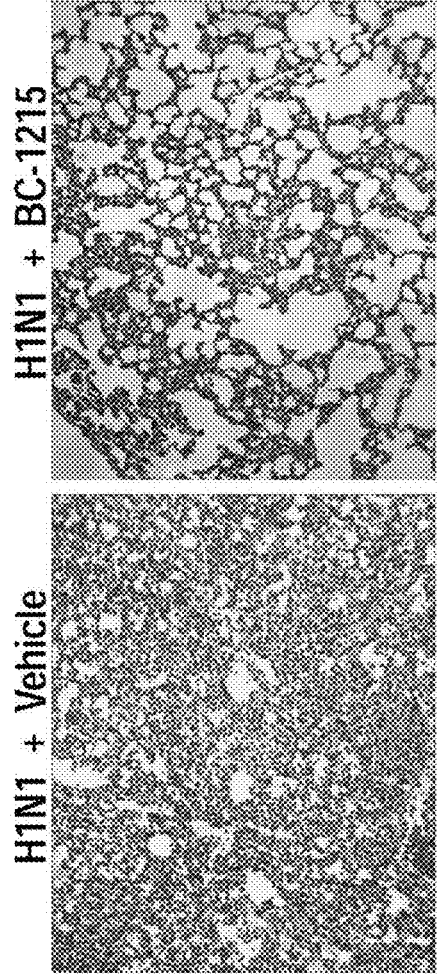
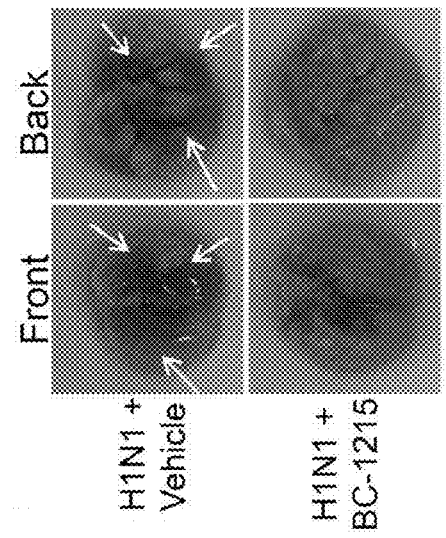

FIG. 15A  *In vivo* TPA induced ear edema
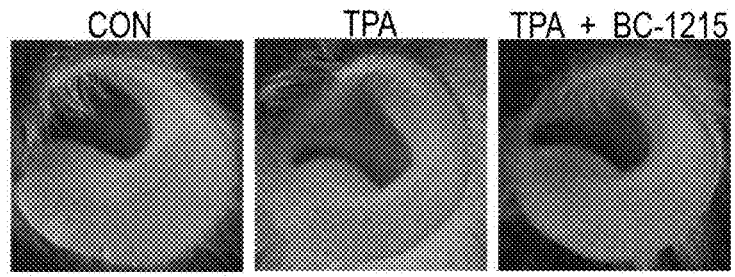
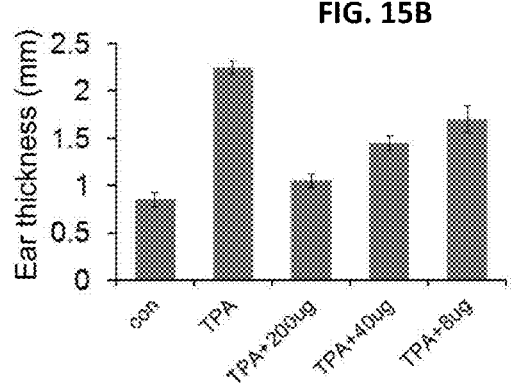
FIG. 15B
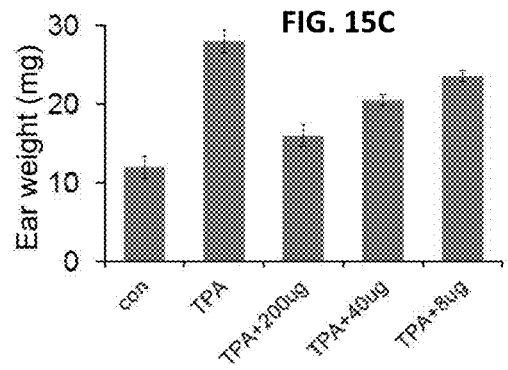
FIG. 15C

FIG. 16A
*In vivo* mouse paw edema model
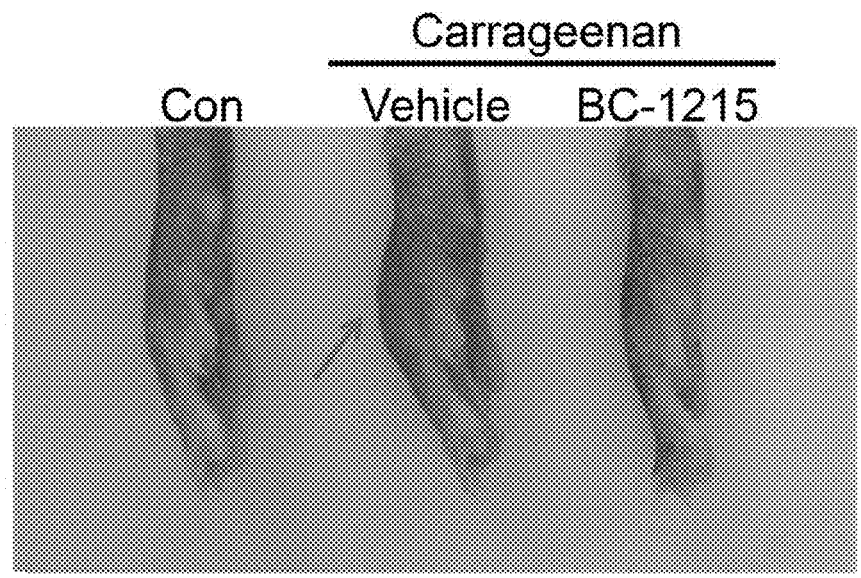
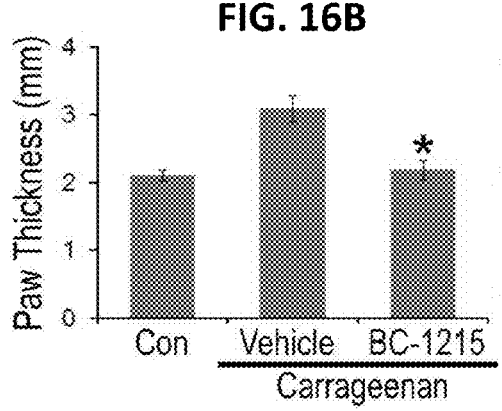
FIG. 16B
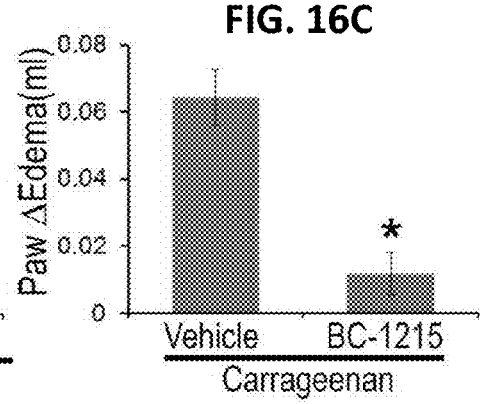
FIG. 16C

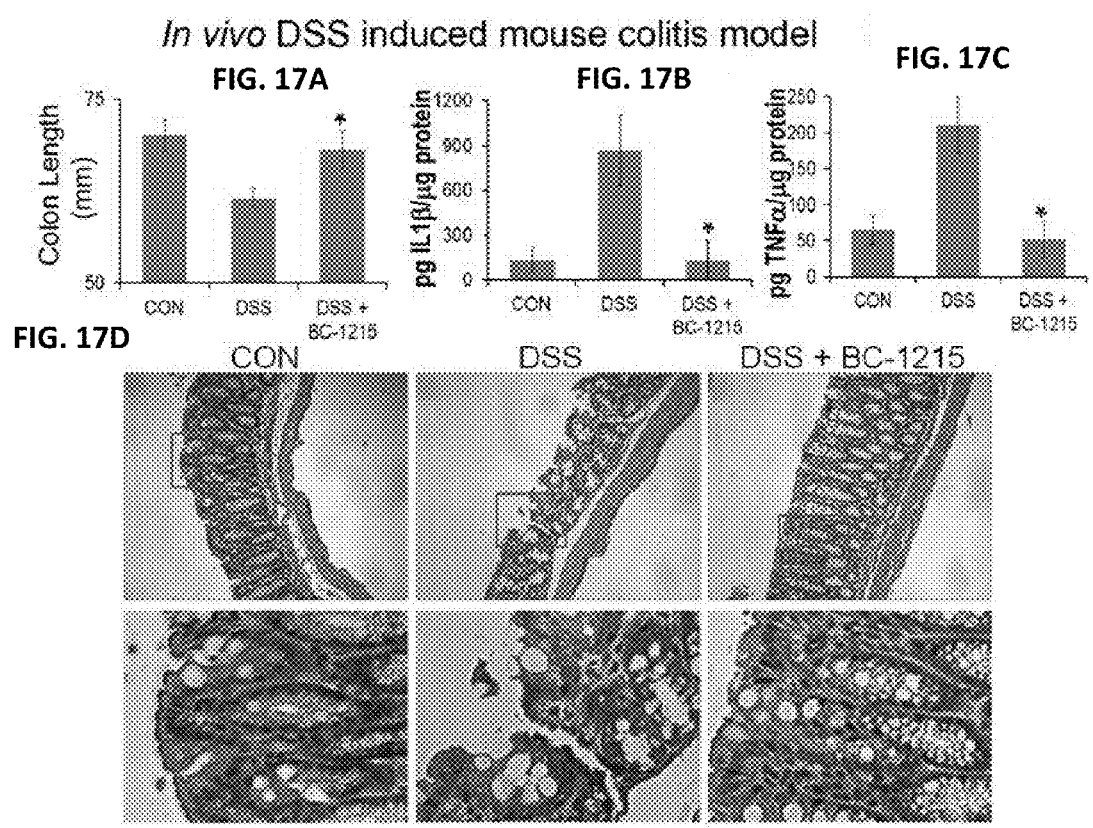

FIG. 19 Kirby-Bauer antibiotic testing

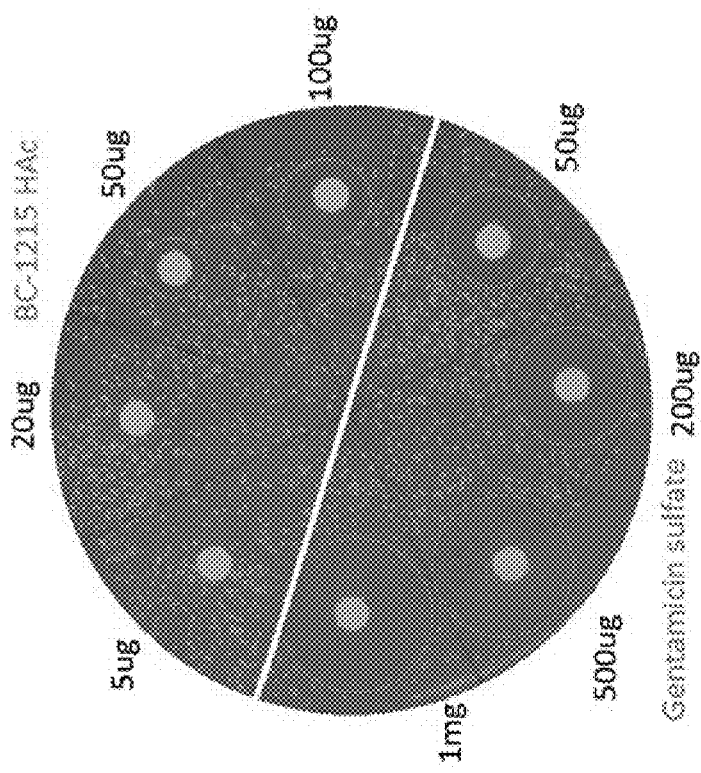

BC-1215 was tested in antibiotic sensitivity test using Mueller-Hinton agar. Briefly, 6mm filter papers containing different amount of BC-1215 or Gentamicin (positive control) were added on the Mueller-Hinton agar pre-exposed to *Staphylococcus aureus*. The plates were incubated at 37 degree for 24h. Zone sizes were measured and marked by red circle indicating positive results.

FIG. 20A

| | | IL1b assay, Apoptosis | IC50, LD50, TI |
|---|---|---|---|
| Benzathine | [structure] | Benzathine IC50, Benzathine LD50 | $IC50_{IL1b}$ =25ug/ml; LD50 =400ug/ml; TI=16 |
| BC-1202 | [structure] | BC-1202 IC50, BC-1202 LD50 | $IC50_{IL1b}$ =0.8ug/ml; LD50 =0.9ug/ml; TI=1.1 |
| BC-1203 | [structure] | BC-1203 IC50, BC-1203 LD50 | $IC50_{IL1b}$ =5ug/ml; LD50 =34ug/ml; TI=6.6 |
| BC-1204 | [structure] | BC-1204 IC50, BC-1204 LD50 | $IC50_{IL1b}$ =5ug/ml; LD50 =120ug/ml; TI=24 |

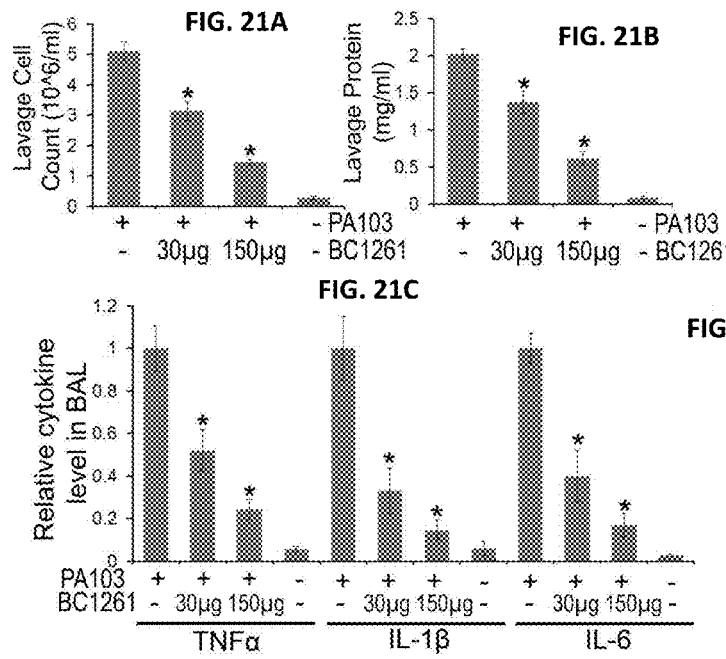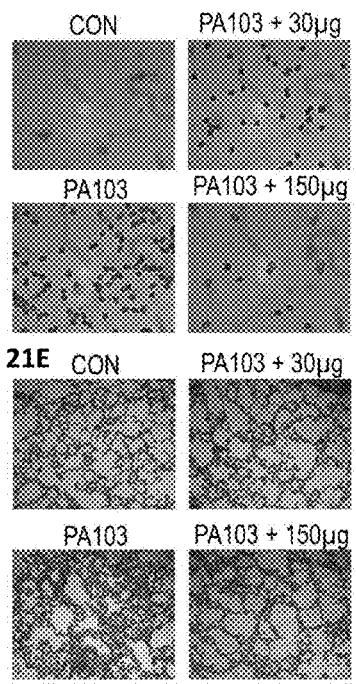
FIG. 21A, FIG. 21B, FIG. 21C, FIG. 21D, FIG. 21E

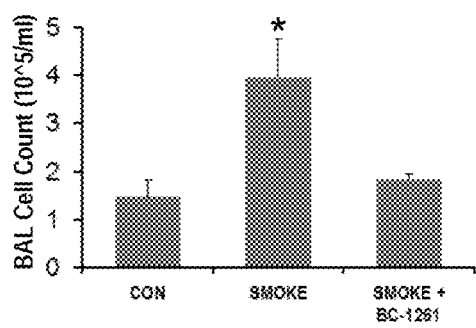
FIG. 22A
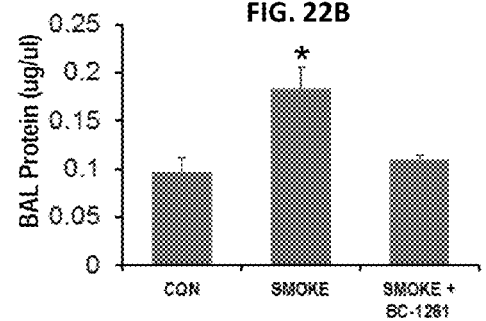
FIG. 22B
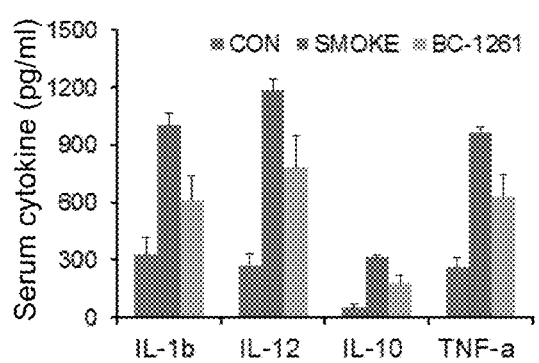
FIG. 22C
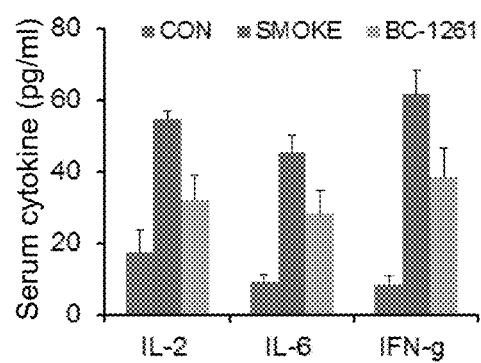

FIG. 23A
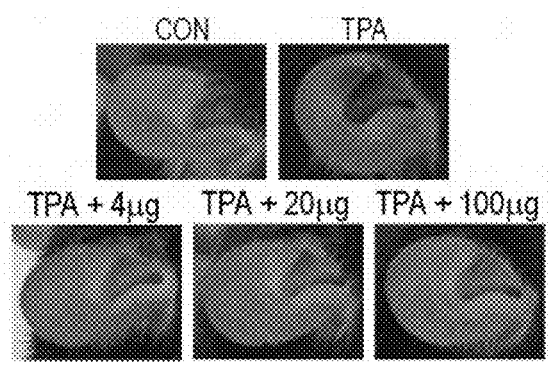
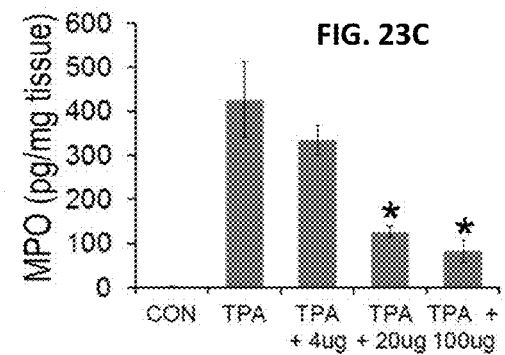
FIG. 23C
FIG. 23B
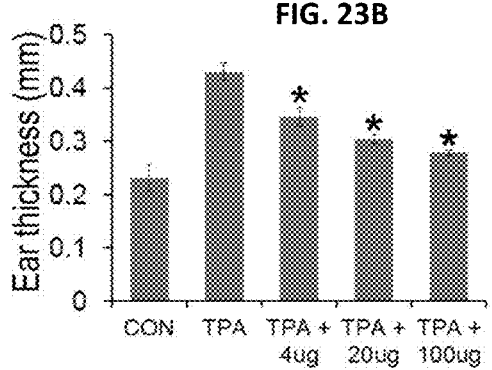
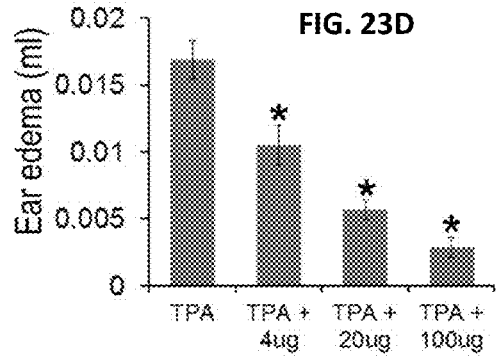
FIG. 23D

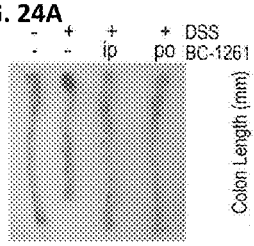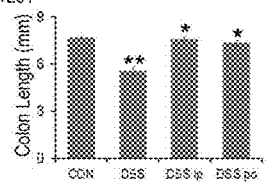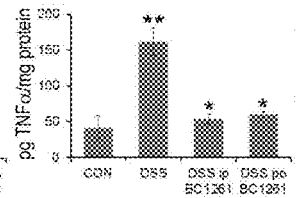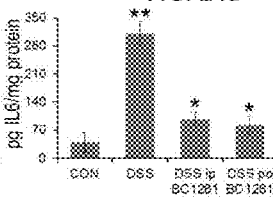
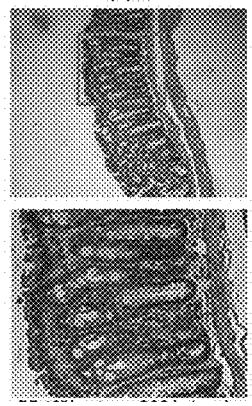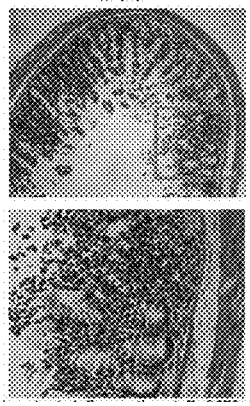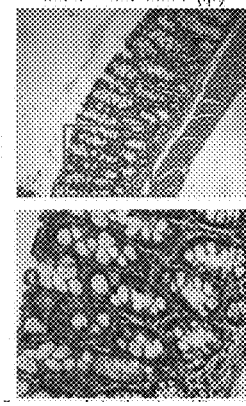
FIG. 24A, FIG. 24B, FIG. 24C, FIG. 24D, FIG. 24E
CON — DSS — DSS + BC1261 (ip) — DSS + BC1261 (po)

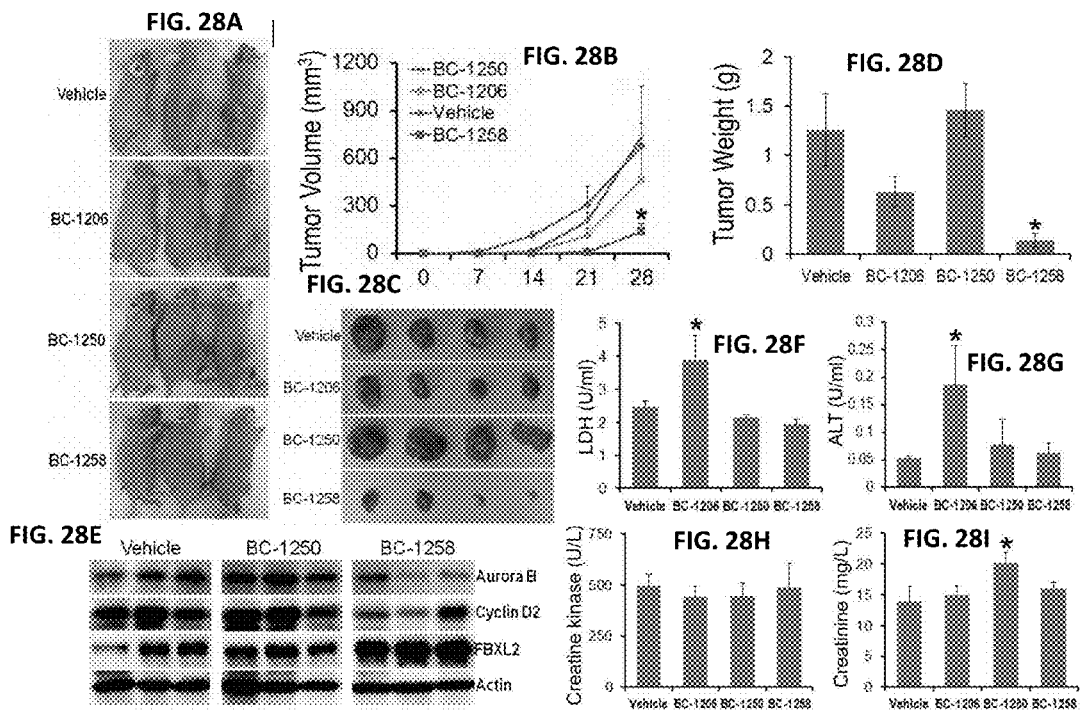

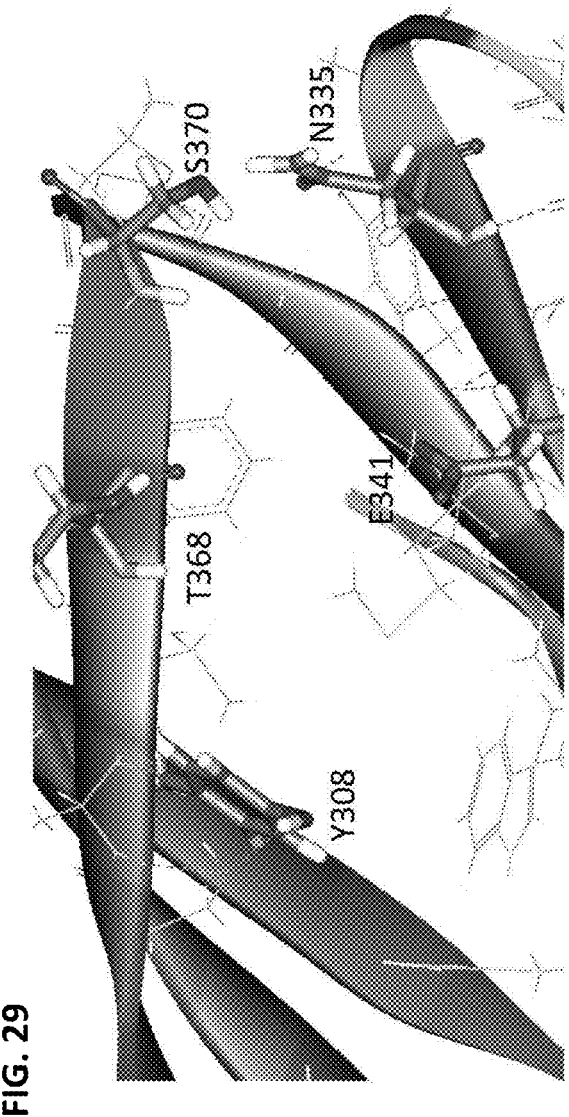
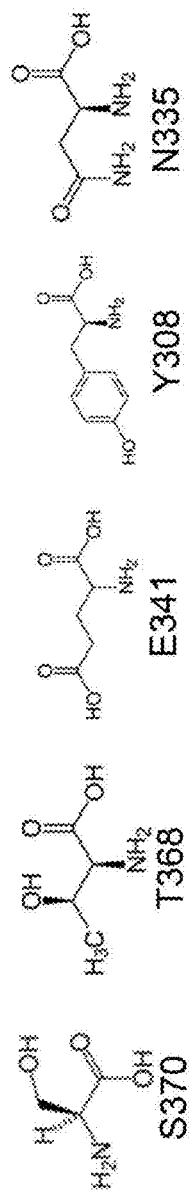
FIG. 29
FBXO3 amino acid Y308, N335, E341, T368 and S370 form a drug binding motif.

FIG. 30
FBXO3-ApaG Residue E341 interaction with BC-1261
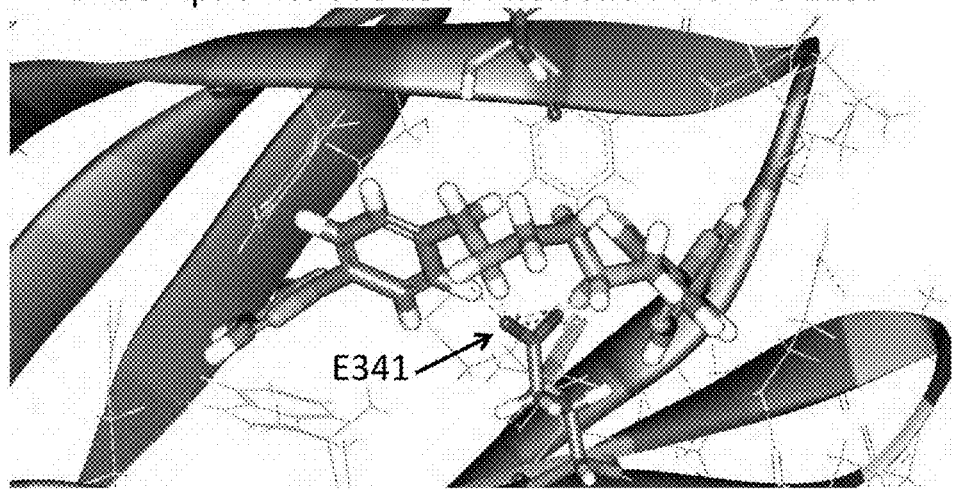
FBXO3-ApaG Residues E341 and T368 interaction with BC-1234
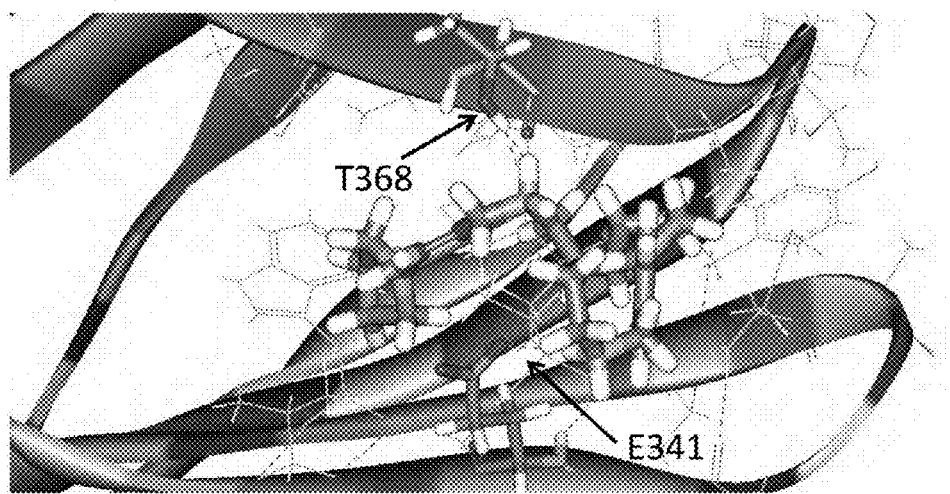

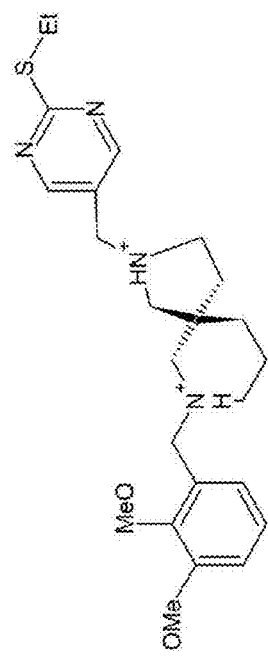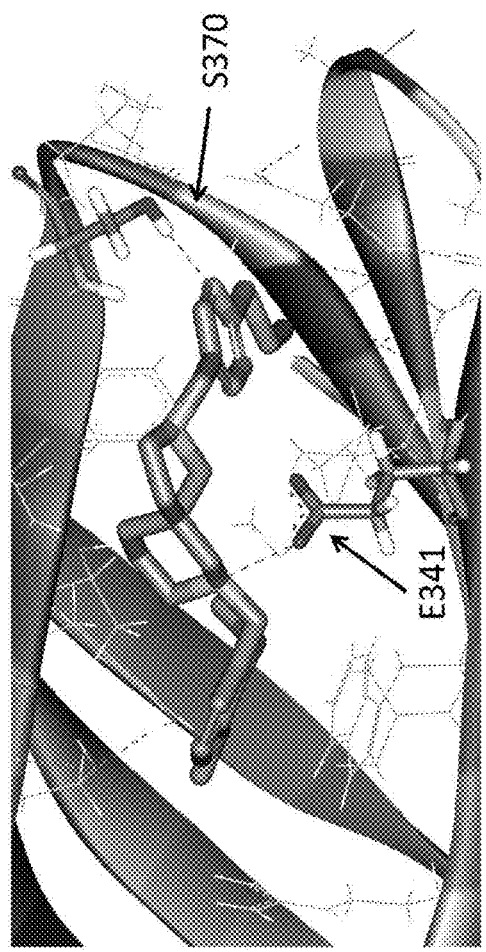
FIG. 31 FBXO3-ApaG Residues E341 and T368 interaction with BC-1304

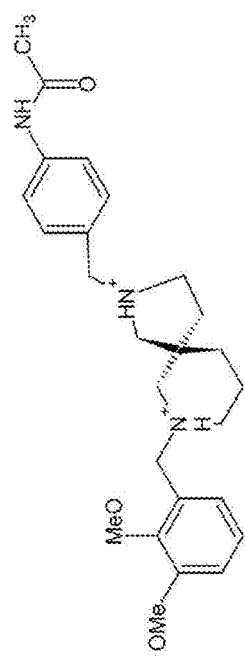
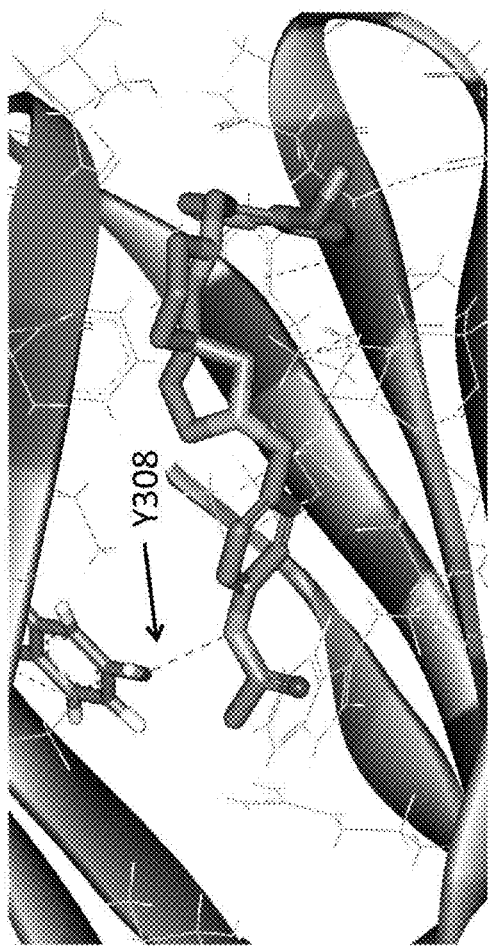
FIG. 33 FBXO3-ApaG Residues Y308 with BC-1305 (Secondary position)

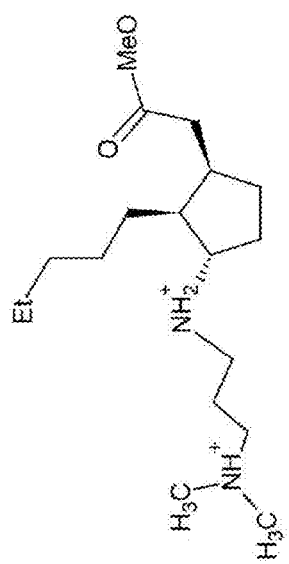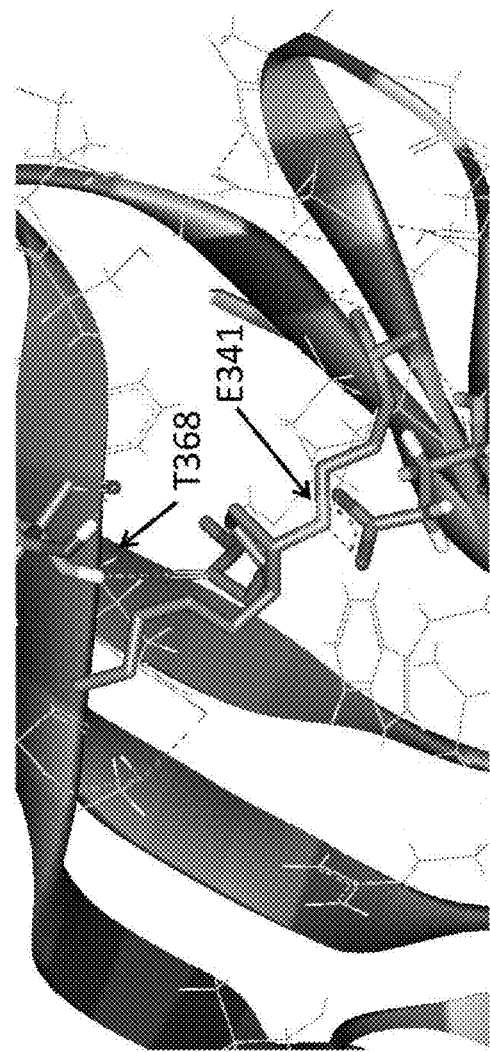
FBXO3-ApaG Residues E341 and T368 interaction with BC-1307
FIG. 35

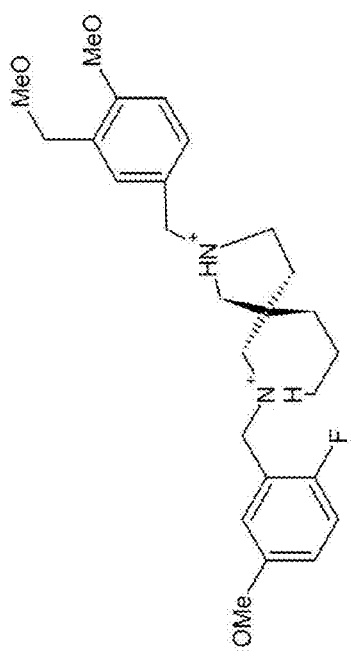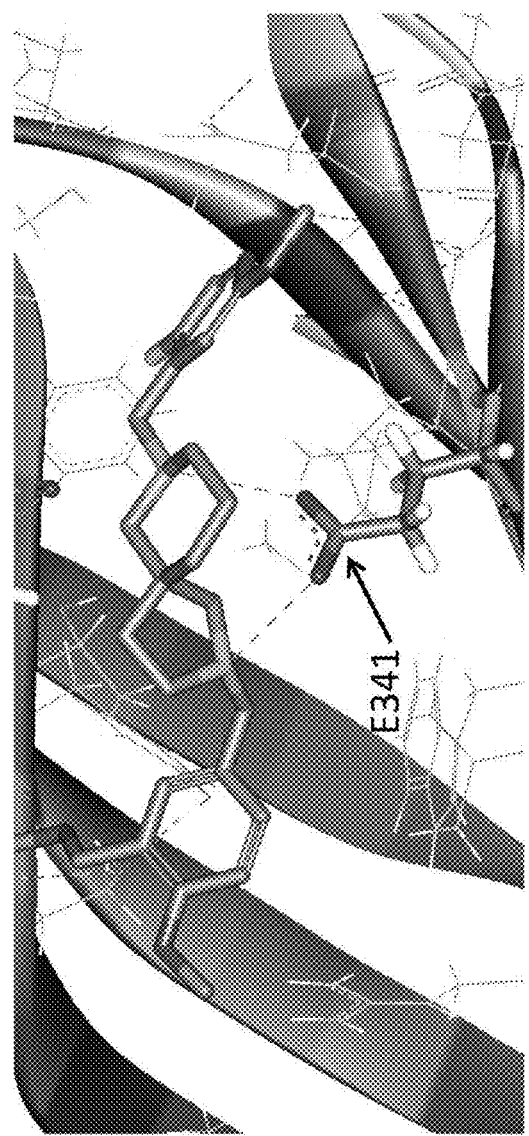
FBXO3-ApaG Residues E341 interaction with BC-1308
FIG. 36

FIG. 38 Summary of In vitro Toxicity/off targeting experiments

| Assay | BC-1215 % Inh | BC-1261 % Inh |
|---|---|---|
| CYP450, 2D6 | 51 | 28 |
| CYP450, 3A4 | 74 | 46 |
| Nitric Oxide Synthase, Neuronal (nNOS) | 83 | 32 |
| Adrenergic α1, Non-Selective | 55 | -4 |
| Adrenergic α2, Non-Selective | 50 | 36 |
| Calcium Channel L-Type, Phenylalkylamine | 72 | -2 |
| Opiate μ(OP3, MOP) | 44 | 10 |
| Potassium Channel HERG | 55 | 8 |
| Serotonin (5-Hydroxytryptamine) 5-HT2 | 57 | 31 |
| Serotonin (5-Hydroxytryptamine) 5-HT2B | 84 | 20 |
| Serotonin (5-Hydroxytryptamine) 5-HT2C | 61 | 37 |
| Serotonin (5-Hydroxytryptamine) 5-HT4 | 49 | 19 |
| Sodium Channel, Site 2 | 103 | 43 |
| Transporter, Dopamine (DAT) | 81 | 25 |
| Transporter, Norepinephrine (NET) | 86 | 51 |
| Transporter, Serotonin (5-Hydroxytryptamine) (SERT) | 58 | 6 |
| Histamine H2 | 84 | 85 |
|  | 15/109 | 2/109 |

Out of 109 assays tested, BC1215 generates 15 hits (>50% inhibition of activity), whereas BC-1261 only generates 2 hits

SEQUENCE LISTING

```
<160> NUMBER OF SEQ ID NOS: 1

<210> SEQ ID NO 1
<211> LENGTH: 471
<212> TYPE: PRT
<213> ORGANISM: Homo sapiens
<220> FEATURE:
<221> NAME/KEY: MISC_FEATURE
<222> LOCATION: (278)..(400)
<223> OTHER INFORMATION: ApaG motif

<400> SEQUENCE: 1
```

Met Ala Ala Met Glu Thr Glu Thr Ala Pro Leu Thr Leu Glu Ser Leu
1               5                   10                  15

Pro Thr Asp Pro Leu Leu Leu Ile Leu Ser Phe Leu Asp Tyr Arg Asp
            20                  25                  30

Leu Ile Asn Cys Cys Tyr Val Ser Arg Arg Leu Ser Gln Leu Ser Ser
        35                  40                  45

His Asp Pro Leu Trp Arg Arg His Cys Lys Lys Tyr Trp Leu Ile Ser
    50                  55                  60

Glu Glu Lys Thr Gln Lys Asn Gln Cys Trp Lys Ser Leu Phe Ile
65                  70                  75                  80

Asp Thr Tyr Ser Asp Val Gly Arg Tyr Ile Asp His Tyr Ala Ala Ile
                85                  90                  95

Lys Lys Ala Trp Asp Asp Leu Lys Lys Tyr Leu Glu Pro Arg Cys Pro
            100                 105                 110

Arg Met Val Leu Ser Leu Lys Glu Gly Ala Arg Glu Glu Asp Leu Asp
        115                 120                 125

Ala Val Glu Ala Gln Ile Gly Cys Lys Leu Pro Asp Asp Tyr Arg Cys
    130                 135                 140

Ser Tyr Arg Ile His Asn Gly Gln Lys Leu Val Val Pro Gly Leu Leu
145                 150                 155                 160

Gly Ser Met Ala Leu Ser Asn His Tyr Arg Ser Glu Asp Leu Leu Asp
                165                 170                 175

Val Asp Thr Ala Ala Gly Gly Phe Gln Gln Arg Gln Gly Leu Lys Tyr
            180                 185                 190

Cys Leu Pro Leu Thr Phe Cys Ile His Thr Gly Leu Ser Gln Tyr Ile
        195                 200                 205

```
Ala Val Glu Ala Ala Glu Gly Arg Asn Lys Asn Glu Val Phe Tyr Gln
    210             215                 220
Cys Pro Asp Gln Met Ala Arg Asn Pro Ala Ala Ile Asp Met Phe Ile
225             230                 235             240
Ile Gly Ala Thr Phe Thr Asp Trp Phe Thr Ser Tyr Val Lys Asn Val
                245                 250                 255
Val Ser Gly Gly Phe Pro Ile Ile Arg Asp Gln Ile Phe Arg Tyr Val
                260                 265                 270
His Asp Pro Glu Cys Val Ala Thr Thr Gly Asp Ile Thr Val Ser Val
            275                 280                 285
Ser Thr Ser Phe Leu Pro Glu Leu Ser Ser Val His Pro Pro His Tyr
    290                 295                 300
Phe Phe Thr Tyr Arg Ile Arg Ile Glu Met Ser Lys Asp Ala Leu Pro
305                 310                 315                 320
Glu Lys Ala Cys Gln Leu Asp Ser Arg Tyr Trp Arg Ile Thr Asn Ala
                325                 330                 335
Lys Gly Asp Val Glu Val Gln Gly Pro Gly Val Val Gly Glu Phe
                340                 345                 350
Pro Ile Ile Ser Pro Gly Arg Val Tyr Glu Tyr Thr Ser Cys Thr Thr
            355                 360                 365
Phe Ser Thr Thr Ser Gly Tyr Met Glu Gly Tyr Tyr Thr Phe His Phe
    370                 375                 380
Leu Tyr Phe Lys Asp Lys Ile Phe Asn Val Ala Ile Pro Arg Phe His
385             390                 395                 400
Met Ala Cys Pro Thr Phe Arg Val Ser Ile Ala Arg Leu Glu Met Gly
                405                 410                 415
Pro Asp Glu Tyr Glu Glu Met Glu Glu Glu Glu Glu Glu Glu Glu Glu
                420             425                 430
Glu Asp Glu Asp Asp Ser Ala Asp Met Asp Glu Ser Asp Glu Asp
            435                 440                 445
Asp Glu Glu Glu Arg Arg Arg Arg Val Phe Asp Val Pro Ile Arg Arg
    450                 455                 460
Arg Arg Cys Ser Arg Leu Phe
465             470
```

BENZATHINE ANALOGS

CROSS REFERENCE TO RELATED APPLICATIONS

This is a continuation of U.S. application Ser. No. 14/406,189, filed Dec. 5, 2014, which the U.S. National Stage of PCT/US2013/030995, filed on Mar. 13, 2013, which claims the benefit of U.S. Provisional Application No. 61/657,423, filed Jun. 8, 2012, all of which are herein incorporated by reference in their entirety.

ACKNOWLEDGMENT OF GOVERNMENT SUPPORT

This invention was made with government support under Grant Nos. HL116472, HL068135, HL081784, HL096376, HL098174, and HL097376 awarded by the National Institutes of Health. The government has certain rights in the invention.

BACKGROUND

Inflammatory disorders underlie numerous human diseases characterized by a highly activated immune system that leads to secretion of large amounts of circulating pro-inflammatory cytokines after infection with virulent pathogens, in response to host cell injury, or related irritants that activate receptors on immune effector cells (T-cells, macrophages, etc.). For example, sepsis results in over 500,000 deaths in the US each year and pneumonia is the leading cause of death from infections. Further, noninfectious illnesses (colitis, arthritis) can also involve cytokines as major mediators of disease pathogenesis. A central feature of these infectious disorders is the burst in cytokine release, i.e. cytokine storm, from pro-inflammatory cells including macrophages, lymphocytes, and PMNs. Under many conditions, the cytokine storm is exaggerated (hypercytokinemia) and results in a fatal immune reaction with constant activation of immune effector cells that produce sustained and supraphysiologic levels of cytokines including TNFα, IL-β, and IL-6 that leads to profound tissue injury. Left, unchecked, this profound inflammatory cascade can have devastating consequences for the host.

Prior efforts on blocking the cytokine storm has focused on the use of systemic corticosteroids or the development of targeted anti-inflammatory agents to specific cytokines, e.g. TNFα and IL-β that have not improved mortality in sepsis. Other approaches focusing on inhibiting upstream surface receptors within T-cells (e.g. TLR4 receptor) have been inconclusive and similar agents have not succeeded in Phase 3 clinical trials. Many of these approaches are limited as only one target (a receptor or cytokine) is selected for inhibition; however, systematic inflammation and sepsis are intricate disorders whereby a multitude of inflammatory mediators are released from activation of multiple receptors. Agents that are directed against a single molecular target cannot prevent activities of other pro-inflammatory cytokines during the host inflammatory response. These observations underscore the importance of identifying newer targets for intervention that might govern the synthesis and secretion of a wider array of pro-inflammatory biomolecules. Further, the mainstay of therapies for sepsis is antimicrobial agents that do not provide total protection and are limited because of attendant toxicities and the rapid emergence of multi-drug resistance. Thus, the discovery of newer small molecule anti-inflammatory therapeutics with novel targets could have a profound impact on the severity of inflammatory illness such as sepsis.

TNF receptor associated factors (TRAFs) are a family of proteins primarily involved in the regulation of inflammation, antiviral responses, and apoptosis. Six well-characterized TRAF proteins (TRAF1-6) exist and a newer homologue TRAF7 was recently identified. All TRAF members share a highly conserved C-terminal domain that mediates interactions with transmembrane TNF receptors. Identification of TRAF proteins has contributed significantly to the elucidation of the molecular mechanisms of signal transduction emanating from the TNFR superfamily and the Toll like/interleukin-1 receptor (TLR/IL-1R) family. TRAF family proteins interact with the IL-1 receptor, TLRs, CD40, RANK, I-TAC, p75 NGF receptor, etc. Specifically, TRAF2, TRAF5, and TRAF6 serve as adapter proteins that link cell surface receptors with downstream kinase cascades, which in turn activate key transcription factors, such as nuclear factor κB (NFκB), resulting in cytokine gene expression. With an exaggerated immune response, TRAF-mediated cytokine release leads to profound effects of edema, multiorgan failure and shock. The TRAF proteins, however, have a central role as they mediate signal transduction to elicit transcriptional activation of several downstream cytokines. These findings suggest that maneuvers designed to selectively modulate the abundance of TRAF proteins might serve as a novel strategy for therapeutic intervention. However, to date, very little is known regarding the molecular regulation of the TRAF family at the level of protein stability. Strategies directed at modulation of TRAF protein concentrations in cells might serve as the basis for the design of a new class of anti-inflammatory agents.

Ubiquitination of proteins brands them for degradation, either by the proteasome or via the lysosome, and regulates diverse processes. The conjugation of ubiquitin to a target protein is orchestrated by a series of enzymatic reactions involving an E1 ubiquitin-activating enzyme, ubiquitin transfer from an E1-activating enzyme to an E2-conjugating enzyme, and last, generation of an isopeptide bond between the substrate's ε-amino lysine and the c-terminus of ubiquitin catalyzed by a E3-ubiquitin ligase. Of the many E3 ligases, the Skp-Cullin1-F box (SCF) superfamily is among the most studied. The SCF complex has a catalytic core complex consisting of Skp1, Cullin1, and the E2 ubiquitin-conjugating (Ubc) enzyme. The SCF complex also contains an adaptor receptor subunit, termed F-box protein, that targets hundreds of substrates through phosphospecific domain interactions. F-box proteins have two domains: an NH2-terminal F-box motif and a C-terminal leucine-rich repeat (LRR) motif or WD repeat motif. The SCF complex uses the F-box motif to bind Skp1, whereas the leucine-rich/WD repeat motif is used for substrate recognition.

SUMMARY

One embodiment disclosed herein is a compound, or a pharmaceutically acceptable salt or ester thereof, having a structure of formula II:

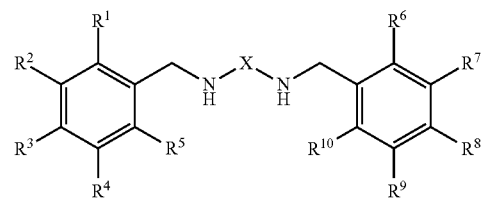

wherein X is a divalent linking moiety; and
$R^1$-$R^{10}$ are each individually H, optionally-substituted alkyl, optionally-substituted alkoxy, optionally-substituted aryl, optionally-substituted cycloalkyl, optionally-substituted heterocyclic, halogen, amino, or hydroxy, provided that at least one of $R^3$ or $R^8$ is an optionally-substituted alkyl, a substituted alkoxy, optionally-substituted aryl, optionally-substituted cycloalkyl, optionally-substituted heterocyclic, or halogen.

Further disclosed herein is a compound, or a pharmaceutically acceptable salt or ester thereof, having a structure of formula III:

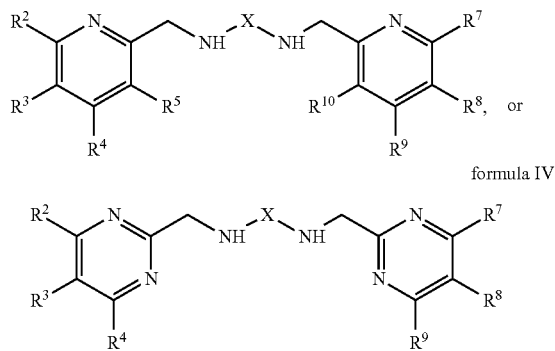

formula IV wherein X is a divalent linking moiety; and $R^2$-$R^5$ and $R^7$-$R^{10}$ are each individually H, optionally-substituted alkyl, optionally-substituted alkoxy, optionally-substituted aryl, optionally-substituted cycloalkyl, optionally-substituted heterocyclic, halogen, amino, or hydroxy.

Another embodiment disclosed herein is a method for inhibiting pro-inflammatory cytokine release in a subject, comprising administering to the subject an FBXO3 inhibitor.

A further embodiment disclosed herein is a method for treating an inflammatory disorder in a subject, comprising administering to the subject a therapeutically effective amount of an FBXO3 inhibitor.

An additional embodiment disclosed herein is a method for inhibiting FBXO3-induced ubiquitination and degradation of FBXL2, comprising contacting FBXO3-containing tissue or cells with a benzathine compound, an optionally-substituted diaminoalkane, a substituted quinoline, haematoxylin, tetramethylenebis, naphthacaine, ampicillin, or elliptine.

Another embodiment disclosed herein is a method for inhibiting bacterial growth in a subject or a surface of an object, comprising administering to the subject or the surface of the object an effective amount of an FBXO3 inhibitor.

A further embodiment disclosed herein is a method for inhibiting a bioactivity of FBXO3 protein, comprising contacting FBXO3 with a compound that interacts with amino acid residues Y308, N335, E341, T368 and S370 that are present in an ApaG domain cavity of the FBXO3 protein.

The foregoing and will become more apparent from the following detailed description, which proceeds with reference to the accompanying figures.

BRIEF DESCRIPTION OF THE DRAWINGS

FIGS. 1A-1E. FBXL2 targets TRAFs for polyubiquitination.

FIG. 1A. Immunoblotting showing levels of TRAFs and negative control proteins, after control (CON) plasmid or ectopic FBXL2 plasmid expression. FIG. 1B. Cells were transfected with an inducible FBXL2 plasmid under control of exogenous doxycycline. Cells were treated with doxycycline for various times, cells were then collected and cell lysates were analyzed for FBXL2, TRAFs, and β-actin by immunoblotting. FIG. 1C. Endogenous FBXL2 was immunoprecipitated and followed by TRAF 1-6 immunoblotting. FIG. 1D. In vitro ubiquitination assays. Purified SCF complex components were incubated with individual V5-TRAFs and the full complement of ubiquitination reaction components (second lane from left) showing polyubiquitinated TRAF proteins. FIG. 1E. Half-life of each TRAF protein with or without FBXL2 overexpression is shown.

FIGS. 2A-2D. FBXL2 is polyubiquitinated at the Lysine 201 site. FIGS. 2A-C. Several deletion (FIGS. 2A, 2B) and point (FIG. 2C) mutants of FBXL2 were designed and cloned into a pcDNA3.1D/V5-HIS vector (upper panel). Plasmids encoding FBXL2 mutants were transfected into cells followed by MG132 treatment. Cells were collected and cell lysates were analyzed for V5-FBXL2 and β-actin by immunoblotting after exposure of cells to vehicle (lower left) or to MG132 (lower right). FIG. 2D. Half-life studies of wild-type (WT) FBXL2 and FBXL2 K201R.

FIGS. 3A-3K. FBXL2 is phosphorylated and targeted by the SCF E3 ligase FBXO3 at residue T404. FIG. 3A. Scheme of potential phosphorylation sites within FBXL2 (GPS2.1 prediction). FIG. 3B. Endogenous FBXL2 was immunoprecipitated and followed by phospho-threonine immunoblotting. FIG. 3C. Endogenous FBXL2 was immunoprecipitated and followed by immunoblotting for several candidate kinases. FIG. 3D. Endogenous FBXL2 was immunoprecipitated and followed by FBXO3 immunoblotting. FIG. 3E. In vitro ubiquitination assays. Purified SCFFBXO3 complex components were incubated with V5-FBXL2 and the full complement of ubiquitination reaction components (right lane) showing polyubiquitinated FBXL2. FIG. 3F. Cells were transfected with his tagged FBXL2 deletion mutant plasmids, followed by his-pull down; FBXO3 protein bound to the cobalt beads was eluted and then resolved in SDS-PAGE followed by FBXO3 immunoblotting. FIG. 3G. Half-life studies of WT FBXL2 and FBXL2 C-terminal deletion mutants. FIG. 3H. GSK3β consensus sequence within FBXL2. FIG. 3I. Cells were transfected with plasmids encoding either V5-WT FBXL2 or V5-FBXL2 T404A point mutants, transfected cells were then subjected to immunoprecipitation with V5 antibody followed by phospho-threonine immunoblotting. FIG. 3J. In vitro ubiquitination assays. Purified SCFFBXO3 complex components were incubated with V5 tagged WT FBXL2 or the FBXL2 T404A mutant and the full complement of ubiquitination reaction components showing polyubiquitinated FBXL2 (second lane from left). FIG. 3K. Model of FBXO3 targeting FBXL2.

FIGS. 4A-4F. FBXO3 contains a natural occurring mutation at V220.

FIG. 4A. SNP analysis of FBXL2 protein indicating a V220I mutation. FIG. 4B. Genomic DNA was first extracted from PBMC cells from twenty healthy Caucasian donors followed by SNP genotyping using a TaqMan® SNP probe with real-time PCR. FIG. 4C. Three WT PBMC cells samples and three PBMC cells containing the heterozygous V220I mutation were treated with 2 ug/ml of LPS for 24 h before assays for cytokine release using a human cytokine array (R&D). FIG. 4D. In vitro ubiquitination assays. Purified SCFFBXO3 or SCFFBXO3V220I mutant complex components were incubated with V5-FBXL2 and the full complement of ubiquitination reaction components showing levels of polyubiquitinated FBXL2. FIG. 4E. Cells were transfected with V5-WT FBXO3 or the V5-FBXO3V220I mutant plasmids, followed by immunoblotting for V5, FBXL2, and TRAF proteins. FIG. 4F. U937 cells were treated with LPS for an additional 24 h before assaying for cytokine secretion using a human cytokine array (R&D).

FIGS. 5A-5I. FBXO3V220I is a loss-of-function mutant of FBXO3 in vivo. Lentiviral FBXO3 gene transfer augments the severity of *P. aeruginosa*-induced lung inflammation and injury. C57BL/6J mice were administered intratracheal (i.t.) Lenti-LacZ, Lenti-FBXO3 or Lenti-FBXO3V220I (107 CFU/mouse) for 120 h, and 4 mice/group were inoculated with *P. aeruginosa* (PA103, 104 PFU/mouse) for 24 h. Mice were monitored on a FlexiVent to measure lung mechanics (FIGS. 5A-5D). Mice were then sacrificed and lungs were lavaged with saline, harvested, and then homogenized; lavage protein, cell counts, and cytokine secretion were determined in (FIGS. 5E-5F, 5I). FIG. 5G. H&E staining was performed on lung samples in (FIG. 5A). FIG. 5H. Survival studies of mice administered i.t. PA103 (105 PFU/mouse, 7 mice per group) was determined Mice were carefully monitored over time; moribund, preterminal animals were immediately euthanized and recorded as deceased. Kaplan-Meier survival curves were generated using Prism software.

FIGS. 6A-6I. FBXO3 knockdown ameliorates *pseudomonas* induced lung injury. Lentiviral FBXO3 knockdown attenuates the severity of *P. aeruginosa*-induced lung inflammation and injury. C57BL/6J mice were administered i.t. Lentivirus encoding control (CON) shRNA or Lenti-FBXO3 shRNA (107 CFU/mouse) for 120 h, and 4 mice/group were inoculated with PA103 (104 PFU/mouse) for 24 h. Mice were monitored on FlexiVent to measure lung mechanics (FIGS. 6A-6D). Mice were then sacrificed and lungs were lavaged with saline, harvested, and then homogenized. Lavage protein, cell counts, and cytokine secretion, were measured in (FIGS. 6E, 6F, 6H). FIG. 6G. H&E staining was performed on lung samples in (FIG. 6A). FIG. 6I. Survival study of mice administered i.t. with PA103 (105 PFU/mouse, 6 mice per group) was determined Mice were carefully monitored over time; moribund, preterminal animals were immediately euthanized and recorded as deceased. Kaplan-Meier survival curves were generated using Prism software.

FIG. 7B. In vitro ubiquitination assays. Purified SCFFBXO3 full-length (FL) or truncated FBXO3 proteins were incubated with V5-FBXL2 and the full complement of ubiquitination reaction components showing polyubiquitinated FBXL2 (second lane from left). FIG. 7C. Structural analysis of the FBXO3-ApaG domain FIGS. 7D-7F. Docking study of the candidate compound, benzathine, interacting with the FBXO3-ApaG domain.

FIG. 8A-8D. General theme of synthesizing benzathine analogs. Briefly, the target benzathine analogs were prepared from benzaldehyde derivatives and diamine derivatives such as ethylenediamine. In general, the relevant benzaldehyde derivatives (0.02 mol) were added to a solution of ethylenediamine (0.01 mol, ~700 ul) in anhydrous ethanol (20 ml). The resulting solution was refluxed and stirred for 60 min until the precipitation of the relevant Schiff base. The Schiff bases were filtered and washed with cold ethanol. The Schiff base was then added to 30 ml absolute methanol. A 10% solution of sodium borohydride (0.02 mol) was dissolved in absolute methanol and added to the Schiff base. When the addition was complete, the reaction solution was refluxed for an additional 15 min Solvent was then removed through rotary evaporation and 40 ml cold water was added to liberate the secondary amine. The precipitation of benzathine derivatives were collected, washed with water and dried, followed by recrystallization from ethyl acetate. FIGS. 8B-8D. Structure and docking studies of the novel FBXO3 inhibitor, BC-1215.

FIG. 9. BC-1215 inhibits a broad spectrum of Th1 panel cytokines.

PBMC cells (0.6 ml at $1.5*10^6$/ml) were treated with 2 ug/ml LPS for 16 hrs with BC-1215 at 10 ug/ml. Cytokine release was monitored by the human cytokine array (R&D systems). The results from cytokine array dot blot were quantitated and graphed in below.

FIGS. 10A-10E. BC-1215 inhibits FBXO3 and decreases TRAF protein levels.

Figure 10D:
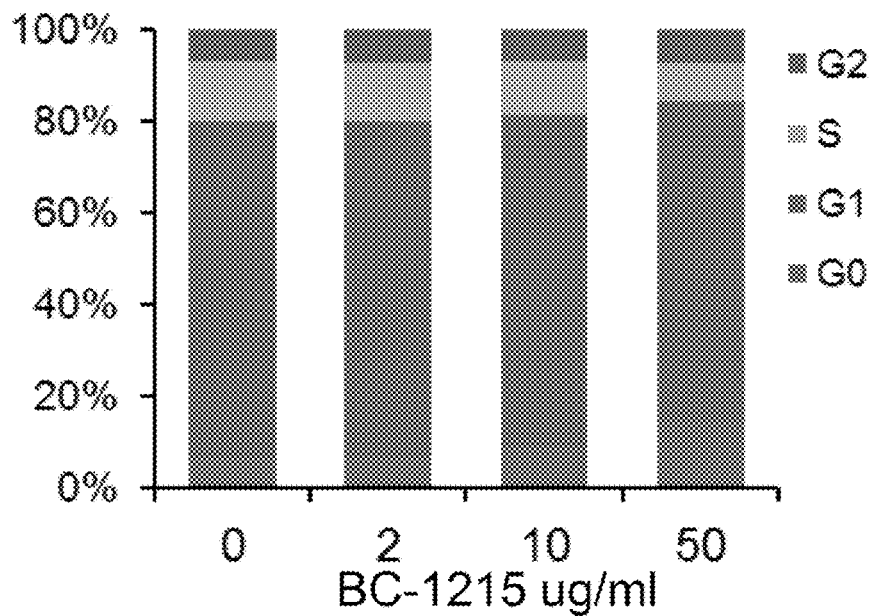
Figure 10E:
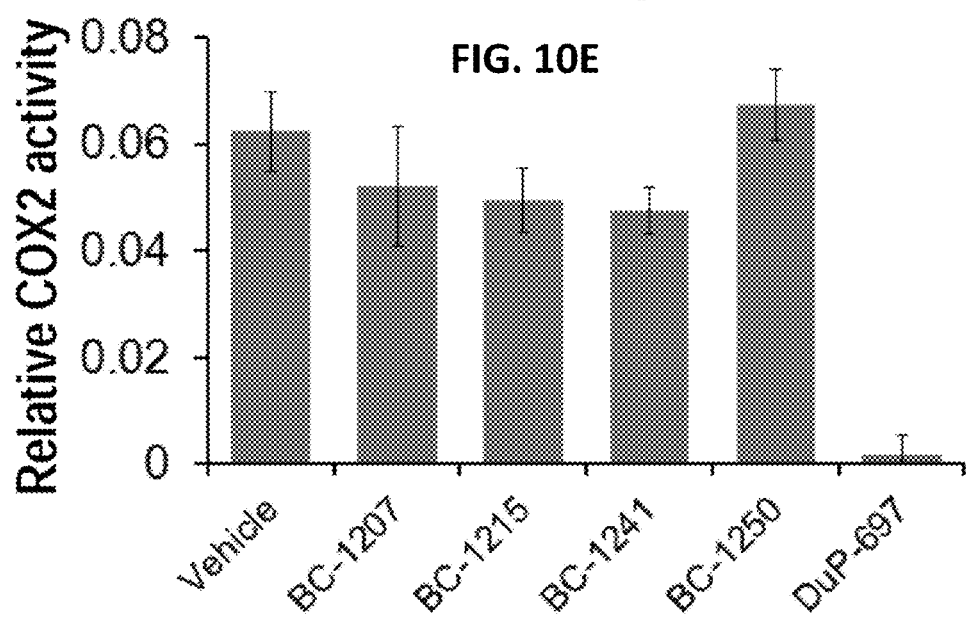

FIG. 10A. PBMC cells were treated with 2 ug/ml of LPS at each time point before immunoblotting for indicated proteins. FIG. 10B. In vitro ubiquitination assays. Purified SCFFBXO3 complex components was incubated with V5-FBXL2 and the full complement of ubiquitination reaction components with increased concentration of BC-1215 showing decreased levels of polyubiquitinated FBXL2. FIG. 10C. MLE cells were also treated with BC-1215 at different concentrations for 16 h. Cells were collected and assayed for immunoblotting. FIG. 10D. Hela cells were treated with BC-1215 at different concentrations for 24 h before cell cycle analysis (BD bioscience). FIG. 10E. MLE cells were treated with BC-1215 (10 ug/ml) for 24 h before assaying for COX-2 activity (Cayman)

Figure 11:
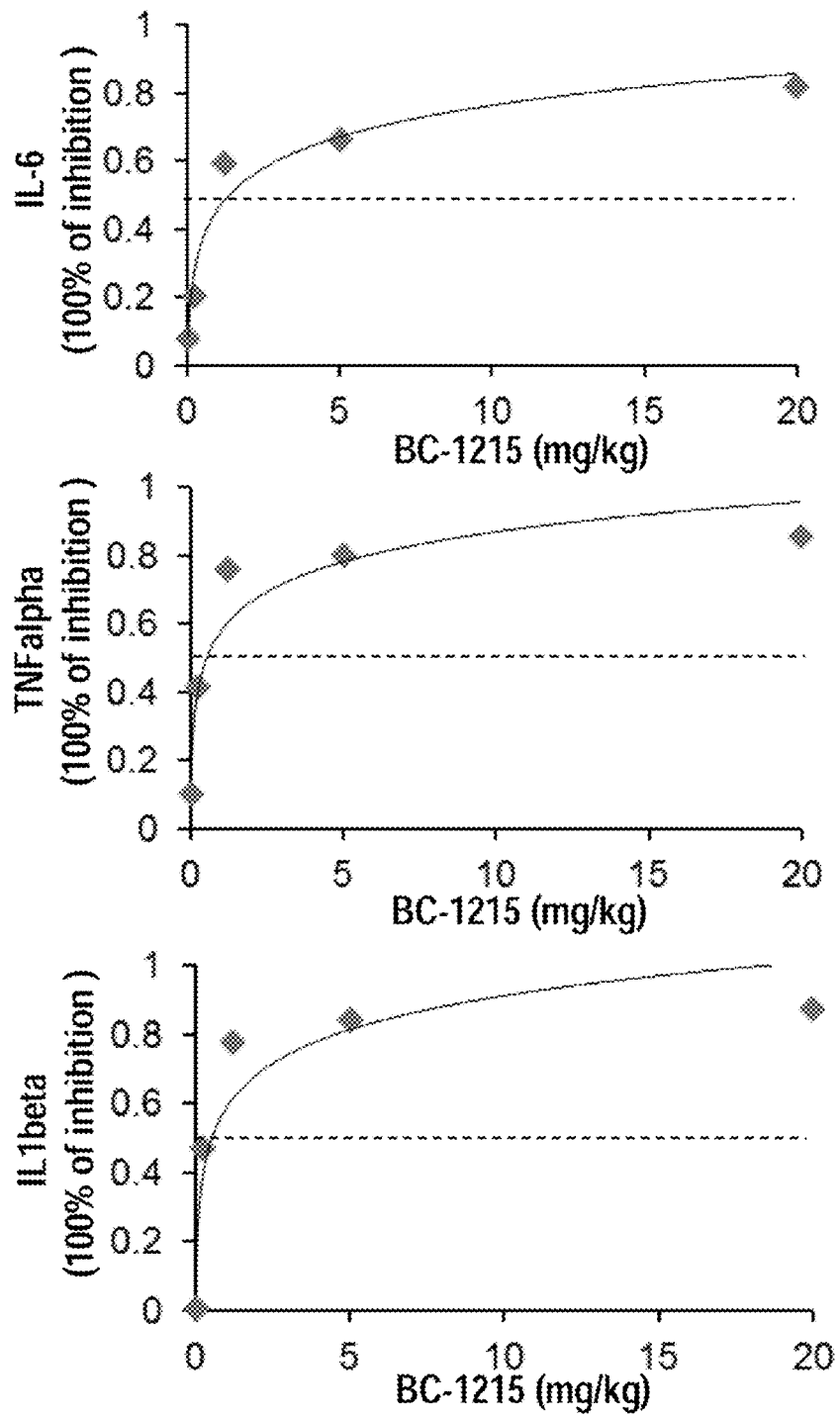

FIG. 11. BC-1215 inhibits cytokine release from in an endotoxin septic shock model. BC-1215 was solubilized in water using acetic acid in a 1:2 molar ratio; the stock solution of BC-1215 was 5 mg/ml. C57BL6 mice were deeply anesthetized with ketamine (80-100 mg/kg intraperitoneally (i.p.) and xylazine (10 mg/kg i.p.). 500 ug, 100 ug, 20 ug, 4 ug and 0.8 ug of BC-1215 was administered to mice through an intraperitoneal (IP) injection. 10 min later, mice were given 100 ug of LPS (*E. coli*) through an IP injection. 90 min later, mice were euthanized; blood was collected and tested for IL1-β, IL-6 and TNFα assays. (n=3/mice group at each dose)

Figure 12:
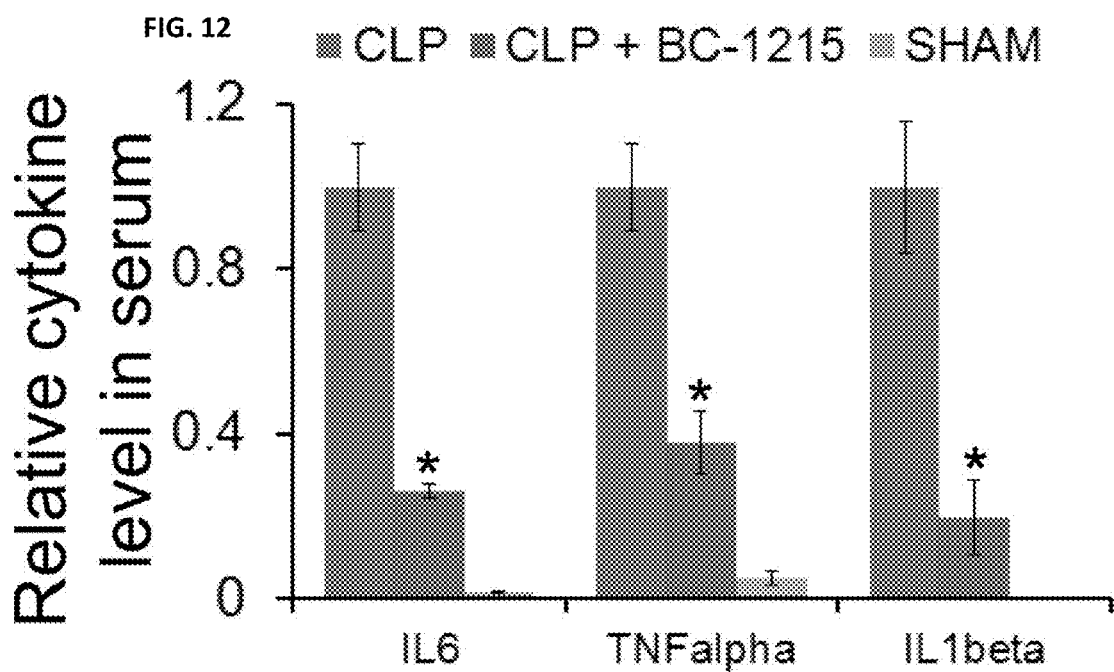

FIG. 12. BC-1215 inhibits cytokines release in a cecal ligation and puncture (CLP) sepsis model. BC-1215 was solubilized as above. C57BL6 mice were deeply anesthetized with ketamine (80-100 mg/kg IP and xylazine (10 mg/kg i.p.). 100 ug of BC-1215 was administered to mice though an IP injection. 30 min later, CLP was performed. 6 h later, mice were euthanized; blood was collected and assayed for IL1-β, IL-6 and TNFα levels. (n=4-5 mice/group, *p<0.05 versus CLP)

FIGS. 13A-13H. BC-1215 reduces lung injury in *pseudomonas* pneumonia.

Figure 13A:
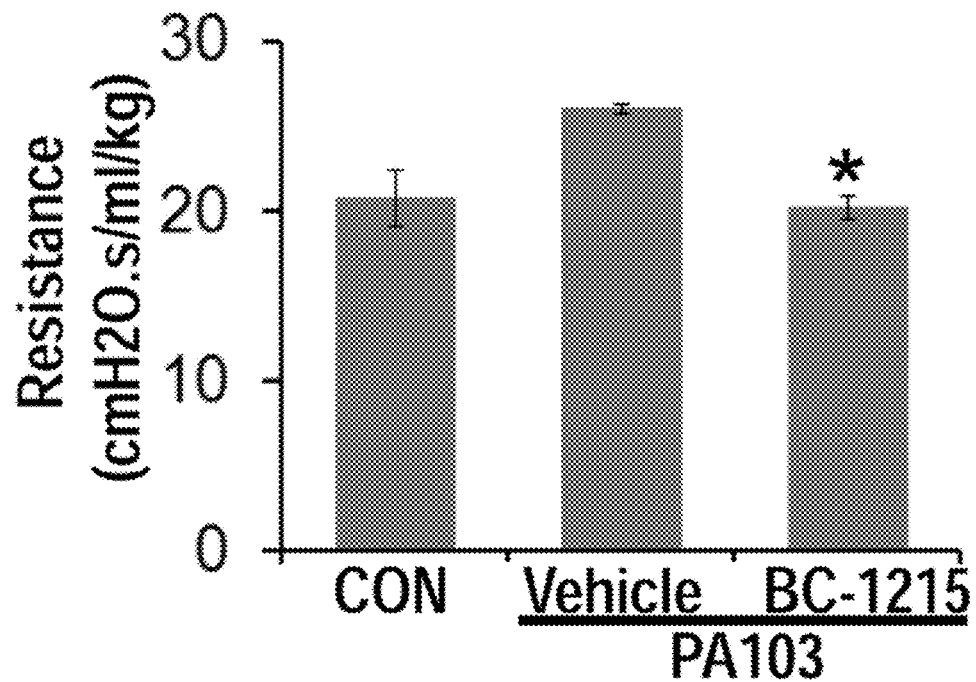
Figure 13B:
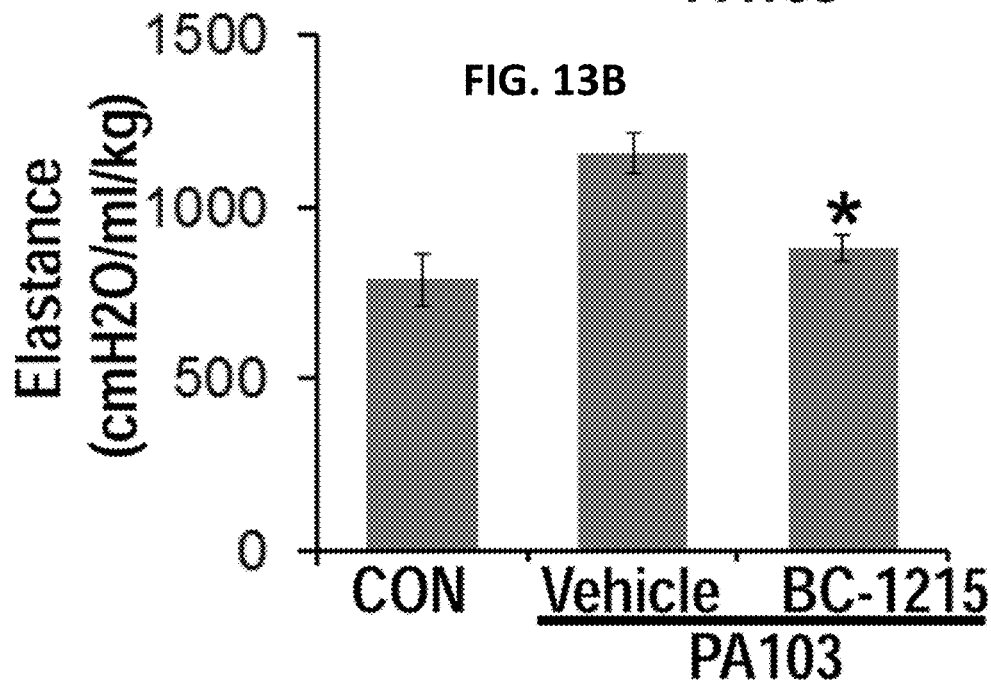
Figure 13C:
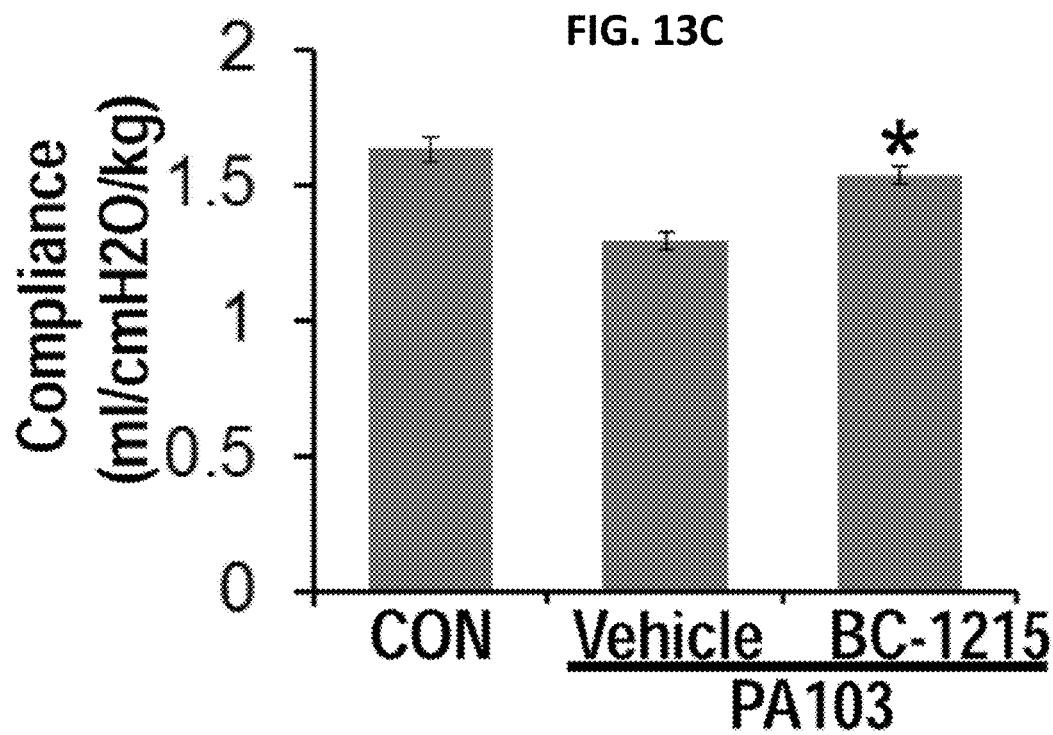
Figure 13D:
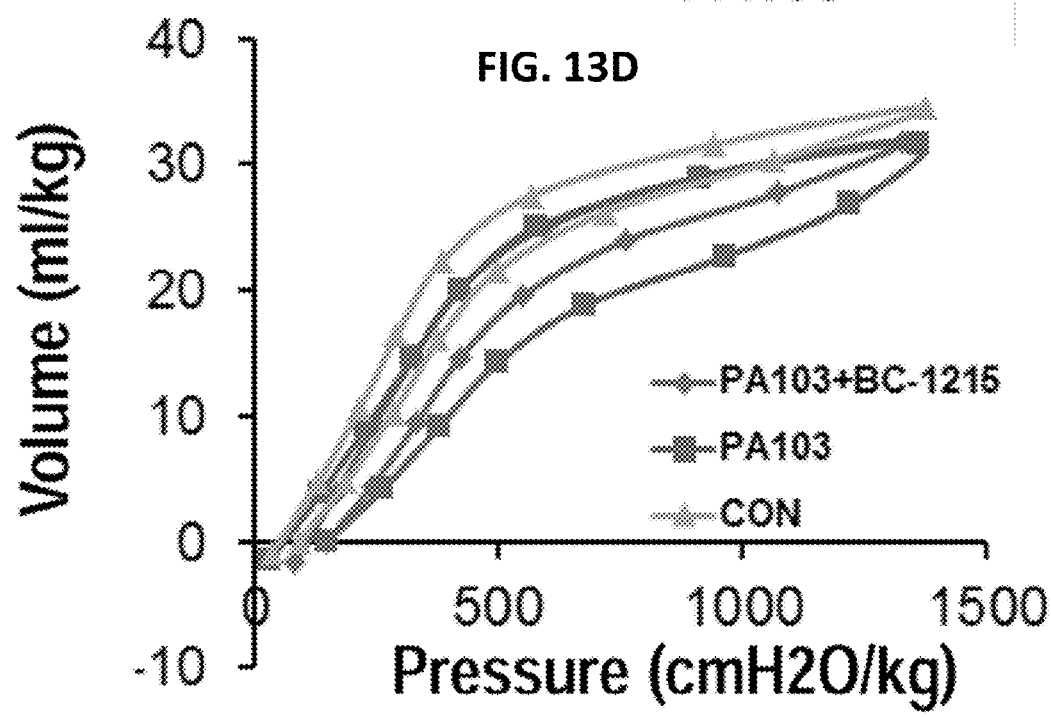
Figure 13G:
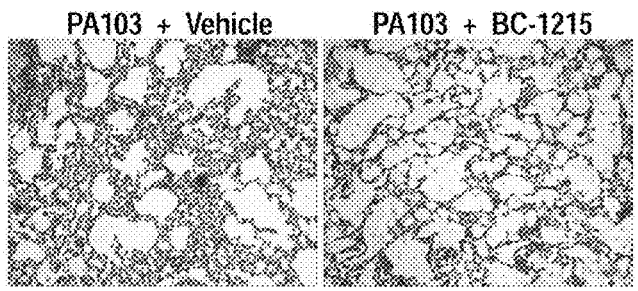
Figure 13H:
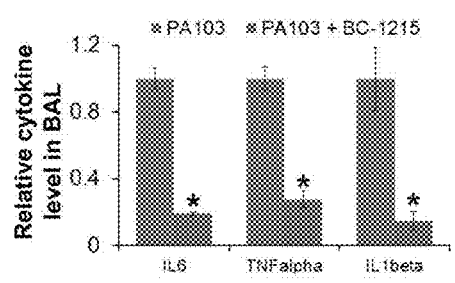

BC-1215 (100 ug) was administered to C57BL6 mice though an IP injection, mice were then challenged with *Pseudomonas* (strain PA103, 104 CFU/mouse, i.t.) for an additional 18 h. Mice were monitored on a FlexiVent to measure lung mechanics (FIGS. 13A-13D). Mice were then sacrificed and lungs were lavaged with saline, harvested, and then homogenized. Lavage protein, cell count and cytokine secretion, was measured in (FIG. 13E, 13F, 13H). FIG. 13G. H&E staining was performed on lung samples. (n=4-6 mice/group, *p<0.05 versus Vehicle)

FIGS. 14A-14H. BC-1215 lessens severity of H1N1 Influenza pneumonia. FIGS. 14A-14D. C57BL6 mice were challenged with H1N1 (106 PFU/mouse, i.t.) for up to 9 d.

Figure 14C:
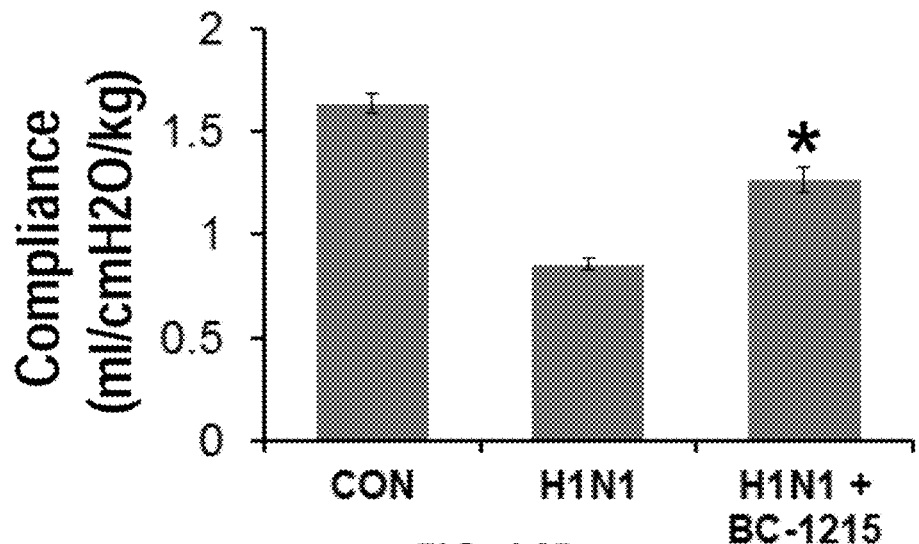
Figure 14D:
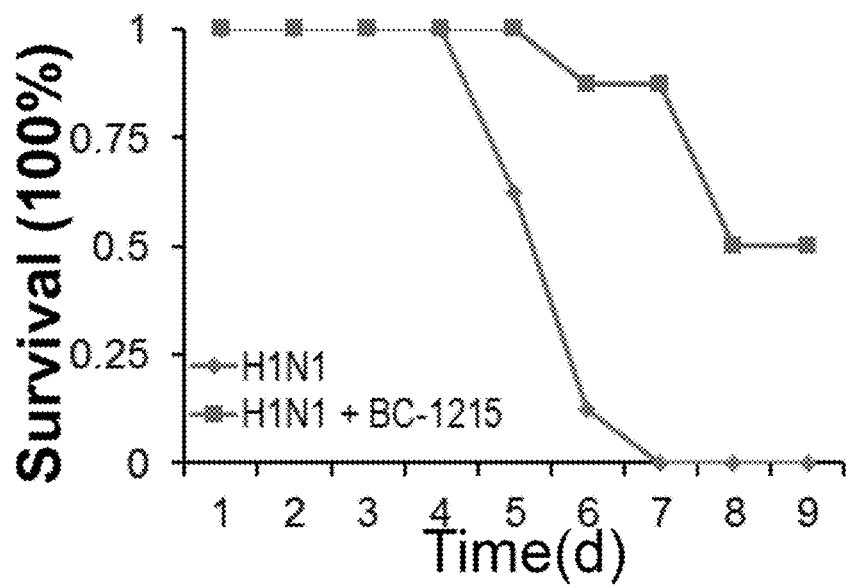
Figure 14E:
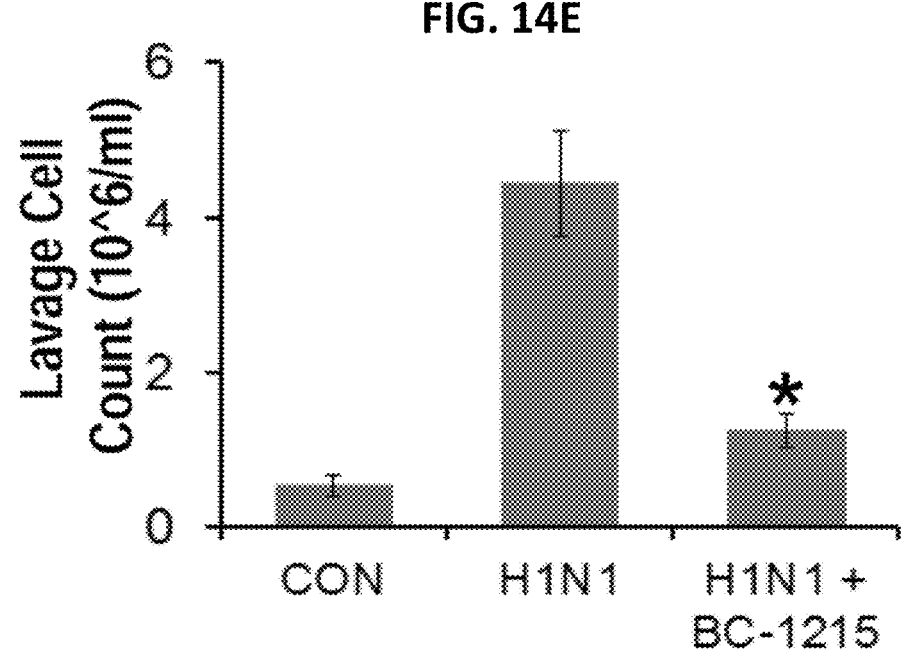
Figure 14F:
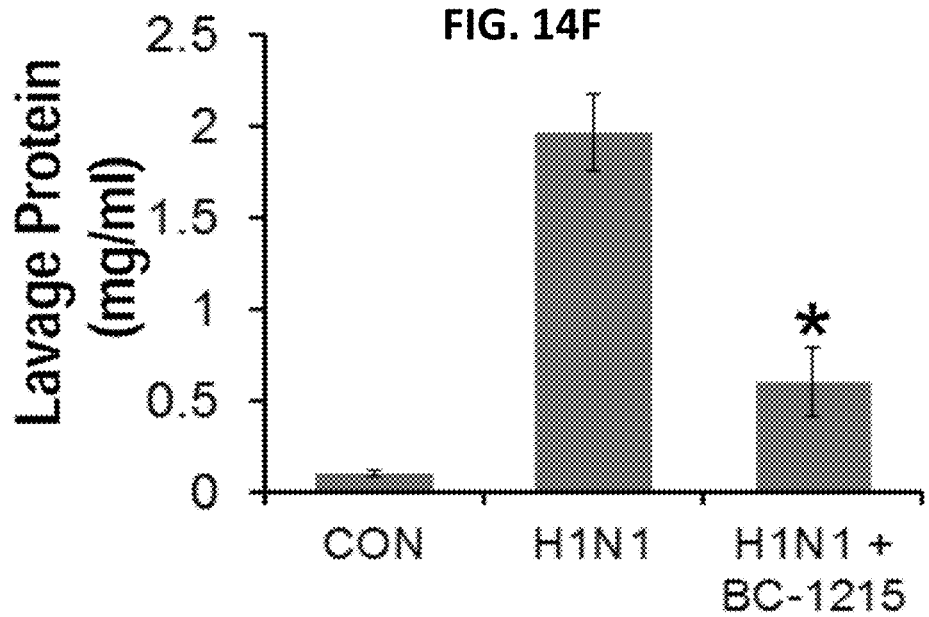

For BC-1215 treatment, a stock solution (5 mg/ml) was added to drinking water (containing 2% sucrose) to the final concentration of 30 ug/ml. Lung mechanics were measured at day 5 using FlexiVent (FIGS. 14A-14C). FIG. 14D. Survival study of mice administered i.t. with H1N1 ($10^5$ PFU/mouse, 8 mice/group). Mice were carefully monitored over time; moribund, preterminal animals were immediately euthanized and recorded as deceased. Mice were then sacrificed and lungs were lavaged with saline, harvested, and then homogenized. Lavage protein, cell count were measured in (FIG. 14E, 14F). FIG. 14G. Photograph of lungs from vehicle or BC-1215 treated mice. FIG. 14H. H&E staining was performed on lung samples. (n=5-8 mice/group, *p<0.05 versus H1N1)

FIGS. 15A-15C. BC-1215 reduces TPA induced ear edema. FIG. 15A-15C. C57BL6 mice were deeply anesthetized with ketamine (80-100 mg/kg i.p.) and xylazine (10 mg/kg i.p.). 20 µl of ethanol solution of BC-1215 was applied to ears at 8, 40, 200 ug/ear 30 min after TPA administration (2 µg/ear). Comparisons included equal volumes of ethanol (vehicle control). 18 h after TPA administration, mice were euthanized; the thickness of the ear was measured using a micrometer (FIG. 15B). Ear punch biopsies were also taken immediately, weighed and graphed (FIG. 15C).

FIGS. 16A-16C. BC-1215 reduces Carrageenan induced paw edema. FIGS. 16A-16C. C57BL6 mice were deeply anesthetized with ketamine (80-100 mg/kg i.p.) and xylazine (10 mg/kg i.p.). Mice were received a subplantar administration of 25 ul of saline or 25 ul of carrageenan (1% in saline), followed by an IP injection of 100 ug of BC-1215 daily for two days. Mice were then euthanized; the thickness and volume of paw was measured (FIG. 16B-16C). (n=4 mice/group, *p<0.05 versus vehicle)

FIGS. 17A-17D. BC-1215 reduces DSS induced colonic inflammation. FIGS. 17A-FIG. 17C. C57BL6 mice were fed with water containing 3.5% dextran sulfate sodium (DSS) for up to five days. Mice were treated with either vehicle or 100 ug of BC-1215 daily (via IP injection). Mice were then euthanized; the length of the colon was measured and graphed in (FIG. 17A). Colonic tissues were also analyzed for IL1β (FIG. 17B) and TNFα (FIG. 17C) by ELISA. (n=4 mice/group, *p<0.05 versus DSS) FIG. 17D, H&E staining was performed on colonic samples. (n=4 mice/group, *p<0.05 versus DSS)

Figure 18:
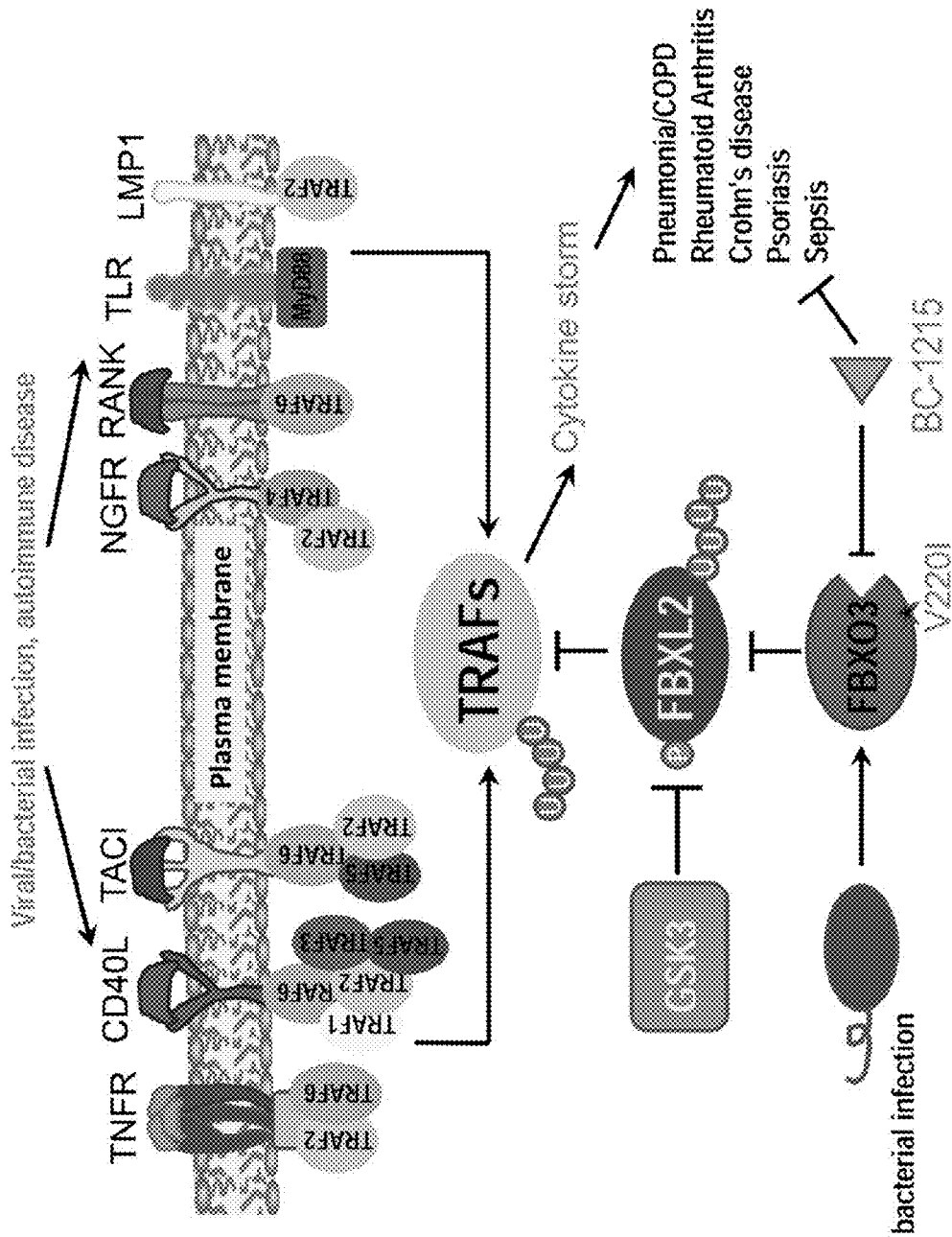
Figure 20B:
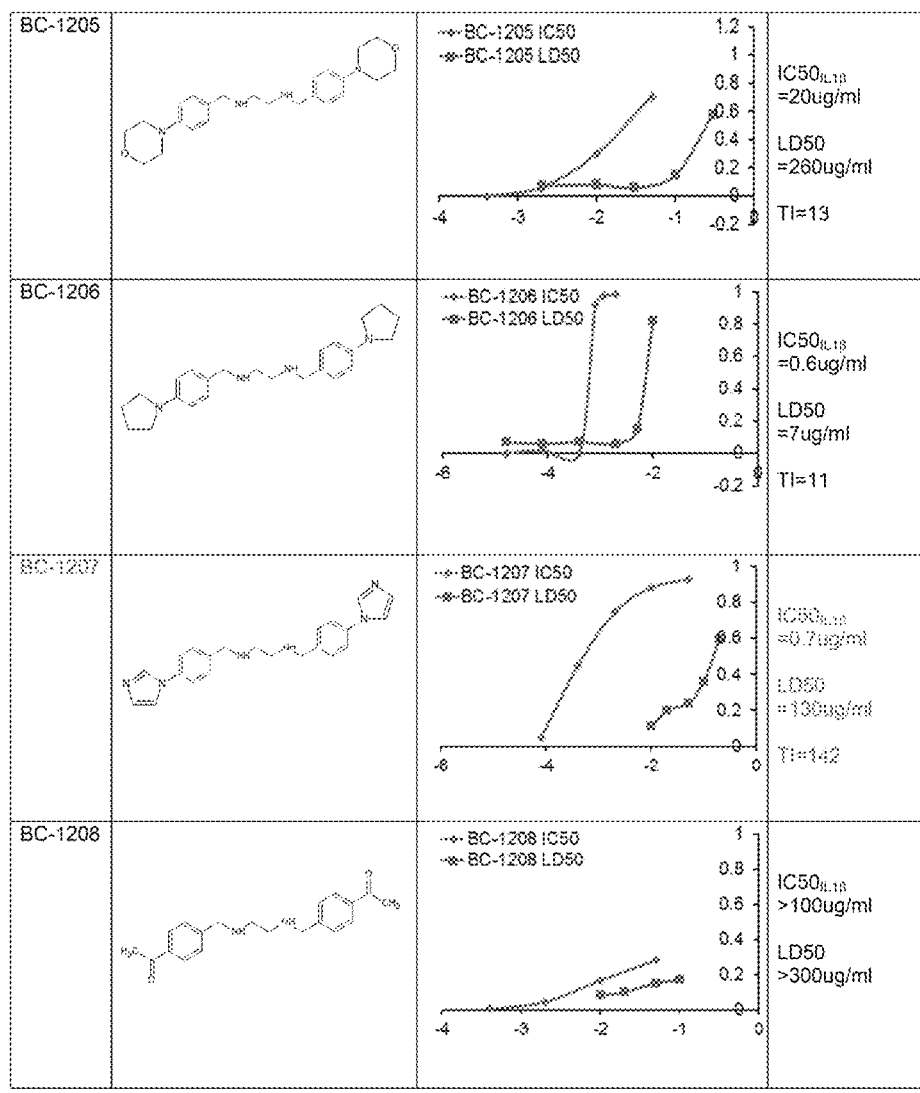
Figure 20C:
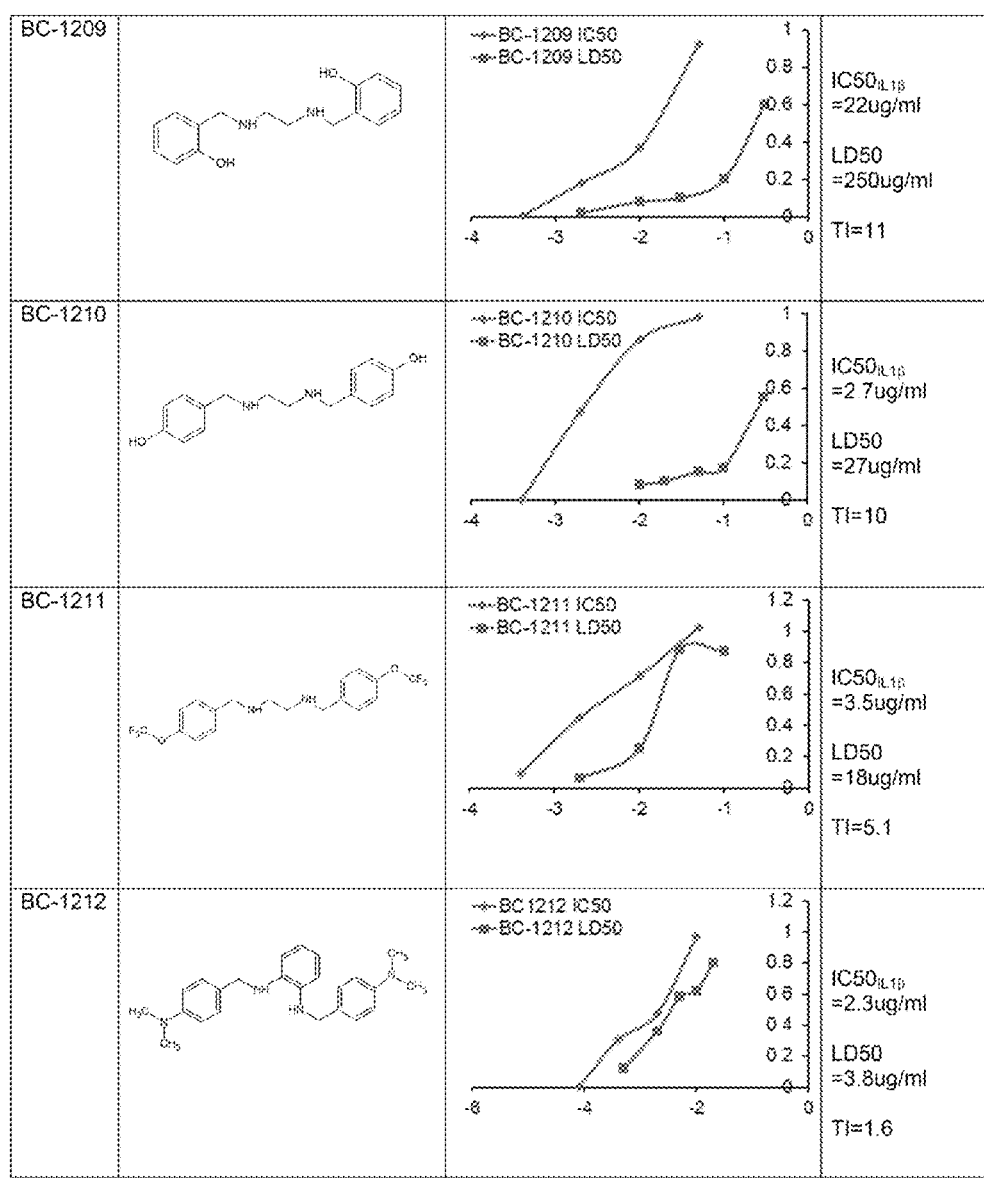
Figure 20D:
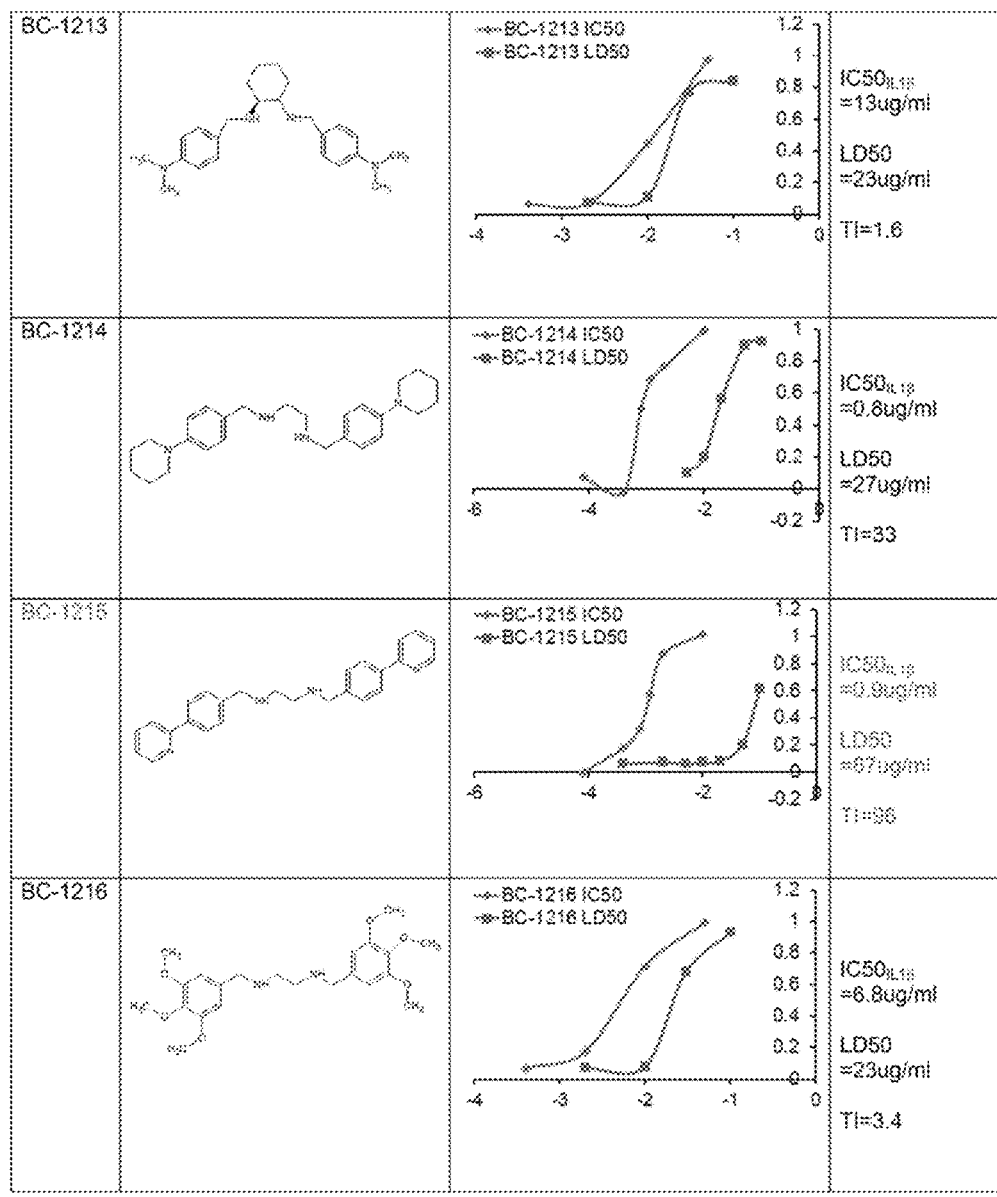
Figure 20E:
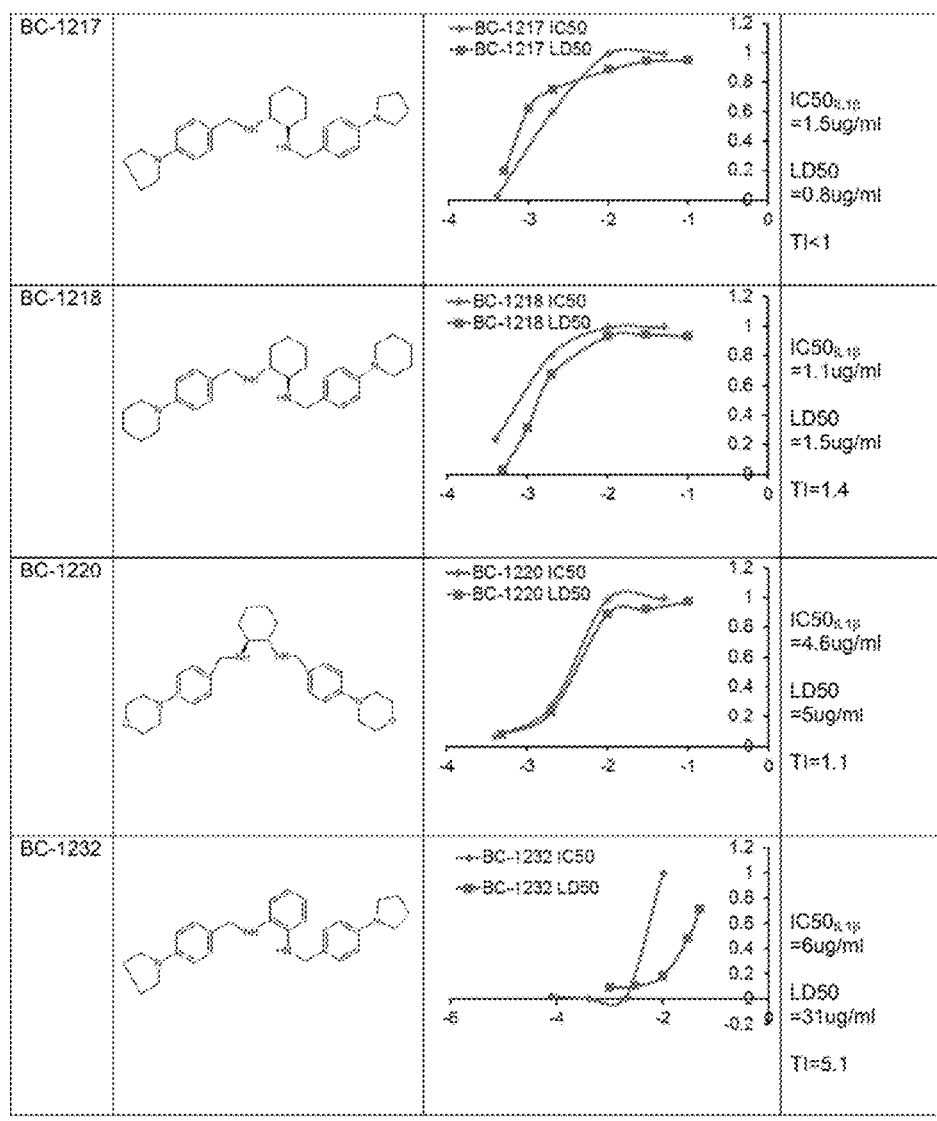
Figure 20F:
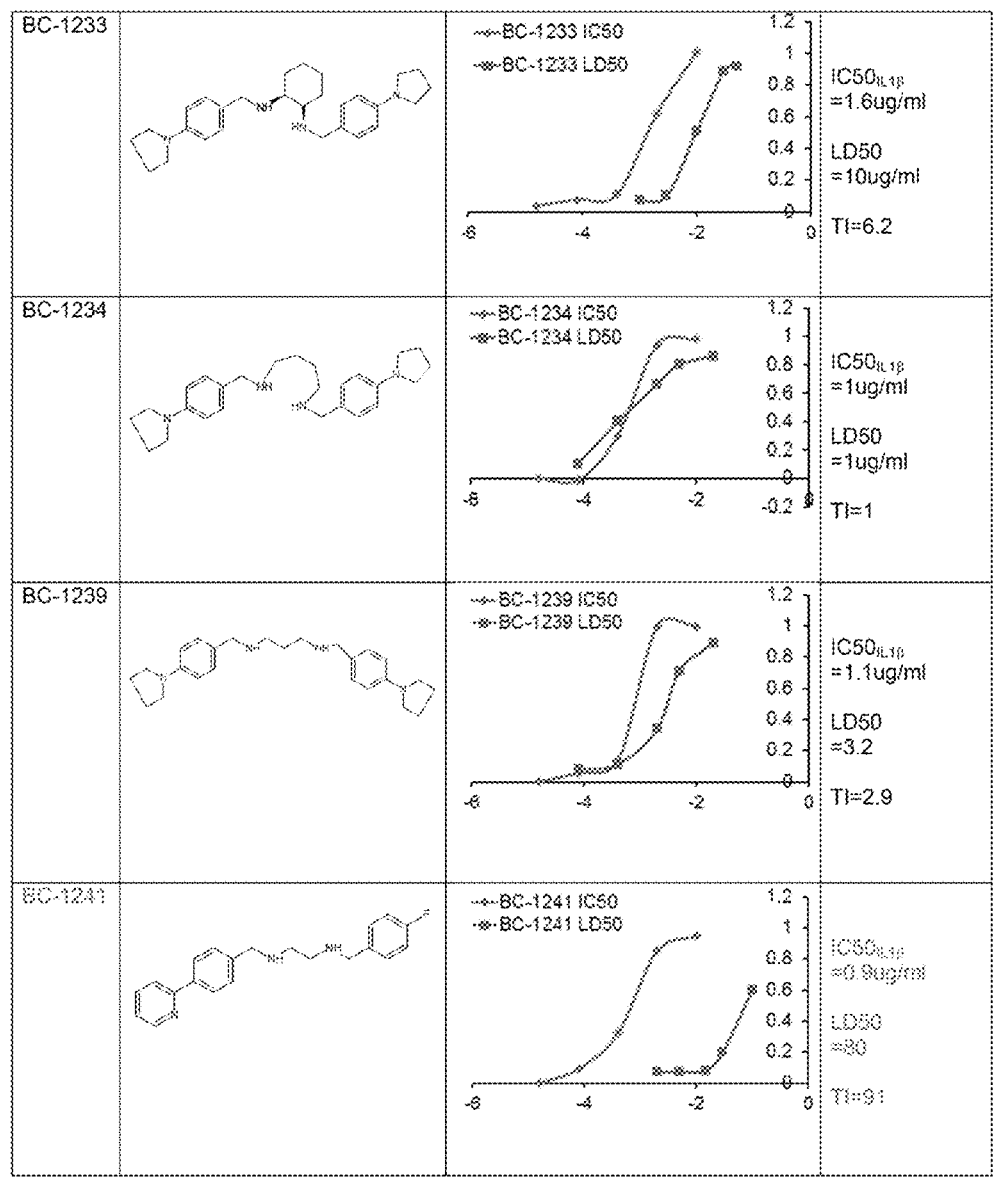
Figure 20G:
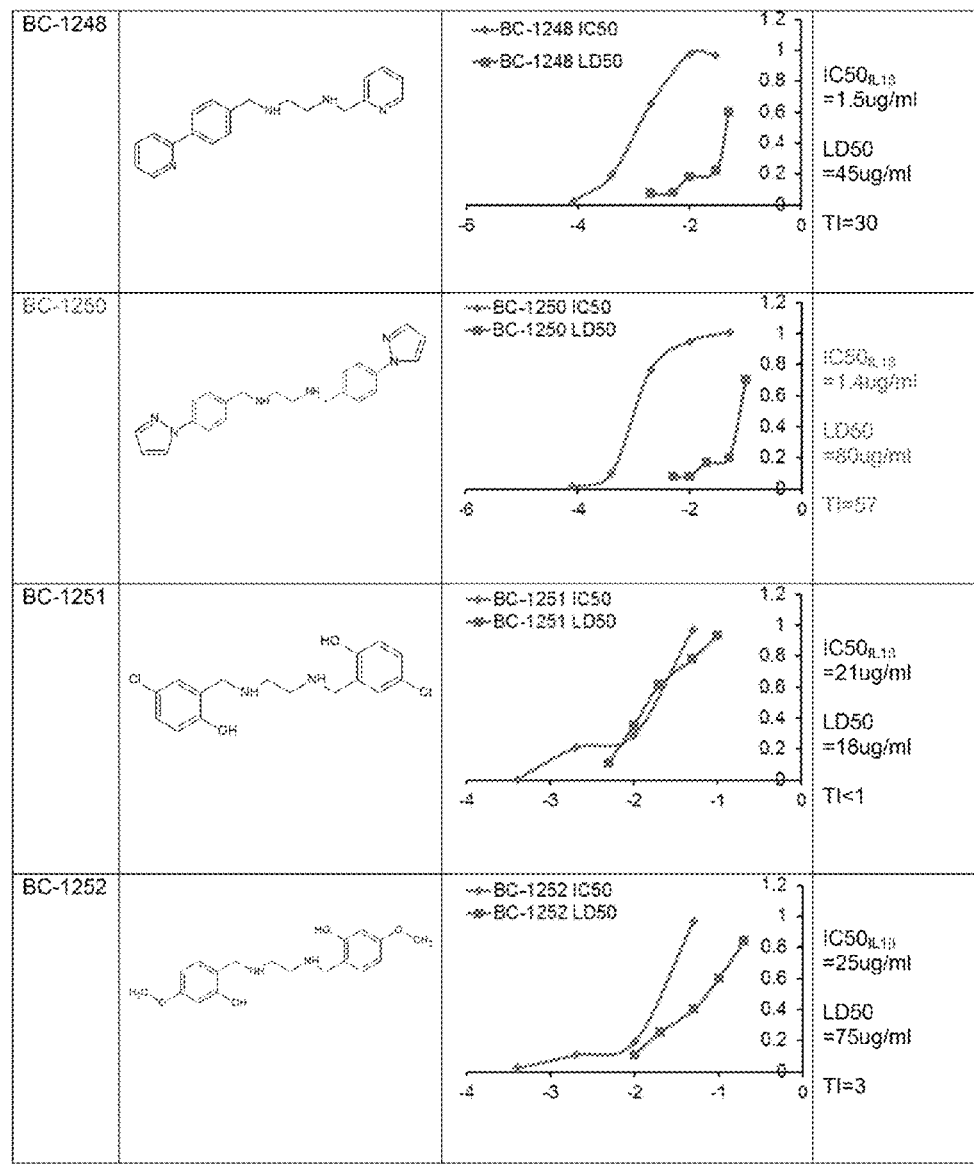
Figure 20H:
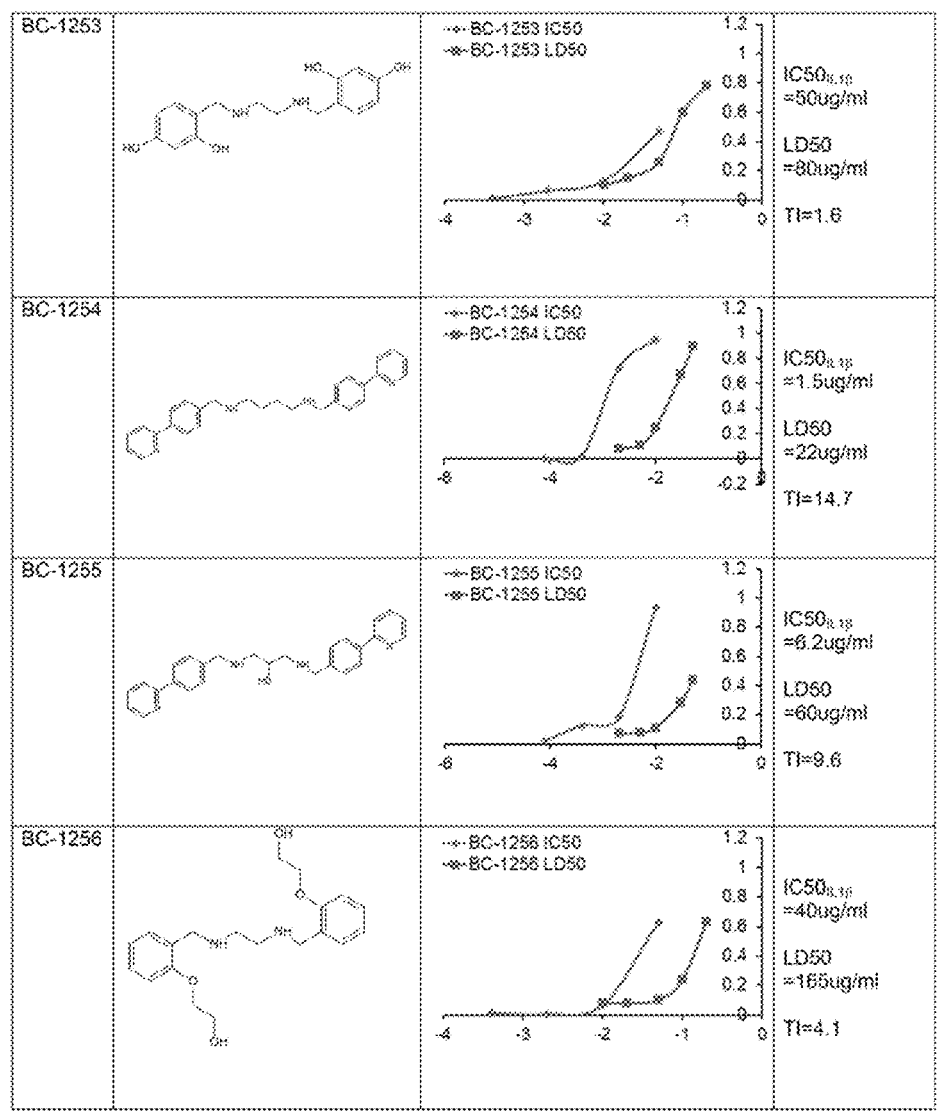
Figure 20I:
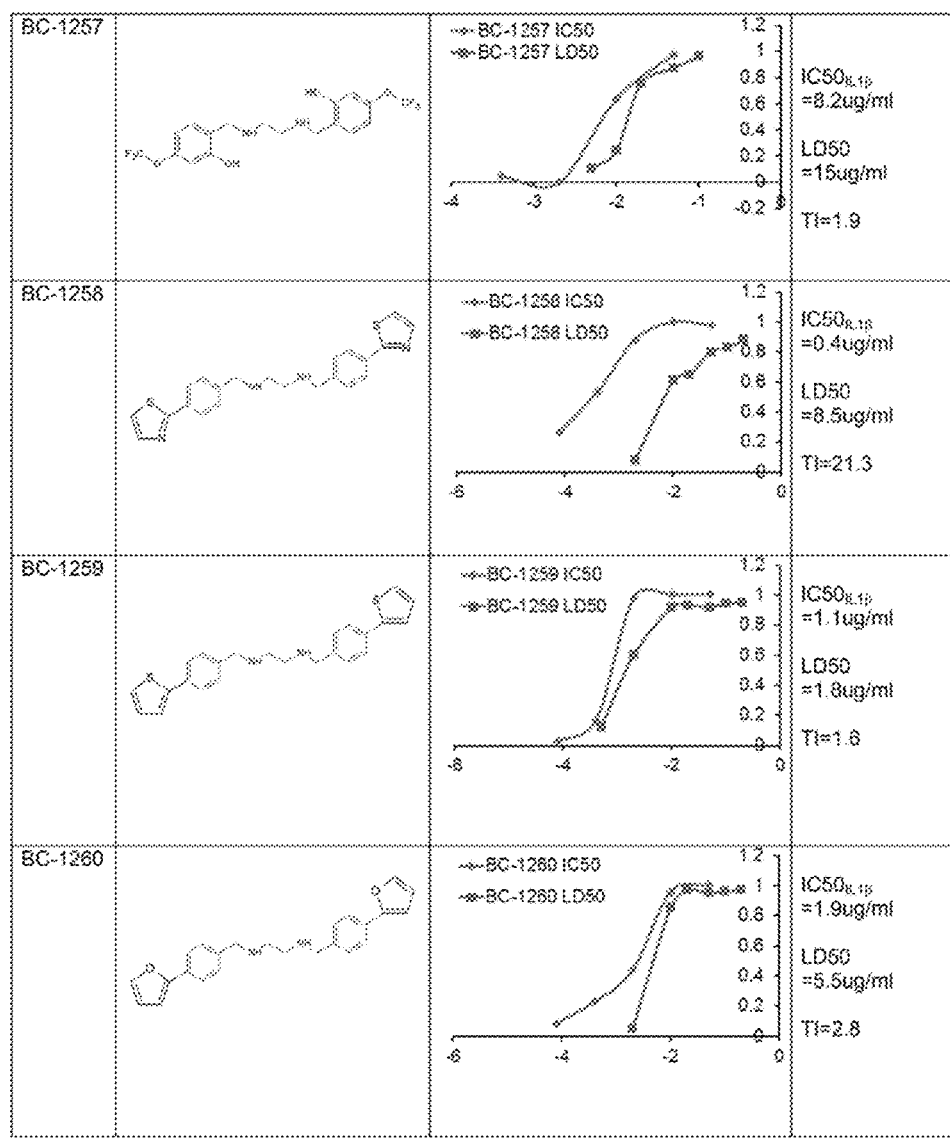
Figure 20J:
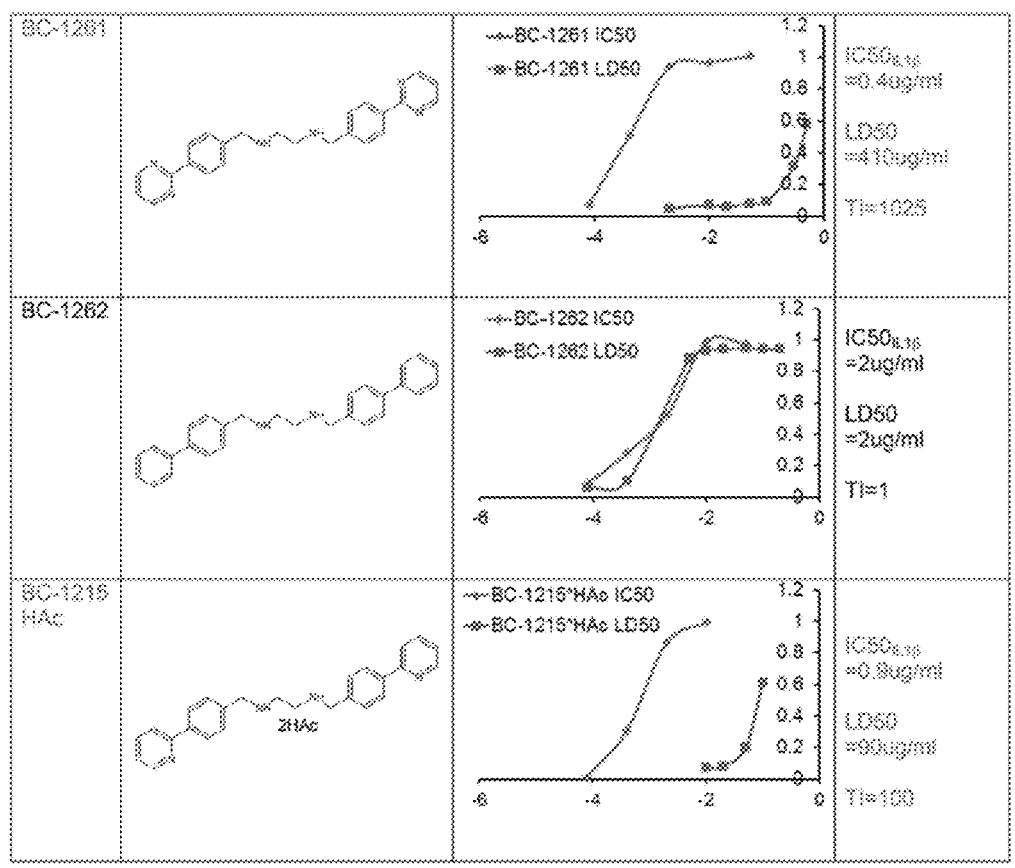
Figure 25A:
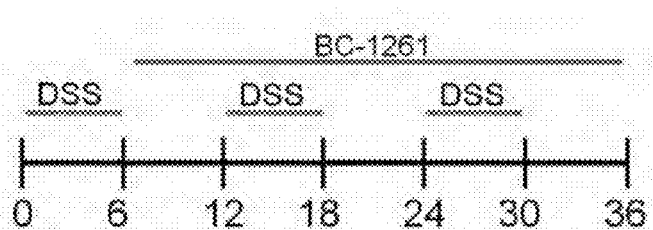
Figure 25B:
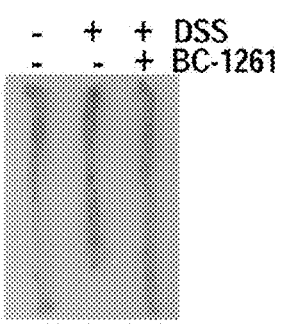
Figure 25C:
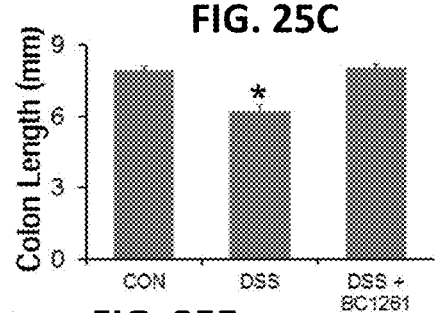
Figure 25D:
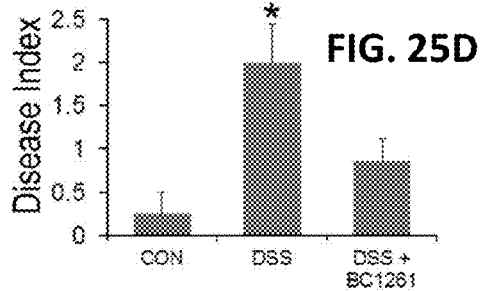
Figure 25E:
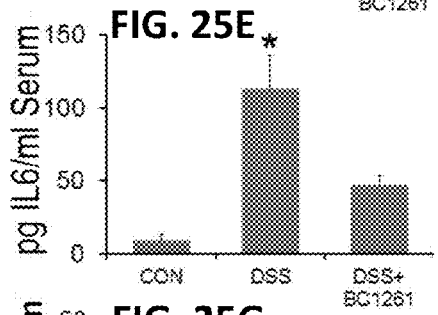
Figure 25F:
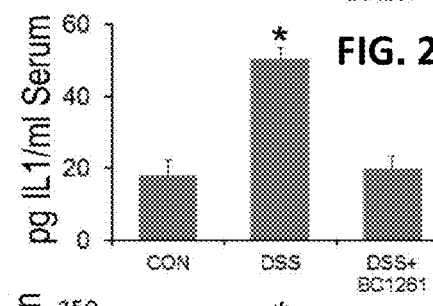
Figure 25G:
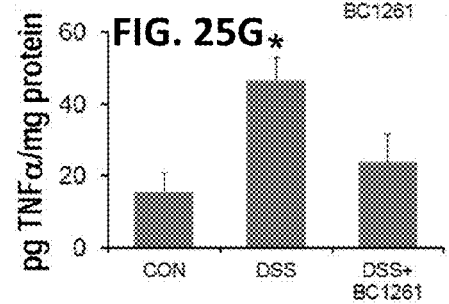
Figure 25H:
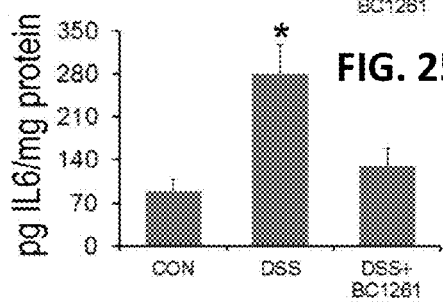
Figure 25I:
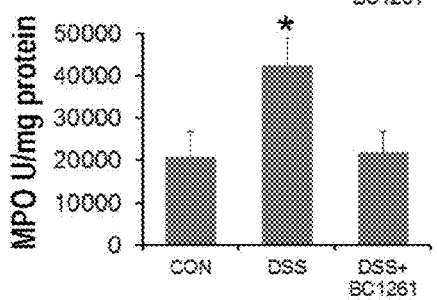
Figure 25J:
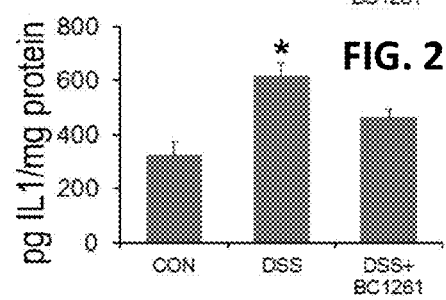
Figure 26A:
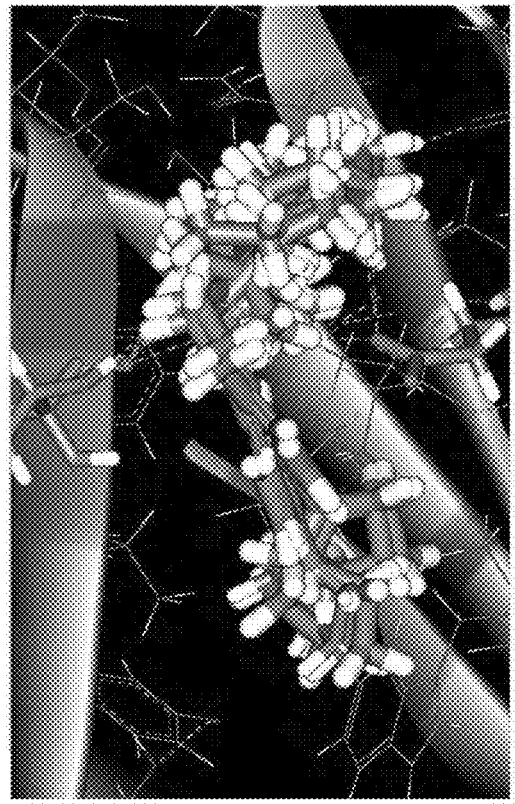
Figure 26B:
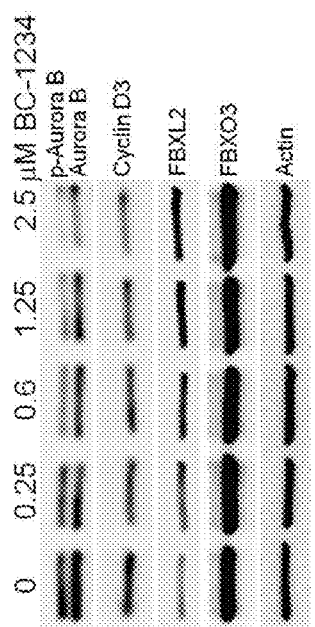
Figure 26C:
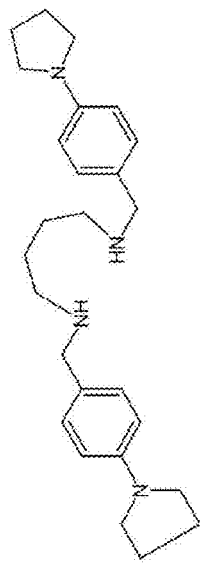
Figure 26D:
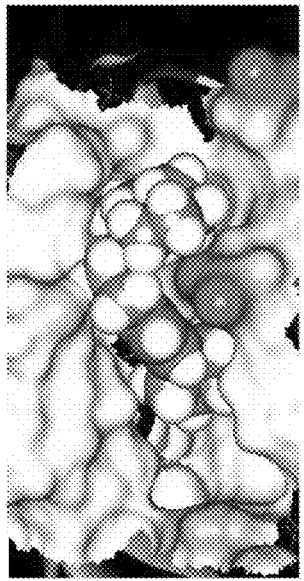
Figure 27A:
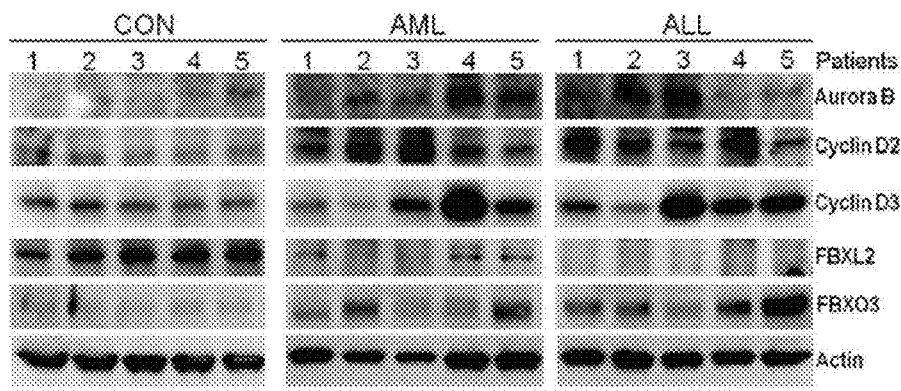
Figure 27B:
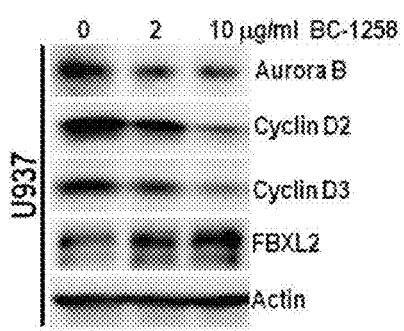
Figure 27C:
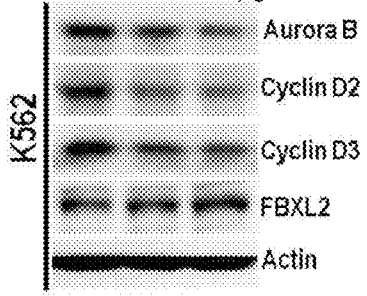
Figure 27D:
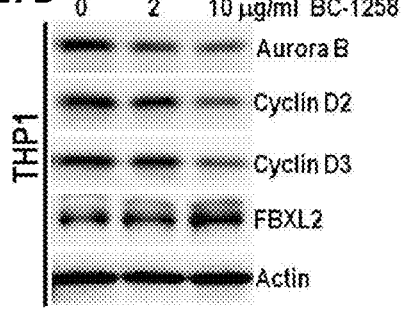
Figure 27E:
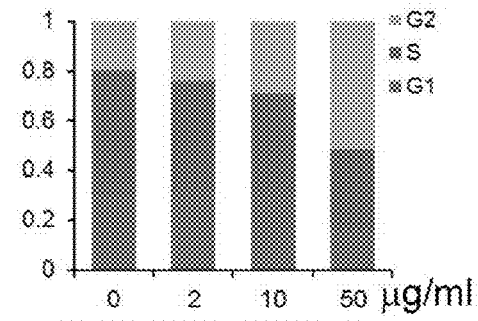
Figure 27F:
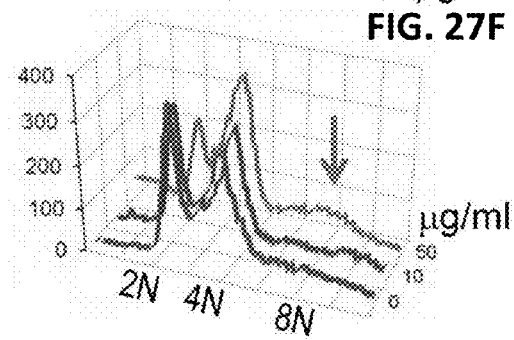
Figure 27G:
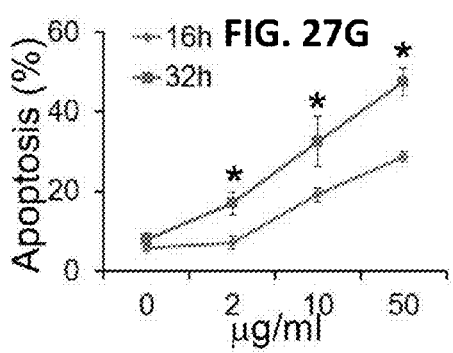

FIG. 18. A proposed novel inflammatory pathway catalyzed by FBXO3.
Infection or autoimmune disorders might involve the following pathway: FBXO3-|FBXL2-|TRAFs→cytokine production→tissue inflammation, injury, and edema. Specifically, local and systemic inflammation is regulated in part, by a unique pathway whereby a previously unrecognized E3 ligase component, FBXO3, triggers ubiquitination and degradation of another E3 ligase subunit, FBXL2, thereby increasing levels of TRAF proteins that mediate cytokine secretion from inflammatory cells. In essence, FBXL2 appears to be a feedback inhibitor of inflammation. As TRAFs are critical molecular inputs to cytokine gene expression via NF-κ, mutation or inhibition of FBXO3 will prevent induction of TRAF proteins and suppress cytokine production. FBXO3 serves as a novel molecular target as the centerpiece of this invention that has led to the genesis of F box protein ubiquitin E3 ligase inhibitors.

FIG. 19. Kirby-Bauer antibiotic testing. BC-1215 was tested in antibiotic sensitivity tests using Mueller-Hinton agar. Briefly, 6 mm filter papers containing different amounts of BC-1215 or gentamicin (positive control) were added on the Mueller-Hinton agar pre-exposed to *Staphylococcus aureus*. The plates were incubated at 37 degrees for 24 h. Zone sizes were measured and marked by a red circle indicating positive results. The data suggest that BC-1215 may inhibit bacterial growth through interaction with the bacterial ApaG protein.

FIGS. 20A-20J is a table depicting benzathine compounds, and assay results. PBMC cells (0.6 ml at $1.5*10^6$/ml) were treated with 2 ug/ml LPS for 16 hrs along with each compound at different concentrations. IL1β and TNFα cytokine release were monitored by ELISA to calculate the IC50. U937 monocyte (0.6 ml at $1.5*10^6$/ml) were treated with each compound at different concentrations for 16 h. Cells were then stained with Trypan blue to differentiate dead cells, and calculate the LD50. Therapeutic index (TI)=LD50/IC50. Compounds marked in red are high value targets (low IC50, high LD50) and require further testing in vivo.

FIGS. 21A-21E. BC-1261 reduces *P. aeruginosa* induced lung inflammation. BC-1261 was administered to mice though an i.p. injection, and mice were then immediately challenged with *P. aeruginosa* (strain PA103, $2.5*10^4$ cfu/mouse, i.t.) or without (control, CON) for an additional 18 h. Mice were then euthanized and lungs were lavaged with saline, harvested, and then homogenized. Lavage protein, cell counts and cytokine secretion were measured in (A-C). D. Lavage cells were processed with cytosin and stained with May-Grunwald and Geimsa. E. H&E staining was performed on lung samples. The data represent n=4 mice/group, *P<0.05 versus PA103

FIGS. 22A-22C. BC-1261 reduces smoke induced chronic lung inflammation. Mice were exposed to cigarette smoke for 5 weeks before one does of i.p. injection of BC1261 (100 ug), 18 h later, mice were euthanized and lungs were lavaged with saline, harvested, and then homogenized. Lavage protein, cell counts and cytokine secretion were measured in (A-C). The data represent n=3 mice/group, *P<0.05 versus con.

FIGS. 23A-23D. BC-1261 reduces TPA induced ear edema. Different dose of BC-1261 was applied to ears of mice at various doses 30 min after TPA administration (2 µg/ear). A. Gross comparisons were made with equal volumes of ethanol as a vehicle control (CON). 18 h after TPA administration, mice were euthanized and the thickness of the ear was measured using a micrometer (B). Autopsy sample were also taken to measure MPO activity (C) and calculate ear edema (D). The data represent n=6 mice/group, *P<0.05 versus TPA.

FIGS. 24A-24E. BC-1261 reduces DSS induced acute colonic inflammation. A-D. C57BL6 mice were fed with water ad lib containing 3.5% dextran sulfate sodium (DSS) for up to five days. Mice were treated with either vehicle (control [CON]) or BC-1261 (150 µg) daily (via an i.p. injection), or BC-1261 were administered into drinking water at 30 µg/ml (po). Mice were then euthanized and the length of the colon was measured and graphed in (A-B). Colonic tissues were also analyzed for TNFα (C) and IL6(D). E. H&E staining was performed on colonic sections. The data represent n=4 mice/group, *P<0.05 versus DSS and **P<0.05 versus CON.

FIGS. 25A-25J. BC-1261 reduces DSS induced chronic colonic inflammation. A.
C57BL6 mice were fed with water ad lib containing 2% dextran sulfate sodium (DSS) for six days, then switch to water for up to three cycles. BC-1261 was administered into drinking water at 30 µg/ml, starting at day 7. Mice were euthanized at the end of the experiment and the length of the colon was measured and graphed in (B-C). Disease index was measured and graphed in (D). Serum cytokine levels were measured in (E-F). Colonic tissues cytokines and MPO activity were also analyzed (GJ). The data represent n=7 mice/group, *P<0.05 versus CON.

FIGS. 26A-26D. Docking study of compound BC-1234 with FBXO3-ApaG domain A. BC-1234 structure. B. BC-1234 interacts with Glu64 and Thr91 residues within the FBXO3 ApaG motif. C. The five poses of BC-1234 with the best docking scores interacting with FBXO3-ApaG motif. D. BC-1234 were further tested in MLE (murine epithelia cells). Briefly, MLE cells were treated with BC-1234 at different concentrations for 16 h. Cells were then collected and assayed for Aurora B, cyclin D3, FBXL2 and FBXO3 immunoblotting.

FIGS. 27A-27G. BC-1258 Induces G2/M arrest and apoptosis in cancer cells. A. PBMCs from 5 controls, AML, and ALL subjects were cultured in RPMI medium for 18 h. Cells were then collected, lysed, and assayed for protein immunoblotting. B-D. Human leukemia cells (U937, K562 and THP1 cells) were treated with BC-1258 at different concentrations for 16 h. Cells were collected and assayed for Aurora B, cyclin D2, cyclin D3 and FBXL2 immunoblotting. E-F. MLE cells were treated with BC-1258 at different concentrations for 16 h, cells were processed by BrdU uptake and 7-AAD staining followed by FACS cell cycle analysis (E), 2N, 4N, and 8N DNA histograms were quantitated and graphed in (F). G. Quantification of FACS analysis showing levels of apoptotic MLE cells after BC-1258 treatment at each time point.

FIGS. 28A-28I. BC-1258 suppresses tumor growth in xenograft. A-E. Effect of BC-1258 and other compounds on growth of U937 tumor implants in nude mice, n=4 mice/group with drug concentration at 30 ug/ml in the drinking water. The panel A showed representative images of variable sizes of xenograft in three nude mice (arrows) after drug treatment. B. Tumor volume measurements over time (n=4 mice/group, *P<0.05 versus con). D. Tumor tissue from C were weighted and graphed (n=4 mice/group, *P<0.05 versus con). E. Tumors from three controls and three drug treated U937 implants in mice were collected at the endpoint, and assayed for AuroraB, CaM and FBXL2 proteins by immunoblotting. F-I. Serum of each mice were collected at the end point and processed for creatinine, LDH, ALT and creatine kinase activity.

FIG. 29. ApaG drug binding motif.

FIG. 30. FBXO3-ApaG interaction with compounds BC-1261 and BC-1234.

FIG. 31. FBXO3-ApaG interaction with compound BC-1304.

Figure 32:
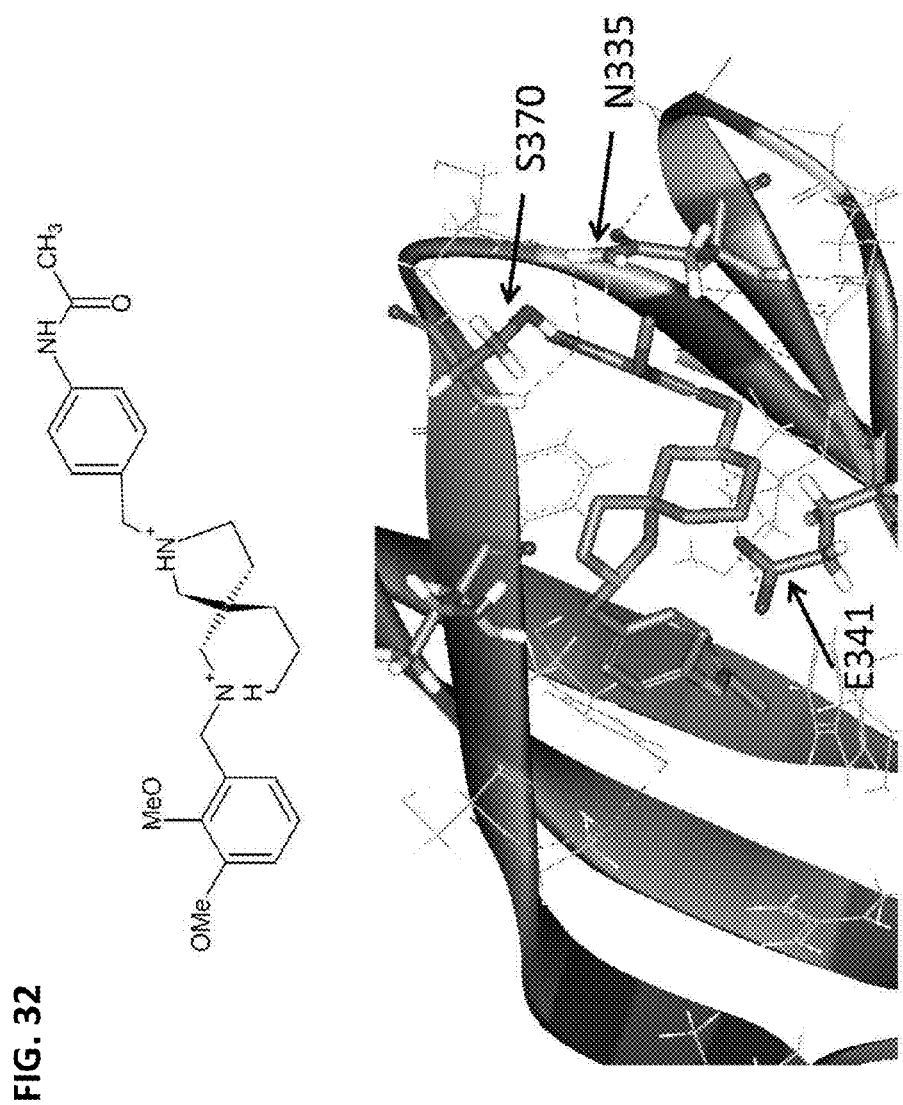

FIG. 32. FBXO3-ApaG interaction with compound BC-1305.

FIG. 33. FBXO3-ApaG interaction with compound BC-1305 (Secondary position).

Figure 34:
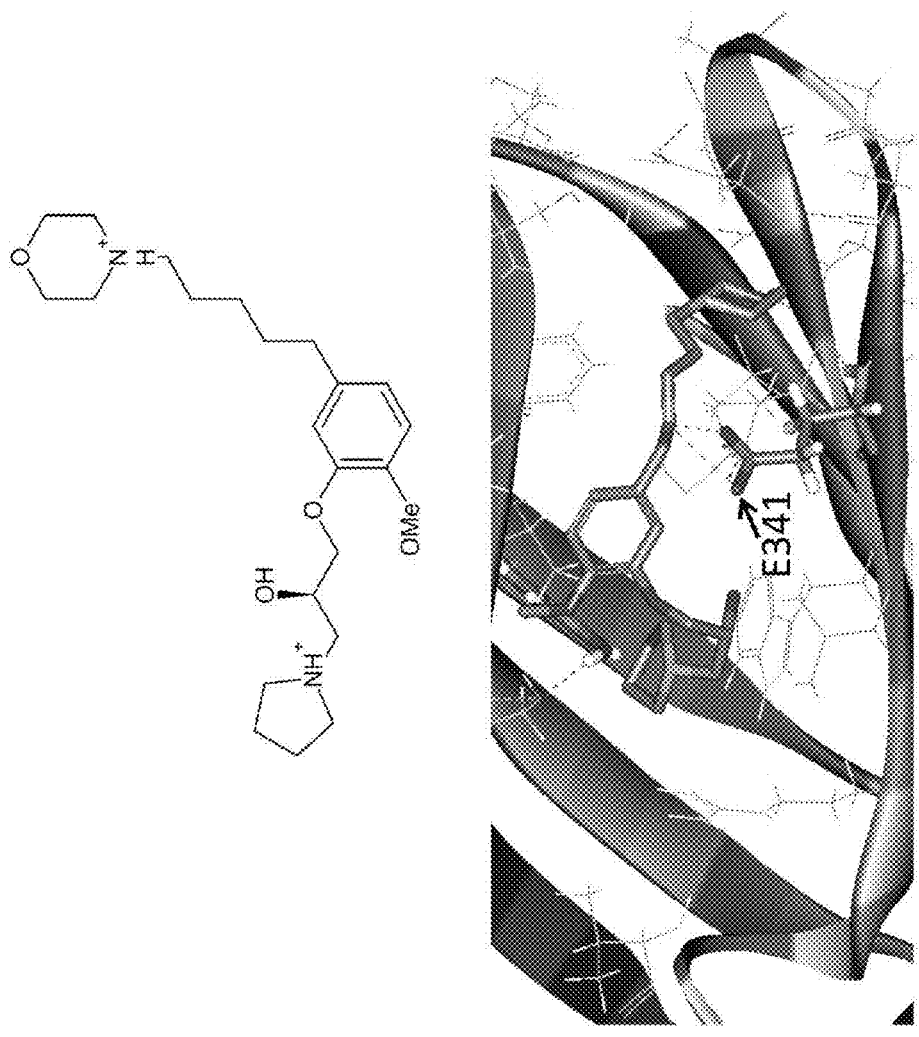

FIG. 34. FBXO3-ApaG interaction with compound BC-1306.

FIG. 35. FBXO3-ApaG interaction with compound BC-1307.

FIG. 36. FBXO3-ApaG interaction with compound BC-1308.

Figure 37:
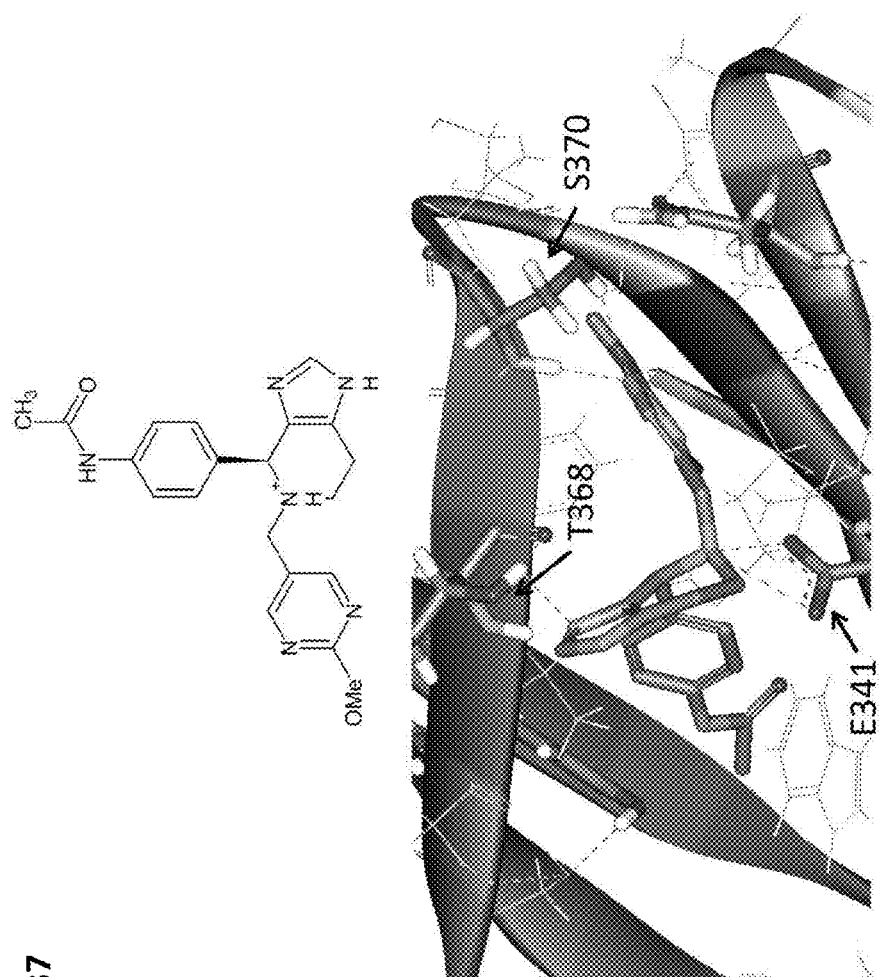

FIG. 37. FBXO3-ApaG interaction with compound BC-1309.

FIG. 38. Table summarizing toxicity screening for compounds BC-1215 and BC-1261.

SEQUENCE LISTING

The amino acid sequence listed in the accompanying sequence listing is shown using standard three letter code for amino acids, as defined in 37 C.F.R. 1.822. The Sequence Listing is submitted as an ASCII text file, created on Oct. 9, 2018, 4.59 KB, which is incorporated by reference herein.

DETAILED DESCRIPTION

Terminology

As used herein, the singular terms "a," "an," and "the" include plural referents unless context clearly indicates otherwise. Also, as used herein, the term "comprises" means "includes."

Although methods and materials similar or equivalent to those described herein can be used in the practice or testing of the present disclosure, suitable methods and materials are described below. In addition, the materials, methods, and examples are illustrative only and not intended to be limiting.

To facilitate review of the various examples of this disclosure, the following explanations of specific terms are provided:

"Acyl" refers to a group having the structure —C(O)R, where R may be, for example, optionally substituted alkyl, optionally substituted aryl, or optionally substituted heteroaryl.

"Lower acyl" groups are those that contain one to six carbon atoms.

"Acyloxy" refers to a group having the structure —OC(O)R—, where R may be, for example, optionally substituted alkyl, optionally substituted aryl, or optionally substituted heteroaryl. "Lower acyloxy" groups contain one to six carbon atoms.

"Administration" as used herein is inclusive of administration by another person to the subject or self-administration by the subject.

The term "aliphatic" is defined as including alkyl, alkenyl, alkynyl, halogenated alkyl and cycloalkyl groups. A "lower aliphatic" group is a branched or unbranched aliphatic group having from 1 to 10 carbon atoms.

"Alkanediyl," "cycloalkanediyl," "aryldiyl," "alkanearyldiyl" refers to a divalent radical derived from aliphatic, cycloaliphatic, aryl, and alkanearyl hydrocarbons.

"Alkenyl" refers to a cyclic, branched or straight chain group containing only carbon and hydrogen, and contains one or more double bonds that may or may not be conjugated. Alkenyl groups may be unsubstituted or substituted. "Lower alkenyl" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, isobutoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$ alkanoyl can be acetyl, propanoyl or butanoyl; halo$(C_1-C_6)$ alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$ alkanoyloxy can be acetoxy, propanoyloxy, butanoyloxy, isobutanoyloxy, pentanoyloxy, or hexanoyloxy.

"Alkynyl" refers to a cyclic, branched or straight chain group containing only carbon and hydrogen, and contains one or more triple bonds. Alkynyl groups may be unsubstituted or substituted. "Lower alkynyl" groups are those that contain one to six carbon atoms.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group. For example, an "alkylamino" or "alkylated amino" refers to —NRR', wherein at least one of R or R' is an alkyl.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H). A suitable aminocarbonyl group is acetamido.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Aryl" refers to a monovalent unsaturated aromatic carbocyclic group having a single ring (e.g., phenyl) or multiple condensed rings (e.g., naphthyl or anthryl), which can optionally be unsubstituted or substituted. A "heteroaryl group," is defined as an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

The term "aralkyl" refers to an alkyl group wherein an aryl group is substituted for a hydrogen of the alkyl group. An example of an aralkyl group is a benzyl group.

"Aryloxy" or "heteroaryloxy" refers to a group of the formula —OAr, wherein Ar is an aryl group or a heteroaryl group, respectively.

Atomic coordinates or structure coordinates refers to mathematical coordinates derived from mathematical equations related to the patterns obtained on diffraction of a monochromatic beam of X-rays by the atoms (scattering centers) such as a protein. In some examples that protein can be FBXO3 protein in a crystal. The diffraction data are used to calculate an electron density map of the repeating unit of the crystal. The electron density maps are used to establish the positions of the individual atoms within the unit cell of the crystal. In one example, the term "structure coordinates" refers to Cartesian coordinates derived from mathematical equations related to the patterns obtained on diffraction of a monochromatic beam of X-rays, such as by the atoms of a FBXO3 protein in crystal form. Those of ordinary skill in the art understand that a set of structure coordinates determined by X-ray crystallography is not without standard error. For the purpose of this disclosure, any set of structure coordinates that have a root mean square deviation of protein backbone atoms (N, Cα, C and O) of less than about 1.0 Angstroms when superimposed, such as about 0.75, or about 0.5, or about 0.25 Angstroms, using backbone atoms, shall (in the absence of an explicit statement to the contrary) be considered identical.

The term "carboxylate" or "carboxyl" refers to the group —COO or —COOH.

The term "co-administration" or "co-administering" refers to administration of a FBXO3 inhibitor with at least one other therapeutic agent within the same general time period, and does not require administration at the same exact moment in time (although co-administration is inclusive of administering at the same exact moment in time). Thus, co-administration may be on the same day or on different days, or in the same week or in different weeks. The additional therapeutic agent may be included in the same composition as the FBXO3 inhibitor.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "ester" refers to a carboxyl group having the hydrogen replaced with, for example, a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

The term "halogen" refers to fluoro, bromo, chloro and iodo substituents.

The terms 'halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

"Inhibiting" refers to inhibiting the full development of a disease or condition. "Inhibiting" also refers to any quantitative or qualitative reduction in biological activity or binding, relative to a control.

"N-heterocyclic" or "N-heterocycle" refers to mono or bicyclic rings or ring systems that include at least one nitrogen heteroatom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$alkyl, $C_{1-6}$alkoxy, $C_{2-6}$alkenyl, $C_{2-6}$ alkynyl, halo, hydroxy, mercapto, trifluoromethyl, amino, cyano or mono or di($C_{1-6}$alkyl)amino. The N-heterocyclic group may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, purinyl, cinnolinyl, phthalazinyl, quinazolinyl, quinoxalinyl, benzotriazinyl, and the like. These heterocycles may be optionally substituted, for example with $C_{1-6}$alkyl, $C_{1-6}$alkoxy, $C_{2-6}$alkenyl, $C_{2-6}$alkynyl, halo, hydroxy, mercapto, trifluoromethyl, amino, cyano or mono or di($C_{1-6}$alkyl)amino. Unless otherwise defined optionally substituted N-heterocyclics includes pyridinium salts and the N-oxide form of suitable ring nitrogens.

"Nitro" refers to an R-group having the structure —$NO_2$.

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-groups/substituents include alkyl groups, hydroxyl groups, alkoxy groups, acyloxy groups, mercapto groups, and aryl groups.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refer to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$ alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

A "therapeutically effective amount" refers to a quantity of a specified agent sufficient to achieve a desired effect in a subject being treated with that agent. For example, a therapeutically amount may be an amount of a FBXO3 inhibitor that is sufficient to inhibit inflammation in a subject. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as cancer. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition. In certain embodiments disclosed herein, the treatment inhibits inflammation in a subject.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Some of the compounds described herein may also exist in their tautomeric form.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Groups which are substituted (e.g. substituted alkyl), may in some embodiments be substituted with a group which is substituted (e.g. substituted aryl). In some embodiments, the number of substituted groups linked together is limited to two (e.g. substituted alkyl is substituted with substituted aryl, wherein the substituent present on the aryl is not further substituted). In some embodiments, a substituted group is not substituted with another substituted group (e.g. substituted alkyl is substituted with unsubstituted aryl).

Overview

It has been discovered that pathogens activate a relatively recently-identified ubiquitin E3 ligase subunit, termed FBXO3 (SEQ ID1), which is sufficient to ubiquitinate and mediate proteasomal degradation of another relatively recently-identified ubiquitin E3 ligase subunit, termed FBXL2. Further, it has also been discovered that FBXL2 acts as a "break" on inflammation, by targeting the TRAF family of proteins for their disposal in epithelia and monocytes. Thus, pathogens, via activation of FBXO3, result in FBXL2 ubiquitination and degradation resulting in increased immunoreactive TRAFs, increased cytokine production, and impaired lung stability. Specifically, the data disclosed herein show that i) FBXL2 targets six TRAF family proteins (TRAF1-6) for their ubiquitination and degradation, (ii) FBXO3 specifically targets FBXL2 for its ubiquitination and degradation, (iii) glycogen synthase kinase (GSK3β) phosphorylates FBXL2 thereby serving as a novel molecular signal for FBXO3 ubiquitination of FBXL2, and (iv) compared to wild-type (Wt) FBXO3, expression of a naturally occurring FBXO3 point mutant (FBXO3V220I) fails to stimulate cytokine production after P. aeruginosa infection, and expression of FBXO3V220I lessens the severity of inflammatory lung injury in murine models of pneumonia.

The discovery of FBXO3 is of particular importance as it contains a bacterial-like molecular signature within its tertiary structure not detected in mammalian proteins. This motif, termed Apa G, led to the presently disclosed development of a highly unique, selective phylum of small molecule therapeutics that block FBXO3 activity, reduce TRAF levels to native levels, profoundly inhibit cytokine release from human cells, and lessen the severity of inflammation in septic animal models. A series of small molecule inhibitors of FBXO3 were generated that when tested attenuate lipopolysaccharide (LPS)-induced cytokine secretion from human peripheral blood mononuclear cells. In one embodiment, the FBXO3 inhibitor BC-1215 inhibits inflammation and prevents tissue damage in several animal models.

Provided herein is a new molecular model of innate immunity as it relates to cytokine signaling. Two previously poorly characterized proteins (FBXO3, FBXL2) newly linked to the cytokine response through TRAF protein signaling have been uncovered. The studies disclosed herein are the first to elucidate the enzymatic behavior FBXO3 that appears to activate the FBXL2-TRAF-cytokine axis. Based on the previously unrecognized novel mechanism of FBXO3 activity in the TRAF inflammatory pathway, the agents disclosed herein target a unique prokaryotic molecular signature within the F box protein. Disclosed herein are benzathine compounds that serve as highly selective small molecule inhibitors of FBXO3, and that may be useful in the prophylaxis and treatment of septic shock, pneumonia, and other inflammatory conditions.

Compounds

Disclosed herein in one embodiment are FBXO3 inhibitors. Illustrative FBXO3 inhibitors include benzathine compounds, optionally-substituted diaminoalkanes (e.g., 1,10-diaminodecane), substituted quinolines (e.g., quinidine, hydroxychloroquine, primaquine), haematoxylin, tetramethylenebis, naphthacaine, ampicillin, and elliptine, and pharmaceutically acceptable salts and esters thereof.

The benzathine compound may be benzathine or a benzathine analog. In certain embodiments the benzathine compound is not benzathine penicillin. In certain embodiments the benzathine analog includes a divalent diamine core moiety, a first aryl-containing moiety at a first terminal end of the divalent diamine core moiety, and a second aryl-containing moiety at a second terminal end of the divalent diamine core moiety. Each amino groups of the diamine group may be individually —NH— or —NR—, wherein R is a substituted group as described such as a lower alkyl, alkoxy, hydroxy, acyl, acyloxy, alkoxycarbonyl, aryl, carboxyl, or ester. The divalent diamine core moiety may include an optionally-substituted alkanediyl, an optionally-substituted cycloalkanediyl, an optionally-substituted aryldiyl, or an optionally-substituted alkanearyldiyl positioned between the two amino groups. In certain embodiments the two amino groups of the diamine may together with carbon atoms form a heteroaryldiyl group. The terminal aryl-containing groups may each individually be an aralkyl group (preferably a benzyl group) or an N-heteroaralkyl group such as -alkyl-pyrazinyl, -alkyl-pyrimidinyl, -alkyl-pyridazinyl, or -alkyl-pyridinyl. The aryl ring of the aralkyl group may be substituted with an optionally-substituted N-heterocyclic group. In certain embodiments, the optionally-substituted N-heterocyclic group is located at a ring position para to the point of attachment of the aralkyl group to the divalent diamine core moiety.

Illustrative benzathine analogs include optionally-substituted N-heterocyclic-substituted benzathines. In certain embodiments, the benzathine analogs include two phenyl rings, wherein at least one, and preferably both, of the phenyl rings are substituted with an optionally-substituted N-heterocyclic group, which optionally-substituted N-heterocyclic may be the same or different. In certain embodiments, the optionally-substituted N-heterocyclic group is located at a ring position para to the point of attachment of the phenyl ring to the benzathine molecular scaffold.

Illustrative N-heterocyclic groups include, for example, pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, piperidinyl, morpholinyl, thiomorpholinyl, piperazinyl, and triazinyl. Particularly preferred N-heterocyclic groups include imidazolyl, pyridyl, pyrazolyl, oxadiazolyl and pyrimidinyl.

The benzathine analogs, or pharmaceutically acceptable salts or esters thereof, may have structure of formula I:

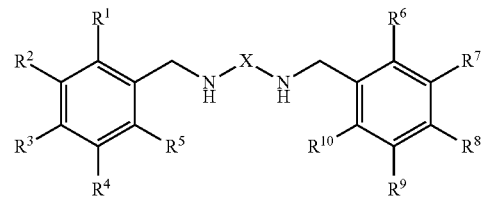

wherein X is a divalent or tetravalent linking moiety; and
$R^1$-$R^{10}$ are each individually H, optionally-substituted alkyl, optionally-substituted alkoxy, optionally-substituted aryl, optionally-substituted cycloalkyl, optionally-substituted heterocyclic, halogen, amino, or hydroxy.

In certain embodiments of formula I, X is an optionally-substituted alkanediyl, an optionally-substituted cycloalkanediyl, an optionally-substituted aryldiyl, or an optionally-substituted alkanearyldiyl. For example, X may be an alkanediyl having a structure of —$C_nH_{2n}$— wherein n is 1 to 10, more preferably 2 to 5; X may be a —$C_6H_{10}$— cycloalkanediyl; or X may be a —$C_6H_4$— aryldiyl. A particularly preferred X moiety is —$CH_2$—$CH_2$—.

In certain embodiments of formula I, X is a tetravalent moiety that is derived from a spiro structure wherein the nitrogen atoms of the diamine core form N-heteroatoms of the spiro structure. For example, X together with the diamine may form a diazaspirodecane. An example of a diazaspirodecane is shown below in formula VI.

In certain embodiments of formula I, at least one of $R^1$-$R^{10}$ is not H. In certain embodiments of formula I, at least one of $R^3$ or $R^8$ is an optionally-substituted alkyl, optionally-substituted alkoxy, optionally-substituted aryl, optionally-substituted cycloalkyl, optionally-substituted heterocyclic, halogen, amino, or hydroxy. In certain embodiments of formula I, at least one of $R^3$ or $R^8$, and preferably both of $R^3$ and $R^8$, is an unsubstituted alkoxy, aryl-substituted alkoxy, halo-substituted alkoxy, aryl, optionally-substituted heterocyclic, halogen, amino, or hydroxy. In certain embodiments of formula I, at least one of $R^1$-$R^{10}$ is an N-heterocyclic, particularly a 5-membered or 6-membered N-heterocyclic. In certain embodiments of formula I, at least one of $R^3$ or $R^8$, and preferably both of $R^3$ and $R^8$, is an N-heterocyclic, particularly a 5-membered or 6-membered N-heterocyclic. Illustrative N-heterocyclic groups include, for example, pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, piperidinyl, morpholinyl, thiomorpholinyl, piperazinyl, and triazinyl. Particularly preferred N-heterocyclic groups include imidazolyl, pyridyl, pyrazolyl, and pyrimidinyl. Especially preferred N-heterocyclic groups include imidazolyl, pyridyl, and pyrazolyl. In certain embodiments of formula I, $R^1$, $R^2$, $R^4$, $R^5$, $R^6$, $R^7$, $R^9$ and $R^{10}$ are each H. In certain embodiments of formula I, $R^1$, $R^2$, $R^4$, $R^5$, $R^6$, $R^7$, $R^9$ and $R^{10}$ are each H; X is an optionally-substituted alkanediyl, and $R^3$ and $R^8$ are each individually an optionally-substituted 5-membered or 6-membered N-heterocyclic. In certain embodiments of formula I, $R^3$ and $R^8$ are each the same group.

Disclosed herein in a further embodiment are compounds, or pharmaceutically acceptable salts or esters thereof, having a structure of formula II:

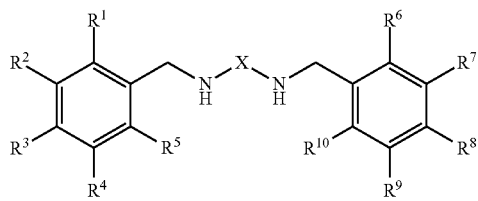

wherein X is a divalent linking moiety; and
$R^1$-$R^{10}$ are each individually H, optionally-substituted alkyl, optionally-substituted alkoxy, optionally-substituted aryl, optionally-substituted cycloalkyl, optionally-substituted heterocyclic, halogen, amino, or hydroxy, provided that at least one of $R^3$ or $R^8$ is an optionally-substituted alkyl, a substituted alkoxy, optionally-substituted aryl, optionally-substituted cycloalkyl, optionally-substituted heterocyclic, or halogen.

In certain embodiments of formula II, X is an optionally-substituted alkanediyl, an optionally-substituted cycloalkanediyl, an optionally-substituted aryldiyl, or an optionally-substituted alkanearyldiyl. For example, X may be an alkanediyl having a structure of —$C_nH_{2n}$— wherein n is 1 to 10, more preferably 2 to 5; X may be a —$C_6H_{10}$— cycloalkanediyl; or X may be a —$C_6H_4$— aryldiyl. A particularly preferred X moiety is —$CH_2$—$CH_2$—.

In certain embodiments of formula II, at least one of $R^1$-$R^{10}$ is an N-heterocyclic, particularly a 5-membered or 6-membered N-heterocyclic. In certain embodiments of formula II, at least one of $R^3$ or $R^8$, and preferably both of $R^3$ and $R^8$, is an N-heterocyclic, particularly a 5-membered or 6-membered N-heterocyclic. Illustrative N-heterocyclic groups include, for example, pyrrolyl, H-pyrrolyl, pyrrolinyl, pyrrolidinyl, oxazolyl, oxadiazolyl, (including 1,2,3; 1,2,4; and 1,3,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), dithiazolyl, pyridyl, pyrimidinyl, pyridazinyl, pyrazinyl, piperidinyl, morpholinyl, thiomorpholinyl, piperazinyl, and triazinyl. Particularly preferred N-heterocyclic groups include imidazolyl, pyridyl, pyrazolyl, oxadiazolyl and pyrimidinyl. Especially preferred N-heterocyclic groups include imidazolyl, pyridyl, and pyrazolyl. In certain embodiments of formula II, $R^1$, $R^2$, $R^4$, $R^5$, $R^6$, $R^7$, $R^9$ and $R^{10}$ are each H. In certain embodiments of formula II, $R^1$, $R^2$, $R^4$, $R^5$, $R^6$, $R^7$, $R^9$ and $R^{10}$ are each H; X is an optionally-substituted alkanediyl, and $R^3$ and $R^8$ are each individually an optionally-substituted 5-membered or 6-membered N-heterocyclic. In certain embodiments of formula II, $R^3$ and $R^8$ are each the same group.

Disclosed herein in a further embodiment are compounds, or pharmaceutically acceptable salts or esters thereof, having a structure of formula III:

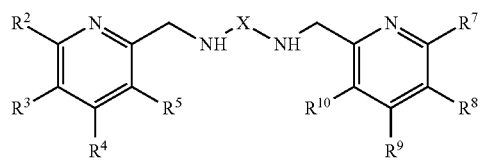

wherein X is a divalent linking moiety; and
$R^2$-$R^5$ and $R^7$-$R^{10}$ are each individually H, optionally-substituted alkyl, optionally-substituted alkoxy, optionally-substituted aryl, optionally-substituted cycloalkyl, optionally-substituted heterocyclic, halogen, amino, or hydroxy.

In certain embodiments of formula III, X is an optionally-substituted alkanediyl, an optionally-substituted cycloalkanediyl, an optionally-substituted aryldiyl, or an optionally-substituted alkanearyldiyl. For example, X may be an alkanediyl having a structure of —$C_nH_{2n}$— wherein n is 1 to 10, more preferably 2 to 5; X may be a —$C_6H_{10}$— cycloalkanediyl; or X may be a —$C_6H_4$— aryldiyl. A particularly preferred X moiety is —$CH_2$—$CH_2$—. In certain embodiments of formula III, $R^2$-$R^5$ and $R^7$-$R^{10}$ are each individually H.

Disclosed herein in a further embodiment are compounds, or pharmaceutically acceptable salts or esters thereof, having a structure of formula IV:

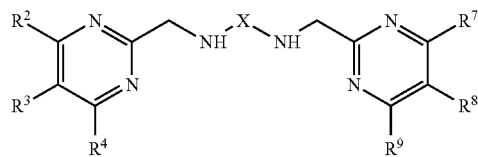

wherein X is a divalent linking moiety; and
$R^2$-$R^4$ and $R^7$-$R^9$ are each individually H, optionally-substituted alkyl, optionally-substituted alkoxy, optionally-substituted aryl, optionally-substituted cycloalkyl, optionally-substituted heterocyclic, halogen, amino, or hydroxy.

In certain embodiments of formula IV, X is an optionally-substituted alkanediyl, an optionally-substituted cycloalkanediyl, an optionally-substituted aryldiyl, or an optionally-substituted alkanearyldiyl. For example, X may be an alkanediyl having a structure of —$C_nH_{2n}$— wherein n is 1 to 10, more preferably 2 to 5; X may be a —$C_6H_{10}$— cycloalkanediyl; or X may be a —$C_6H_4$— aryldiyl. A particularly preferred X moiety is —$CH_2$—$CH_2$—. In certain embodiments of formula IV, $R^2$-$R^5$ and $R^7$-$R^{10}$ are each individually H.

Also disclosed herein in a further embodiment are compounds, or pharmaceutically acceptable salts or esters thereof, having a structure of formula V:

wherein X is a divalent linking moiety as described above;

$R^{20}$ and $R^{21}$ are each individually selected from hydrogen, lower alkyl, alkoxy, hydroxy, acyl, acyloxy, alkoxycarbonyl, aryl, carboxyl, or ester; and $R^{22}$ and $R^{23}$ are each individually selected from an optionally-substituted aryl or an optionally-substituted N-heterocycle, provided that at least one of $R^{22}$ or $R^{23}$ is an optionally-substituted N-heterocycle.

In certain preferred embodiments of formula V, $R^{23}$ is an N-heterocycle and $R^{22}$ is an N-heterocycle-substituted phenyl, particularly a para-substituted N-heterocycle-phenyl.

Also disclosed herein in a further embodiment are compounds, or pharmaceutically acceptable salts or esters thereof, having a structure of formula VI:

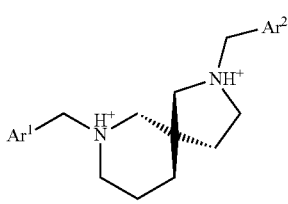

wherein $Ar^1$ and $Ar^2$ are each independently optionally-substituted aryl or optionally-substituted N-heterocyclic. Illustrative N-heterocyclic groups include pyridyl, pyrimidinyl, pyridazinyl, pyrazinyl, piperidinyl, morpholinyl, thiomorpholinyl, piperazinyl, and triazinyl. The aryl (particularly phenyl) or N-heterocyclic (particularly pyrimidinyl) may be substituted with alkyl (particularly lower alkyl), alkoxy (particularly methoxy), aminocarbonyl (particularly acetamido), halogen, or alkyl-substituted thiol (particularly —S—$CH_2CH_3$).

Also disclosed herein in a further embodiment are compounds, or pharmaceutically acceptable salts or esters thereof, having a structure of formula VII:

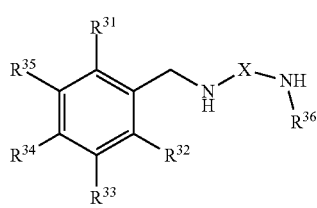

wherein X is a divalent or tetravalent linking moiety;

$R^{31}$-$R^{35}$ are each individually H, optionally-substituted alkyl, optionally-substituted alkoxy, optionally-substituted aryl, optionally-substituted cycloalkyl, optionally-substituted heterocyclic, halogen, amino, or hydroxy; and $R^{36}$ is hydrogen, optionally-substituted lower alkyl, optionally-substituted alkoxy, hydroxy, acyl, acyloxy, alkoxycarbonyl, optionally-substituted aryl, carboxyl, or optionally-substituted ester.

In certain embodiments of formula VII, X is an optionally-substituted alkanediyl, an optionally-substituted cycloalkanediyl, an optionally-substituted aryldiyl, or an optionally-substituted alkanearyldiyl. For example, X may be an alkanediyl having a structure of —$C_nH_{2n}$— wherein n is 1 to 10, more preferably 2 to 5; X may be a —$C_6H_{10}$— cycloalkanediyl; or X may be a —$C_6H_4$— aryldiyl. A particularly preferred X moiety is —$CH_2$—$CH_2$—.

In certain embodiments of formula VII, X is a tetravalent moiety that is derived from a spiro structure wherein the nitrogen atoms of the diamine core form N-heteroatoms of the spiro structure. For example, X together with the diamine may form a diazaspirodecane. An example of a diazaspirodecane is shown above in formula VI.

In certain embodiments of formula VII, at least one of $R^{31}$-$R^{35}$ is not H. In certain embodiments of formula VII, at least one of $R^3$ or $R^8$ is an optionally-substituted alkyl, optionally-substituted alkoxy, optionally-substituted aryl, optionally-substituted cycloalkyl, optionally-substituted heterocyclic, halogen, amino, or hydroxy. In certain embodiments of formula I, $R^{34}$ is an unsubstituted alkoxy, aryl-substituted alkoxy, halo-substituted alkoxy, aryl, optionally-substituted heterocyclic, halogen, amino, or hydroxy.

In certain embodiments of formula VII, $R^{36}$ is hydrogen, lower alkyl (particularly methyl, ethyl, or butyl), methoxy, hydroxy, —C(O)$R^{40}$, where $R^{40}$ is a lower alkyl, —OC(O)$R^{41}$—, where $R^{41}$ is a lower alkyl, —C(O)O$R^{42}$, wherein $R^{42}$ is a lower alkyl, phenyl, or —COOH.

In certain embodiments of formulae I-VII, the compounds may be in the form of a salt. For example, the diamine moiety within the benzathine compound structure may form a salt with an anion such as acetate (e.g., compound BC-1215 HAc), carbonate, halide, citrate, nitrate, nitrite, phosphate, phosphonate, sulfate, sulfonate, or lactic acid. In certain embodiments the compounds of formulae I-VII are water soluble thus enabling their salt formation. The water solubility of the compounds also enables formulation of the compounds into aerosol delivery for the lungs, oral administration, or emulsions for topical administration.

Illustrative compounds of formulae I and II are shown in table 1 of FIG. 20.

Illustrative compounds are also shown below:

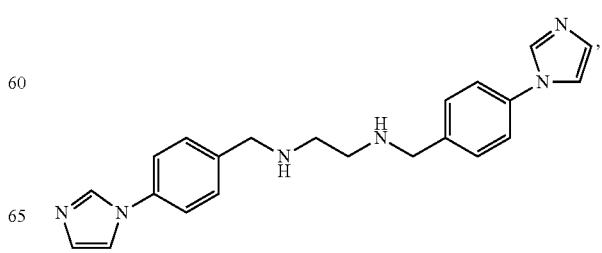

-continued

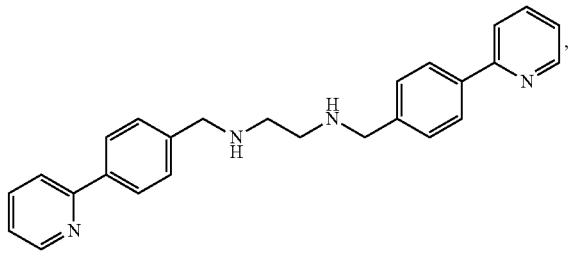

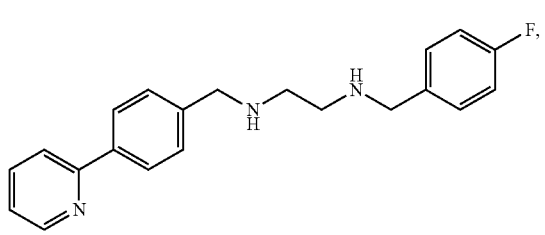

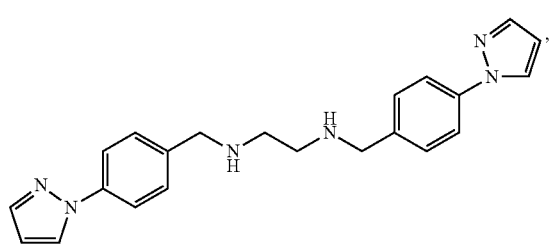

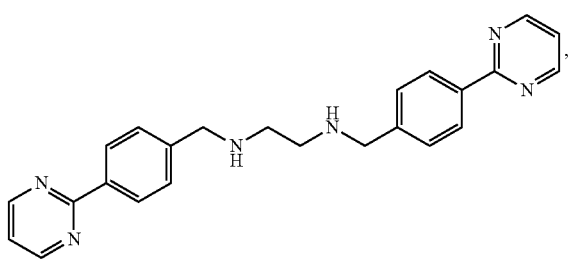

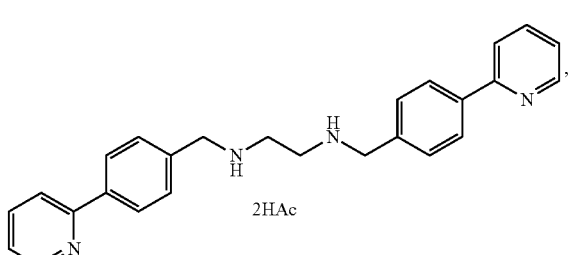
2HAc

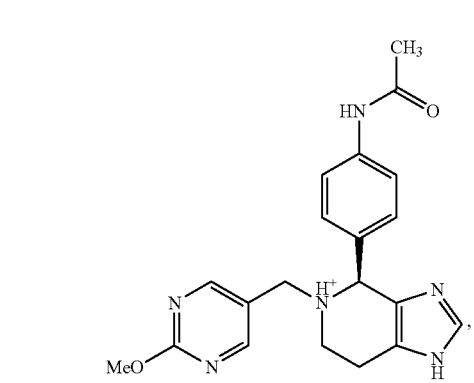

-continued

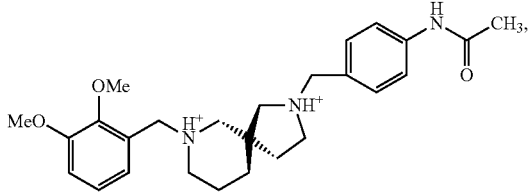

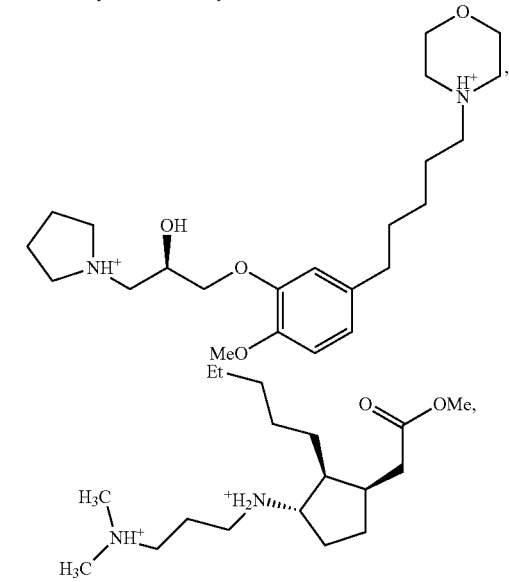

, or

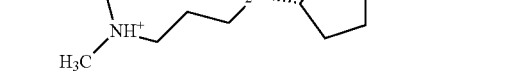

.

Methods of Use

In one embodiment the compounds disclosed herein may be used for treating inflammatory disorders, particularly inflammatory disorders that are mediated by cytokine release, especially a cytokine storm. For example, the compounds disclosed herein may be used for treating inflammatory disorders that underlie numerous human diseases characterized by a highly activated immune system that leads to secretion of large amounts of circulating pro-inflammatory cytokines after infection with virulent pathogens, in response to host cell injury, or related irritants that activate receptors on immune effector cells (T-cells, macrophages, etc.). A central feature of these infectious disorders is the burst in cytokine release, i.e. cytokine storm, from pro-inflammatory cells including macrophages, lymphocytes, and PMNs. Under many conditions, the cytokine storm is exaggerated (hypercytokinemia) and results in a fatal immune reaction with constant activation of immune effector cells that produce sustained and supraphysiologic levels of TNFα, IL-β, and IL-6 that leads to profound tissue injury. The compounds disclosed herein may inhibit the release of pro-inflammatory cytokines (e.g., TNFα, IL-β, and/or IL-6). In certain embodiments, the compounds disclosed herein are panreactive to numerous injurious cytokines. The compounds disclosed herein inhibit inflammation and prevent tissue damage (e.g., lung damage, particularly lung damage from bacterial infection) in a subject. For example, the compounds disclosed herein may inhibit hypercytokinemia, and/or may prevent or diminish supraphysiologic levels of TNFα, IL-β, and/or IL-6 or related injurious molecules.

Inflammatory disorders that may be treated by the compounds disclosed herein include any disorder possessing an inflammatory component. Illustrative inflammatory disorders include acute and chronic inflammation disorders such as asthma, chronic obstructive lung disease, pulmonary fibrosis, pneumonitis (including hypersensitivity pneumonitis and radiation pneumonitis), pneumonia, cystic fibrosis, psoriasis, arthritis/rheumatoid arthritis, rhinitis, pharyngitis, cystitis, prostatitis, dermatitis, allergy including hayfever, nephritis, conjunctivitis, encephalitis, meningitis, opthalmitis, uveitis, pleuritis, pericarditis, myocarditis, atherosclerosis, human immunodeficiency virus related inflammation, diabetes, osteoarthritis, psoriatic arthritis, inflammatory bowel disease (Crohn's disease, ulcerative colitis)/colitis, sepsis, vasculitis, bursitis, connective tissue disease, autoimmune diseases such as systemic lupus erythematosis (SLE), polymyalgia rheumatica, scleroderma, Wegener's granulomatosis, temporal arteritis, vasculitis, cryoglobulinemia, and multiple sclerosis, viral or influenza-induced inflammation, or edema. The compounds disclosed herein may be particularly effective for treating sepsis, pneumonia, influenza-induced inflammation, edema, neuropathy, colitis, arthritis, Crohn's disease, diabetes, skin, eye and ear inflammation (e.g., psoriasis, uveitis/opthalmitis, external otitis), systemic lupus erythematosis (SLE), and systemic lupus erythematosis (SLE). The compounds disclosed herein may be useful for treating inflammation and tissue damage induced by pathogenic infection with, for example, *Pseudomonas aeruginosa, Staphylococcus aureus, Streptococcus pneumoniae, Haemophilus influenza*, or *Escherichia coli*. The compounds disclosed herein may be especially effective for treating sepsis or pneumonia.

In certain embodiments the compounds disclosed herein may be antibacterial agents. The compounds may inhibit bacterial growth (function as a bacteriostatic) of, for example, *Pseudomonas aeruginosa, Staphylococcus aureus, Streptococcus pneumoniae, Haemophilus influenza*, or *Escherichia coli*. The compounds may inhibit bacterial growth through interaction with the bacterial ApaG protein. The bacterial growth may be inhibited in a subject by administering the compound to the subject. Bacterial growth on a surface of an object (e.g., a food item, a surgical implement, a kitchen surface, a hospital surface, etc.) may be inhibited by administering or applying the compound to the surface of the object.

In certain embodiments the compounds disclosed herein may be used for treating other FBXO3-mediated disorders or injuries such as, for example, malaria, toxic lung exposure, cancer, Alzheimer's, or a burn-related injury. Illustrative cancers include leukemia, lymphoma, bronchogenic carcinoma, adenocarcinoma of the breast, colon, ovary, thyroid, pancreas, stomach, and prostate, squamous cell cancer, small cell cancer, melanoma, sarcoma, and metastatic cancer. Since an FBXO3 inhibitor up-regulates FBXL2, other substrates of FBXL2 such as cyclin D2/3, Aurora B protein will be degraded upon FBXO3 inhibitor treatment. Since Cyclin D2/3 and Aurora B are well-described oncoproteins, thus FBXO3 inhibitor may inhibit cancer proliferation through inhibiting cyclins and Aurora B protein.

Another embodiment disclosed herein is a method for inhibiting pro-inflammatory cytokine release in a subject, comprising administering to the subject an FBXO3 inhibitor. The FBXO3 inhibitor inhibits FBXO3 activity, reduces TRAF protein levels in cells, inhibits cytokine release from cells, and lessens the severity of inflammation in a septic subject. In certain embodiments, the FBXO3 inhibitor reduces the concentration of TRAF proteins (e.g., TRAF2, TRAF5 and TRAF6) in cells in a subject that has been subjected to a cytokine-inducing event such as an infection. By targeting TRAF-mediated cytokine release, an FBXO3 inhibitor may avoid the severe long-term effects of corticosteroids that suppress inflammation at multiple biological pathways, but provide a broader systemic effect relative to anti-inflammatories targeted to a single cytokine. In certain embodiments analysis of inflammatory blood cells in subjects treated with FBXO3 inhibitors will show reduced TRAF protein levels.

In certain embodiments, the compounds disclosed herein target a "bacterial-like" molecular signature (the ApaG domain (SEQ ID1, residues 278-400)) identified within FBXO3 that is not identified in other proteins within mammalian host cells. This feature is highly attractive as it potentially confers drug selectivity with limited off-target effects. In particular, an FBXO3 inhibitor, such as the compounds disclosed herein, occupies an ApaG domain cavity of the FBXO3 protein.

An FBXO3-ApaG motif 3D structure was generated from homology model based on crystal structure of ApaG protein (2F1E.pdb) from *Xanthomonas axonopodis* pv. *Citri*. In certain embodiments, an FBXO3 inhibitor contacts and interacts with amino acid residues Y308, N335, E341, T368 and S370 that are located in the ApaG domain cavity. For example, an FBXO3 inhibitor may couple with the amino acid residues via hydrogen bonding, Van der Waals forces, salt-bridge formation, or covalent bonding. In certain embodiments, an FBXO3 inhibitor includes at least one amine group that forms a salt-bridge within 4 angstroms from glutamic acid 341 carboxyl group, and at least one nitrogen- or oxygen-containing group that forms a hydrogen bond within 3 angstroms from threonine 368 hydroxyl group, serine 370 hydroxyl group, asparagine 335 carboxamide group, and tyrosine 308 hydroxyl group.

In certain embodiments, the subject is in need of, or has been recognized as being in need of, treatment with an FBXO3 inhibitor. The subject may be selected as being amenable to treatment with an FBXO3 inhibitor. For example, the subject may be in need of an anti-inflammatory agent that inhibits inflammation caused by at least two different pro-inflammatory cytokines.

Currently, synthetic glucocorticoids are used in the treatment of a wide range of inflammatory disorders; its primary anti-inflammatory mechanism involves blocking lipocortin 1 synthesis, followed by suppressing phospholipase A2 action and modulating levels of two classes of pro-inflammatory products such as prostaglandins and leukotrienes. However, glucocorticoids have many other target proteins in vivo; thus, its non-specificity with off-target effects may cause a variety of adverse effects such as hyperglycemia, insulin resistance, diabetes mellitus, osteoporosis, cataracts, anxiety, depression, colitis, hypertension, ictus, erectile dysfunction, hypogonadism, hypothyroidism, amenorrhea, and retinopathy. Based on the novel, selective, mechanism of FBXO3 inhibitors, the compounds disclosed herein may provide better toxicity profile with potent in vivo activity.

The compounds disclosed herein regulate inflammation through a relatively new E3 ligase subunit, FBXO3, and its downstream target, TRAFs proteins. Thus, it represents a totally distinct mechanism of action from glucocorticoids and existing anti-inflammatories such as nonsteroidal anti-inflammatory agents (NSAIDs).

Pharmaceutical Compositions

Another aspect of the disclosure includes pharmaceutical compositions prepared for administration to a subject and which include a therapeutically effective amount of one or more of the compounds disclosed herein. In certain embodiments, the pharmaceutical compositions are useful for treating inflammation, particularly cytokine-induced inflammation. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl) methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., J. Pharm. Sci. 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., J. Pharmacy Pharmacol. 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon-aprolactone-CO-glycolic acid), poly (beta-hydroxy butyric acid), poly(alkyl-2-cyanoacrylate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, dog, sheep, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

The compounds disclosed herein may also be co-administered with an additional therapeutic agent. Such agents include, but are not limited to, another anti-inflammatory agent, an antimicrobial agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the compounds described herein. In one example, this component is formulated in a pharmaceutical preparation for delivery to a subject. The compound is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

Results

FBXL2 Targets TRAFs for Polyubiquitination.

It was presently observed that ectopic expression of FBXL2 in murine lung epithelia (MLE) specifically reduces TRAF1-6 protein levels and phosphorylation levels of the p105 subunit in the NF-κb pathway (FIG. 1A). FBXL2 was also conditionally expressed in MLE cells using a doxycycline-inducible plasmid resulting in TRAF protein degradation in a time-dependent manner (FIG. 1B). In coimmunoprecipitation experiments where cells were lysed and subjected to FBXL2 immunoprecipitation (i.p.), all TRAF proteins were detected in FBXL2 immunoprecipitates by immunoblotting (FIG. 1C). The results suggest that FBXL2 interacts with TRAFs in cells. Importantly, inclusion of purified SCFFBXL2 with the full complement of E1 and E2 enzymes plus ubiquitin was sufficient to generate polyubiquitinated TRAF species in vitro (FIG. 1D). Lastly, ectopic expression of FBXL2 decreased TRAF protein half-life (FIG. 1E) but not their mRNA levels (data not shown).

FBXL2 is Polyubiquitinated at the Lysine 201 Site.

Figure 2A:
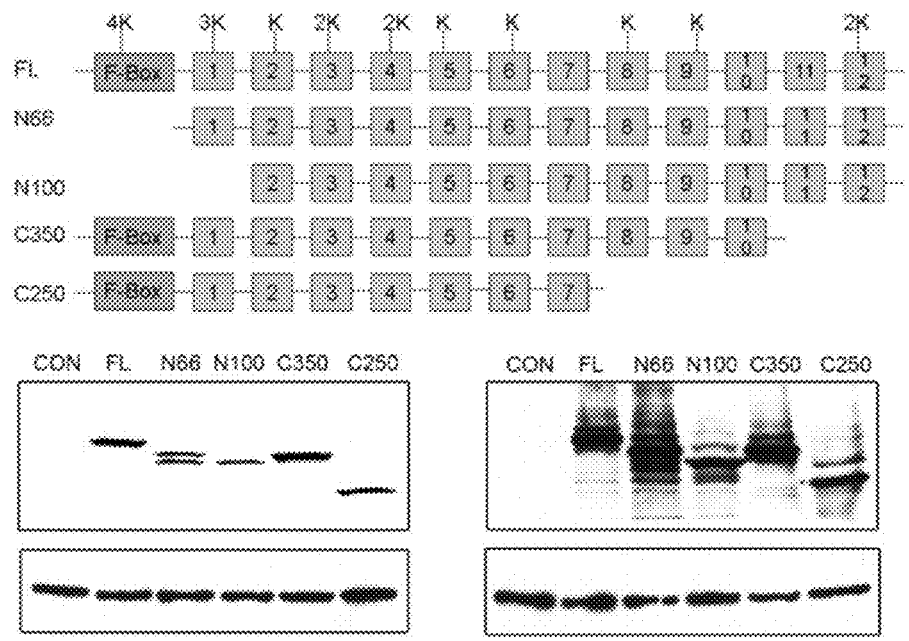
Figure 2B:
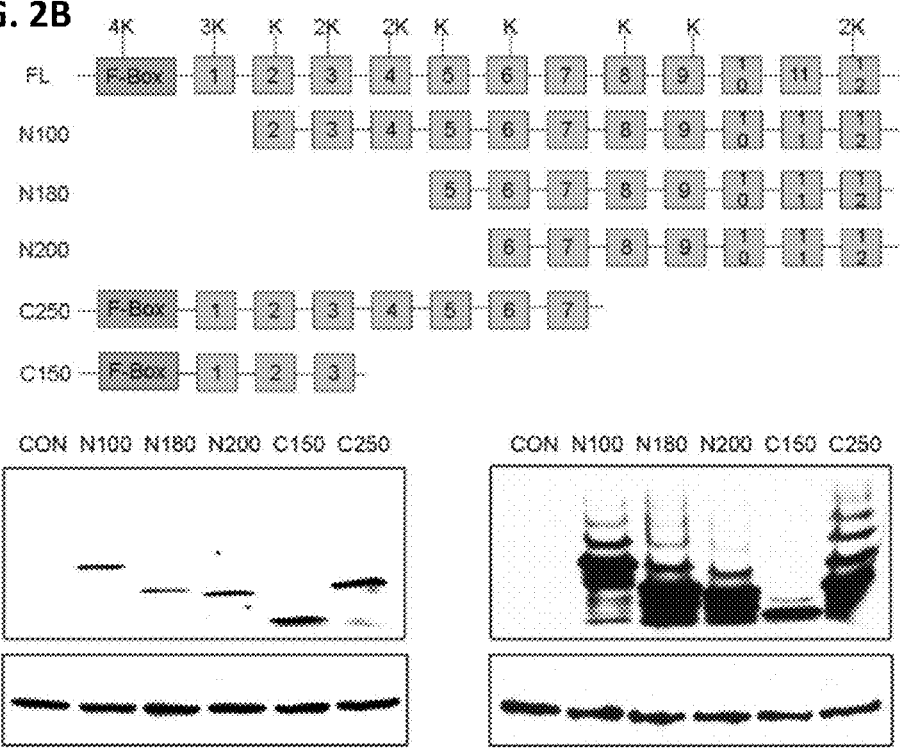

Since FBXL2 is an important regulator of TRAFs, the mechanism involved in FBXL2 stability and degradation was investigated. First, several FBXL2 deletion mutants lacking specific lysine ubiquitin acceptor sites (FIG. 2A, top map) were constructed, and their vulnerability to polyubiquitination was tested by exposing cells to the 26S proteasome inhibitor MG132. Full length (FL) and four other FBXL2 deletion mutants all displayed significant accumulation of high molecular weight ubiquitination products (FIG. 2A, bottom, right). Further deletional analysis suggested that a FBXL2-C150 mutant is resistant to ubiquitination as no significant accumulation of slower migrating species were detected (FIG. 2B, bottom right). There are two potential ubiquitination sites within 50 residues between FBXL2 C150 and C200. Site-directed mutagenesis of these sites and expression of a plasmid encoding these mutants resulted in significant resistance of the FBXL2 K201R mutant to the 26S proteasome inhibitor MG132 (FIG. 2C). The stability of this mutant was also tested in a half-life ($t_{1/2}$) study, which indicated significantly prolonged $t_{1/2}$ compared to WT FBXL2 (2.5 h, FIG. 2D).

Figure 3D:
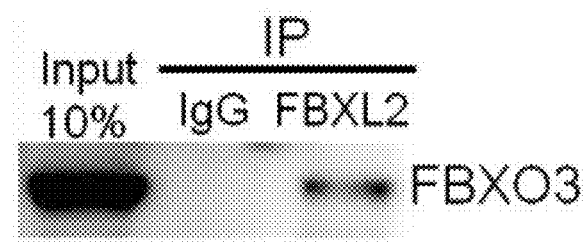

FBXL2 is phosphorylated and targeted by the SCF E3 ligase subunit FBXO3 at residue T404. SCF-based E3 ligases target phosphoproteins. Database analysis indicates many potential phosphorylation sites within the FBXL2 (FIG. 3A, GPS2.1 software prediction). To confirm that FBXL2 is phosphoprotein, cells were lysed and subjected to FBXL2 i.p., and using phospho-threonine antibodies we were able to detect a band which migrates at the predicted size of FBXL2 (FIG. 3B). In order to identify the potential kinase that targets FBXL2 for phosphorylation, we performed co-immunoprecipitation (co-i.p.) experiments. MLE cells were lysed and subjected to FBXL2 i.p.; interestingly, out of seven kinases tested, GSK3J was the only protein detected in the FBXL2 immunoprecipitates (FIG. 3C). Because FBXL2 is a phosphoprotein that might be targeted for SCF-based ubiquitination, we started an unbiased screen randomly testing F-box proteins that might mediate FBXL2 degradation. Upon overexpression of these proteins, only FBXO3 was able to decrease the levels of immunoreactive FBXL2 (data not shown). FBXO3 belongs to a large group of F-box proteins lacking a distinct C-terminal motif, thus deemed F-box domain only proteins (FBXOs). Only one study showed that FBXO3 increases ubiquitination of p300, and its authenticity as an SCF subunit and its substrates remain largely unknown. To confirm the specificity of FBXO3 targeting FBXL2, co-i.p. experiments were performed where FBXO3 was detected in the FBXL2 immunoprecipitates (FIG. 3D).

Figure 3E:
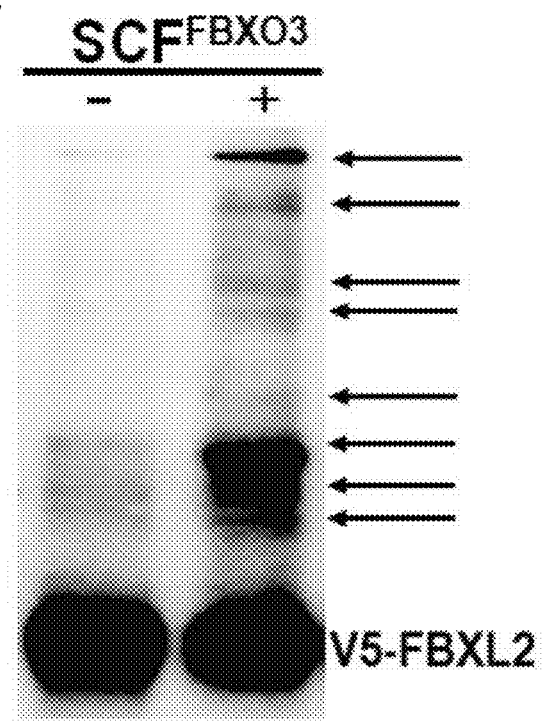
Figure 3F:
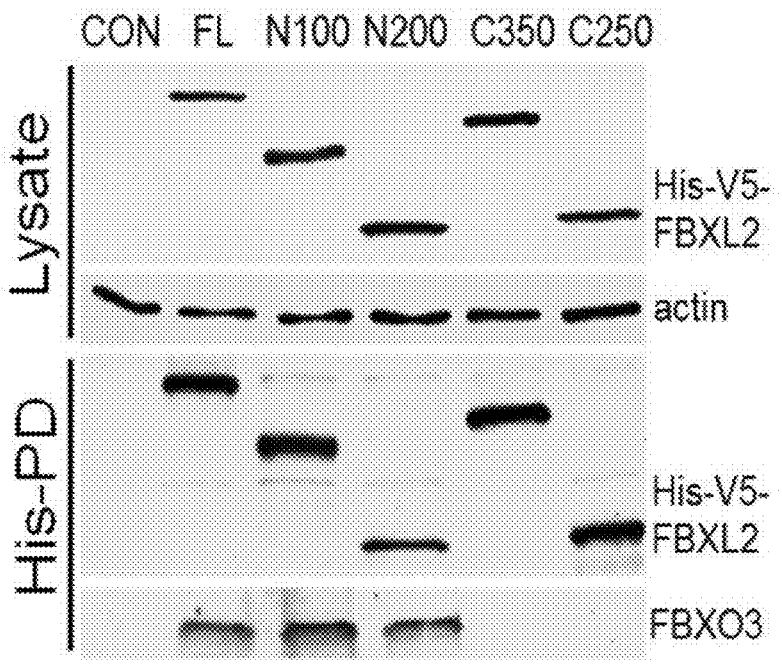
Figure 3G:
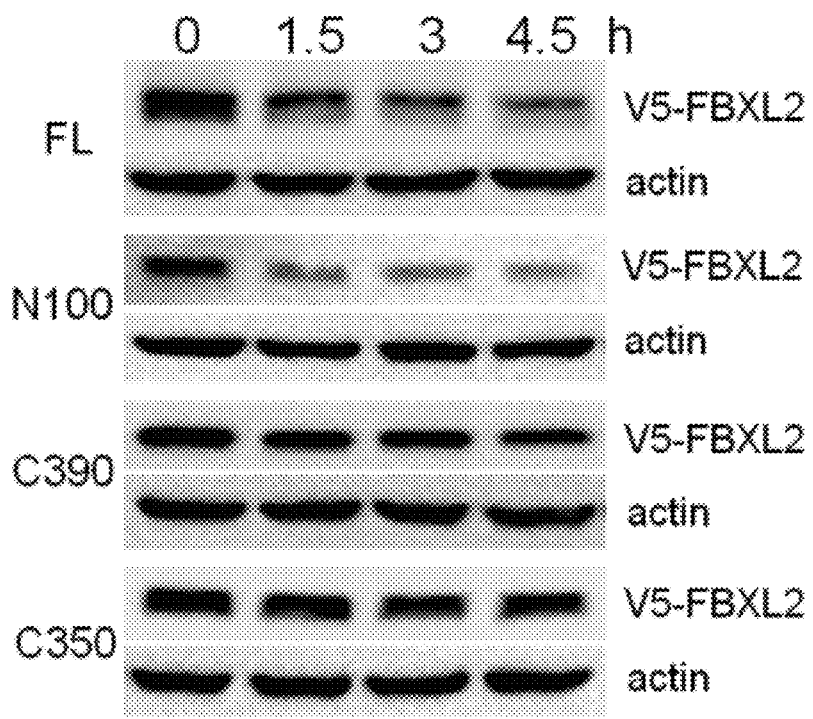
Figures 3H, 3I:
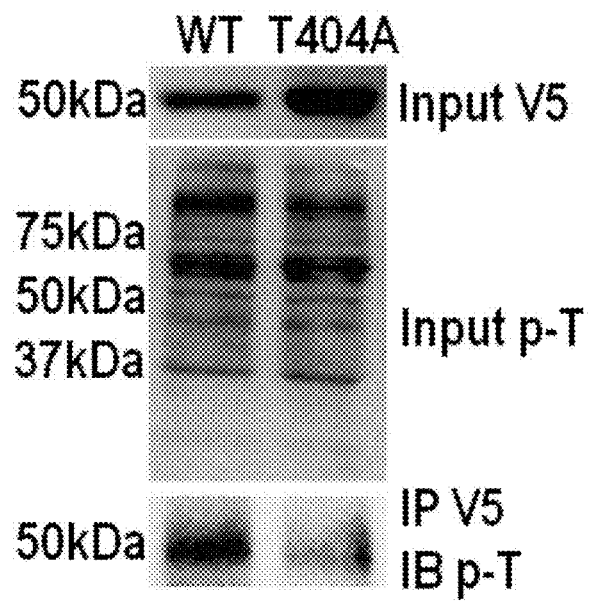
Figure 3J:
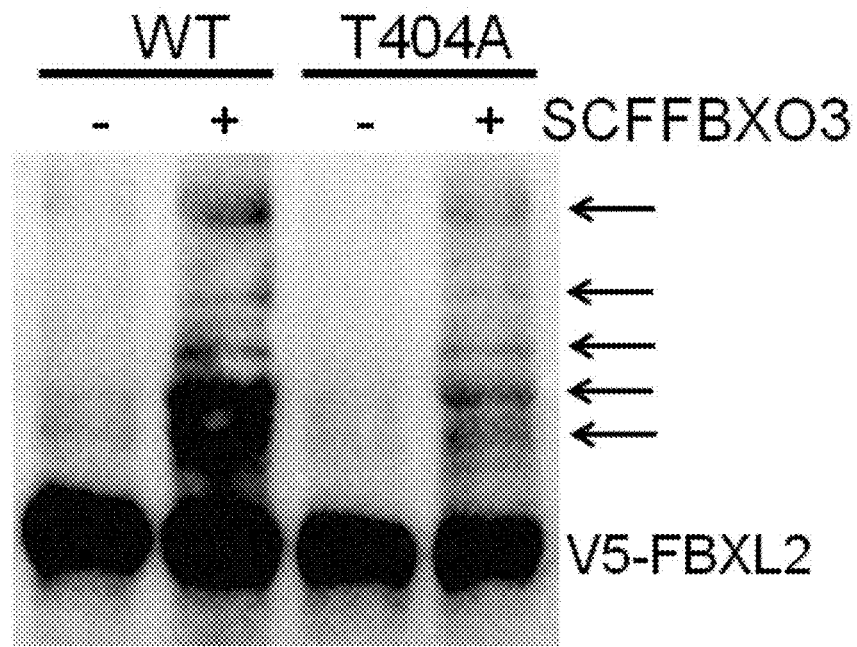
Figure 3K:
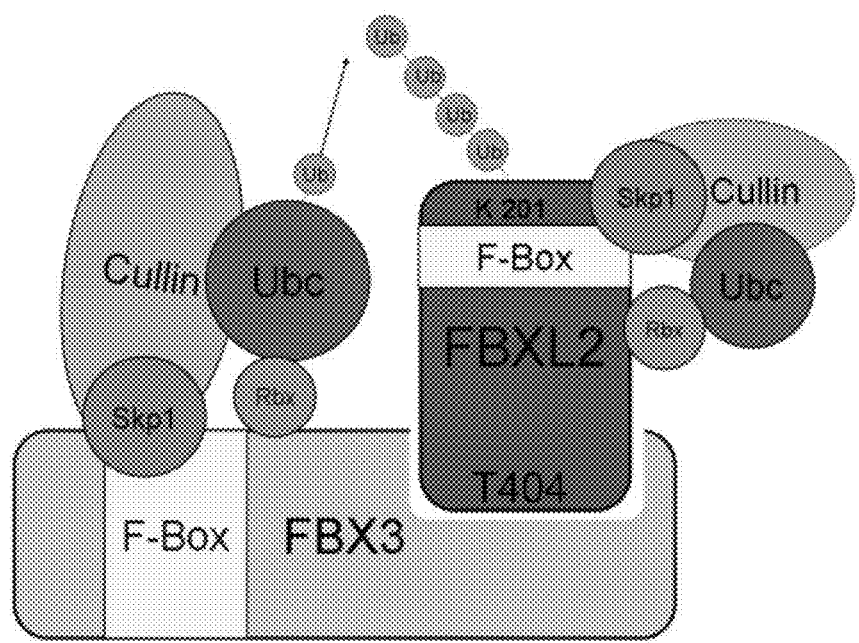

Further, the SCFFBXO3 complex was able to induce polyubiquitination of FBXL2 (FIG. 3E). Using the FBXL2 deletion mutants described in FIG. 2A, preliminary mapping studies transfecting cells with histagged FBXL2 constructs followed by his-pull down were performed. Our results indicate that FBXO3 docks at the C-terminus (residues 350-423) of FBXL2 (FIG. 3F). To confirm that this region is important for FBXL2 stability, wild-type (WT) FBXL2 and several FBXL2 C-terminal deletion mutants were tested for stability (FIG. 3G). Interestingly, a FBXL2 C390 deletion mutant exhibited significantly prolonged $t_{1/2}$ compared WT FBXL2, suggesting that residues 390-423 are important for its stability. Within this region, there is a consensus GSK3J phosphorylation site (FIG. 3H, GPS2.1 software prediction). To confirm that T404 is the authentic FBXL2 phosphorylation site, cells transfected with either a WT FBXL2 or FBXL2 T404A mutant were lysed and subjected to V5-FBXL2 i.p., and immunoblotted using phospho-threonine antibodies where a significant decrease in FBXL2 T404A protein phosphorylation levels was detected (FIG. 3I). Interestingly, this site also serves as a targeting motif for FBXO3 interaction, as FBXL2 T404A exhibits significant resistance to SCFFBXO3 using in vitro ubiquitination assays (FIG. 3J). In summary, FBXO3 targets a T404 phosphorylation site within FBXL2, which in turn recruits the SCF complex to polyubiquitinate FBXL2 at a K201 site (FIG. 3K).

FBXO3 Contains a Natural Occurring Mutation at V220.

Figure 4A:
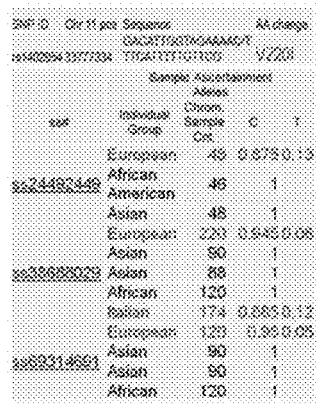
Figure 4B:
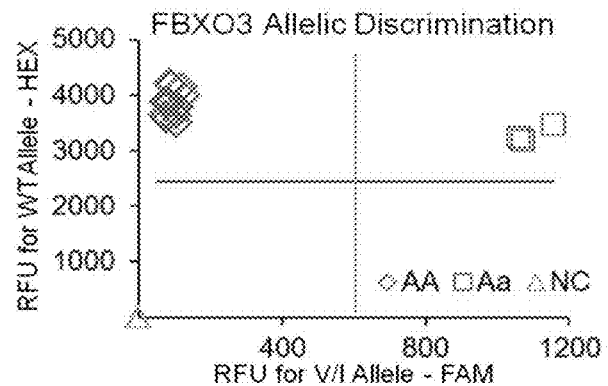
Figure 4C:
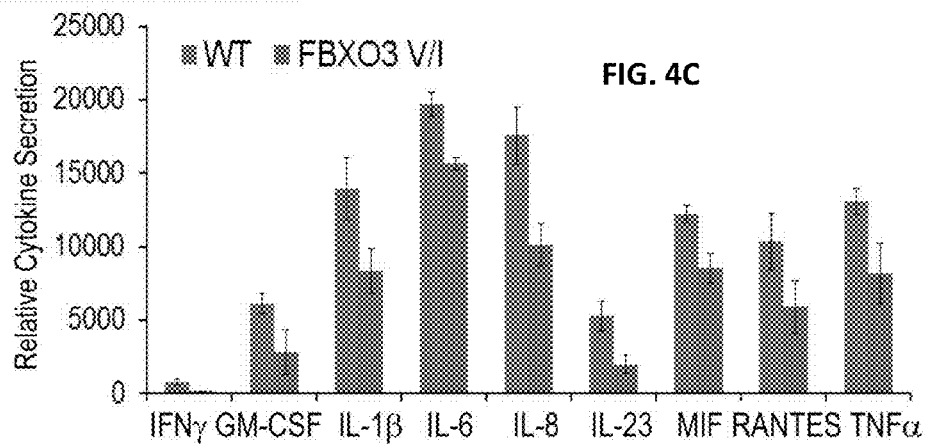

Interestingly, the SNP database analysis indicates a natural occurring mutation within FBXO3 (Val220Ile) with a very high mutation frequency of ~10%, though only in Caucasians (FIG. 4A). To confirm that V220I is a relevant FBXO3 mutation in human cells, PBMC samples from twenty healthy Caucasian volunteers (commercially available through Sanguine Life Science) were analyzed. Genomic DNA was first extracted from PBMC cells followed by SNP genotyping through TaqMan® SNP probe using real-time PCR. Three Caucasian PBMC samples harboring FBXO3V220I mutations were identified (FIG. 4B). These PBMC cells containing this FBXO3 mutation were tested using in vitro assays for cytokine release. Wt or mutant PMBC cells were first cultured in RPMI medium supplemented with 10% FBS, cells were then treated with 2 ug/ml LPS for 24 h, and cytokines released in the medium were assayed using a human cytokine array. Interestingly, in the LPS induced model, the induction of several major pro-inflammatory cytokines were significantly suppressed in PBMC cells harboring the FBXO3V220I mutation compared to WT PBMC cells (FIG. 4C); thus, the FBXO3V220I mutation might confer a reduced pro-inflammatory phenotype in subjects with infection or other autoimmune diseases.

The nature of the FBXO3 V220I mutation was subsequently tested. Compared to WT FBXO3, the SCF-FBXO3V220I complex displayed markedly reduced ability to polyubiquitinate FBXL2 with most of the substrate intact (FIG. 4D, below, lighter exposure). FBXO3 function in U937 monocytes was then studied, which adopt the morphology and many characteristics of mature macrophages. Preliminary data show that FBXL2 ubiquitinates and mediates degradation of TRAF proteins thereby potentially reducing cytokine expression. Thus, by eliminating FBXL2 in cells, it is hypothesized that FBXO3 should be able to up-regulate TRAF protein levels and stimulate cytokine expression. Indeed, consistent with this hypothesis, FBXO3 overexpression was able to decrease FBXL2 protein levels, yet significantly increase all six TRAF protein member levels (FIG. 4E). However, overexpression of FBXO3V220I only resulted in basal or no increase in several TRAF proteins. U937 cell cytokine release upon LPS challenge was further monitored. Cells were first transfected with LacZ, FBXO3, or FBXO3V220I for 24 h before exposure to LPS at 100 ng/ml for an additional 24 h. Thirty six cytokines levels were measured using a human cytokine array. Interestingly, it was observed that FBXO3 significantly up-regulates most of the cytokines released in combination with LPS challenge (FIG. 4F, red); however, FBXO3V220I expression did not dramatically alter cytokine release compared to the LacZ control (FIG. 4F). These novel results are the first linking two F-box proteins to the innate immune response and suggest that FBXO3V220I is a loss-of function mutation of FBXO3. The results raise the possibility that individuals that harbor this naturally occurring hypomorphic mutation might exhibit a blunted response to infection or other auto-immune diseases.

FBXO3V220I is a Loss-of-Function Mutation of FBXO3 In Vivo.

Figure 5G:
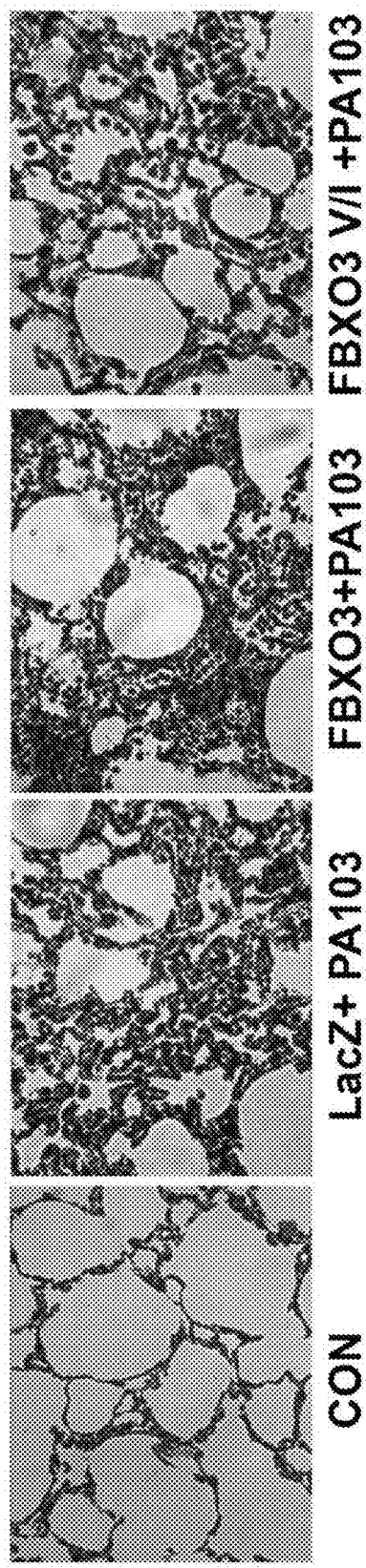
Figure 5H:
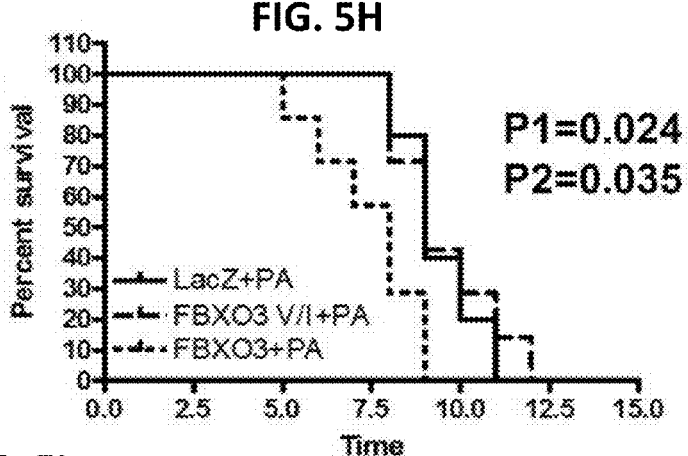
Figure 5I:
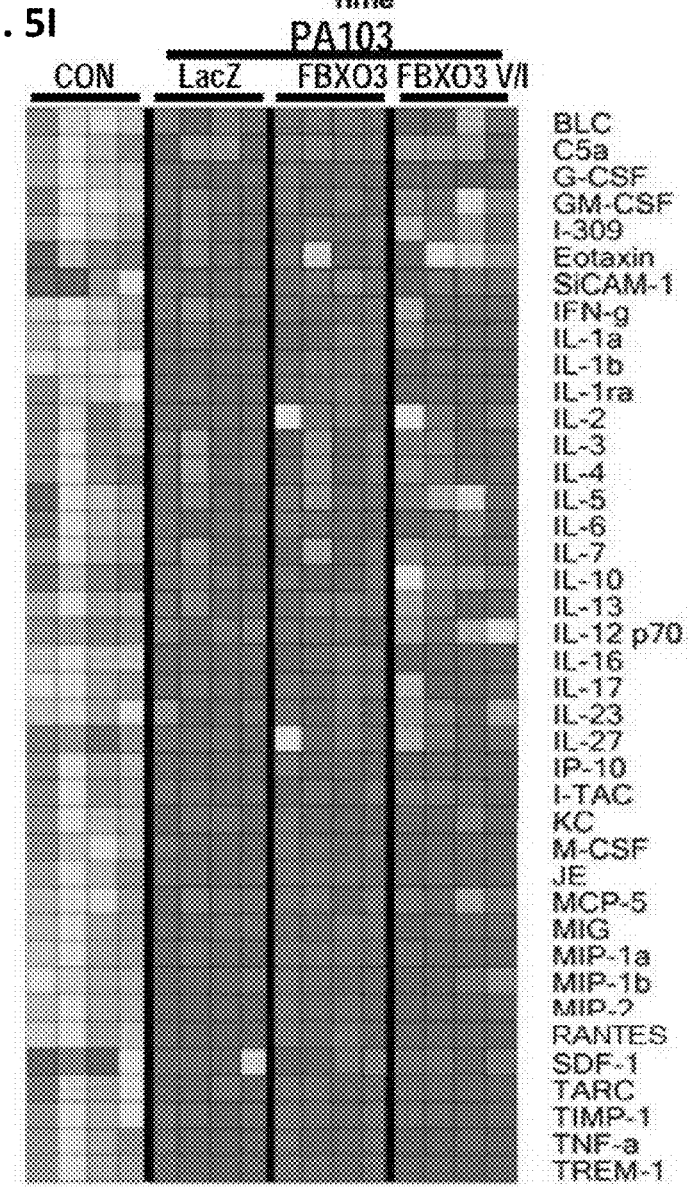

To extend the above observations in vivo, mice were infected with an empty lentivirus, or lentivirus encoding either FBXO3 or FBXO3V220I for 120 h ($10^7$ CFU/mouse, i.t.). Mice were then challenged with *P. aeruginosa* (strain PA103, $10^4$ CFU/mouse, i.t.) for an additional 24 h. Mice were then monitored with FlexiVent to measure lung mechanics and euthanized to collect lavage fluid. Wt FBXO3 expression, but not FBXO3V220I, significantly augmented PA103 induced lung injury. Specifically, FBXO3 overexpression significantly increased lung resistance and elastance, and decreased compliance (FIG. 5A-D). FBXO3 overexpression significantly increased lavage protein concentration, lavage cell counts and cell infiltrates (FIG. 5E-G). FBXO3 also decreased survival of PA103 infected mice ($10^5$ CFU/mouse, FIG. 5H). FBXO3 overexpression also significantly increased lavage cytokine levels in PA103 infected mice compared to empty vector with or without PA103 (FIG. 5I). These effects were not observed using the FBXO3V220I mutant. These in vivo studies suggest again that FBXO3V220I is a loss-of-function mutant of FBXO3.

Figure 6G:
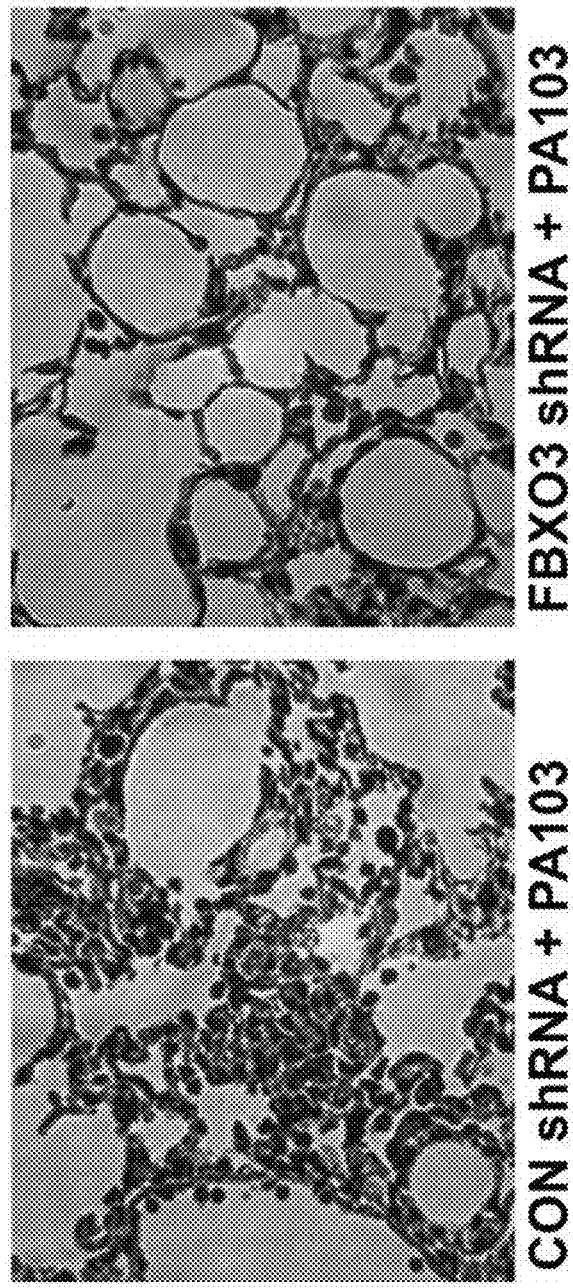
Figure 6I:
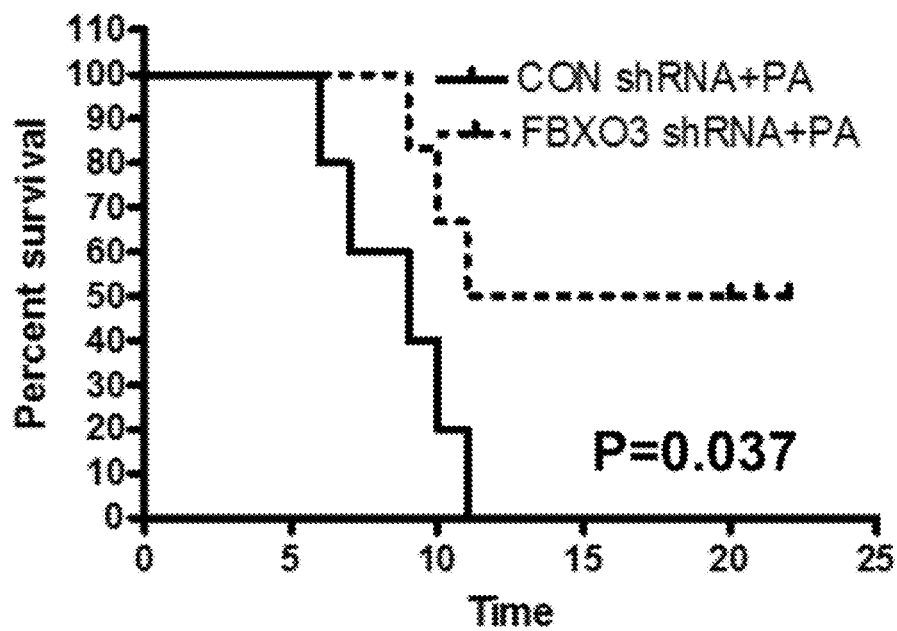

FBXO3 knockdown ameliorated *pseudomonas* induced lung injury in vivo. To confirm the role of FBXO3 in pneumonia, in vivo knockdown studies were pursued where mice were infected with lentivirus encoding empty shRNA or FBXO3 shRNA for 120 h ($10^7$ PFU/mouse, i.t). Mice were then challenged with PA103 ($10^4$ CFU/mouse, i.t.) for an additional 24 h. Interestingly, FBXO3 knockdown significantly ameliorated adverse effects of PA103 on lung mechanics. Specifically, FBXO3 knockdown increased compliance, decreased lung resistance and elastance (FIG. 6A-D). FBXO3 knockdown also decreased lavage protein concentration, lavage cell counts and cell infiltrates (FIG. 6E-G). Further, FBXO3 knockdown significantly decreased lavage cytokine levels in PA103 infected mice (FIG. 6H) and increased their survival ($10^5$ CFU/mouse, FIG. 6I). These in vivo studies suggest that FBXO3 plays an important role in regulating the cytokine storm and may serve as a potential pharmaceutical target. Thus, to investigate the potential application of FBXO3 inhibition in pneumonia, the FBXO3 structure was analyzed and small molecule inhibitors were screened.

FBXO3 ApaG Domain Structural Analysis and Inhibitor Screening.

Figure 7A:
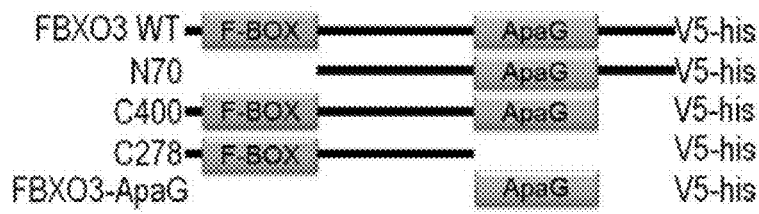
FIGS. 7A-7F. FBXO3 structural analysis reveals a bacterial-like ApaG domain FIG. 7A. Several deletion mutants of FBXO3 were designed and cloned into a pcDNA3.1D/V5-HIS vector.
Figure 7B:
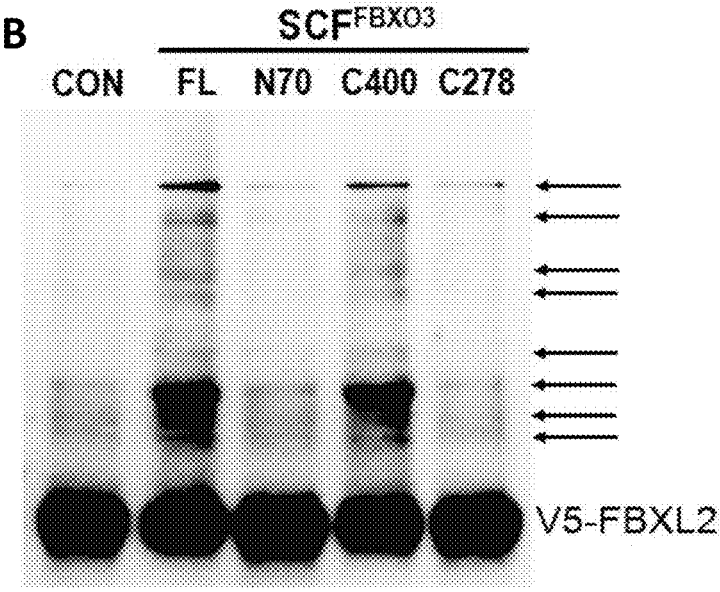
Figure 7C:
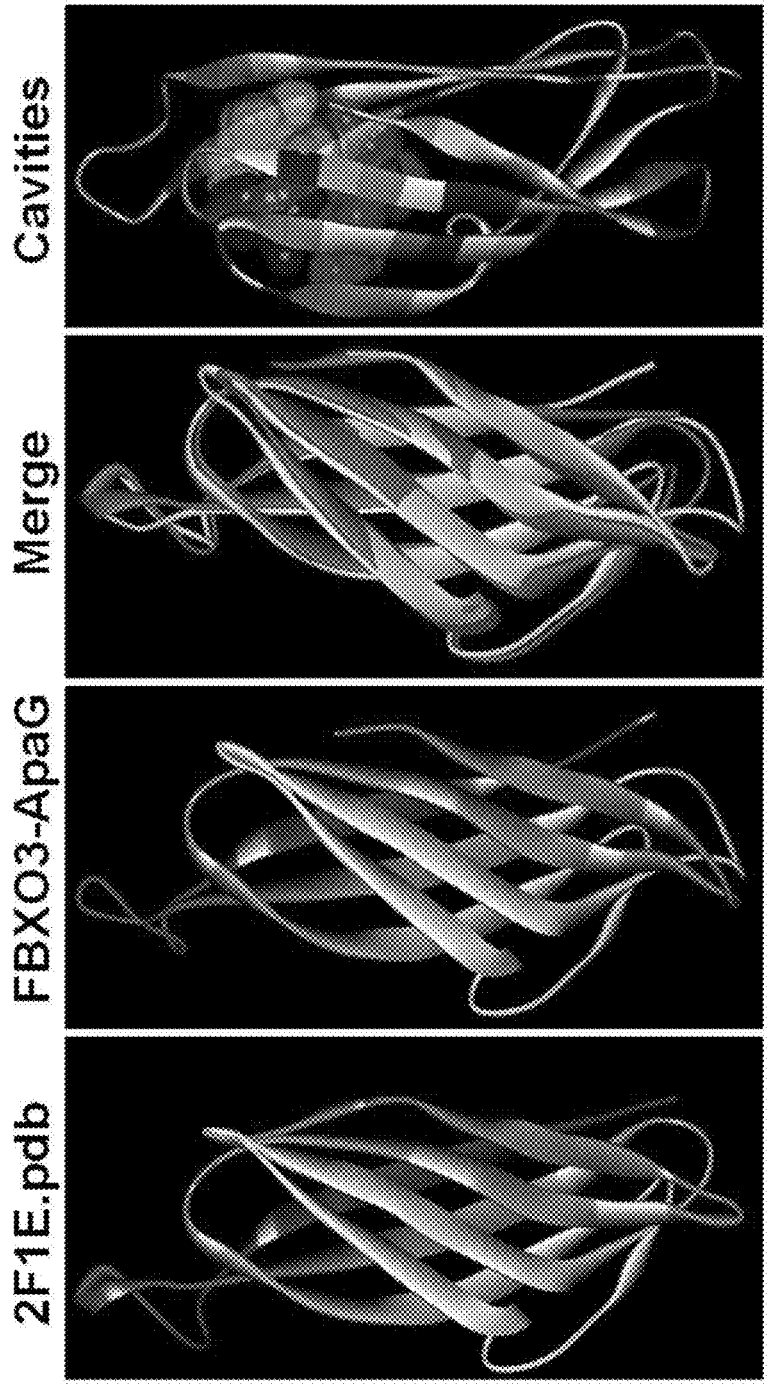
Figure 7F:
Figure 7E:
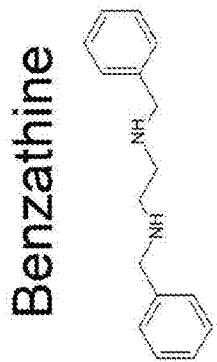
Figure 7D:

FBXO3 harbors a very unique domain termed ApaG within its carboxyl-terminus. The ApaG domain was first identified in bacteria, containing ~125 amino acids, which comprises a core. However, the function of the ApaG protein in bacteria is unknown. In *Salmonella typhimurium*, the ApaG domain protein, CorD, is involved in Co2+ resistance and Mg2+ efflux. Structural analysis from different ApaG proteins shows a fold of several beta-sheets. Since F-box proteins often utilize their carboxyl-terminal domain to target their substrates, it was hypothesized that the FBXO3 ApaG domain is involved in FBXO3 substrate recognition. To test this, a series of FBXO3 deletion mutants was designed where the ApaG domain was deleted (FIG. 7A). In vitro transcription and translation (TnT) were used to synthesize these mutants and which were then tested in the in vitro ubiquitination assay using FBXL2 as the substrate. Interestingly, FBXO3-C278, which lacks the ApaG domain, lost the ability to induce polyubiquitination of FBXL2 (FIG. 7B); FBXO3-N70, which lacks the $NH_2$-terminal F-box domain required to interact with the SCF complex, served as a negative control. These experiments suggest that the FBXO3-ApaG domain is required for FBXL2 targeting. Next it was hypothesized that inhibition of the ApaG domain disrupts FBXO3 targeting to its substrate, FBXL2. A structural homology analysis was performed identifying that the FBXO3-ApaG domain is highly conserved (FIG. 7C). Using molecular docking analysis and scored-ranking operations on the predicted FBXO3-ApaG 3-D structure model, potential ligands were assessed that might fit the ApaG domain cavities (FIG. 7D). The docking experiments were carried out by using LigandFit and CDock from Discovery studio 2.5. A library containing 6507 approved or experimental drugs were first used to screen potential ligands for FBXO3-ApaG. In this model, $Glu^{64}$ within the ApaG domain (123AA) is potentially important for interacting inhibitors. Based on the docking and best-fit analysis of suitable ligands, benzathine was selected as a backbone to develop a series of new biomolecules to test their abilities to inhibit cytokine secretion by interacting within the ApaG binding pocket (FIG. 7E-F).

FBXO3 Inhibitors Preparation and Docking Analysis.

Figure 8A:
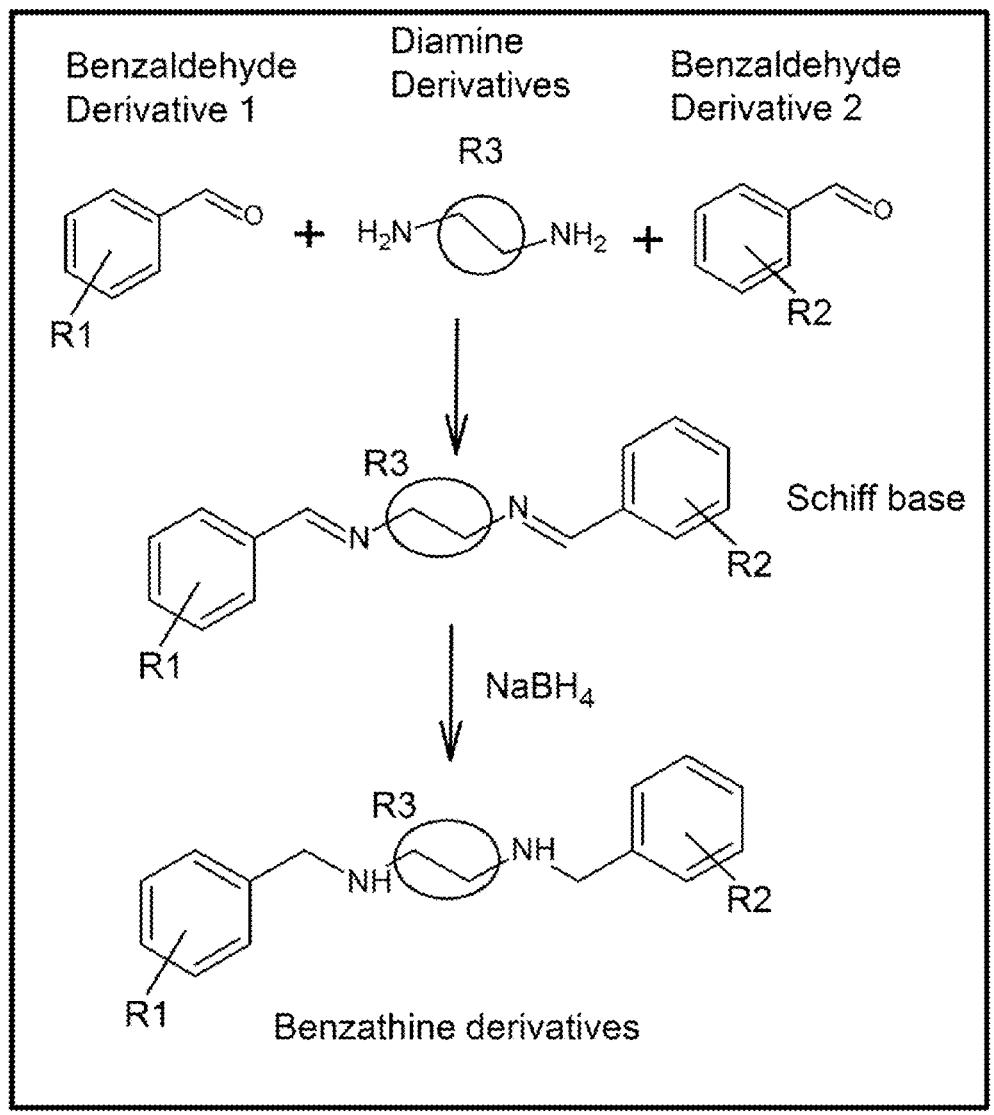
FIGS. 8A-8D. Generation of FBXO3 inhibitors and docking analysis.

The target benzathine analogs were prepared from benzaldehyde derivatives and diamine derivatives such as ethylenediamine (FIG. 8A). In general, the relevant benzaldehyde derivatives (0.02 mol) were added to a solution of ethylenediamine (0.01 mol, ~700 ul) in anhydrous ethanol (20 ml). The resulting solution was refluxed and stirred for 60 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitates of benzathine analogs were collected, washed with water and dried, followed by recrystallization from ethyl acetate.

Figure 8B:
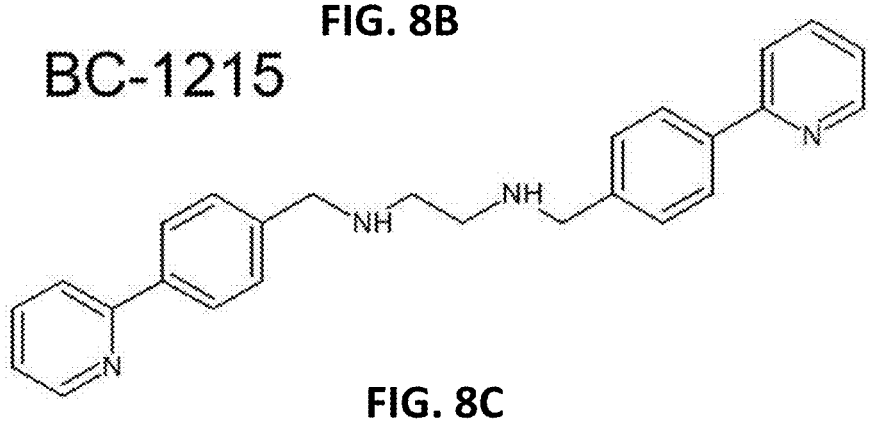
Figure 8C:
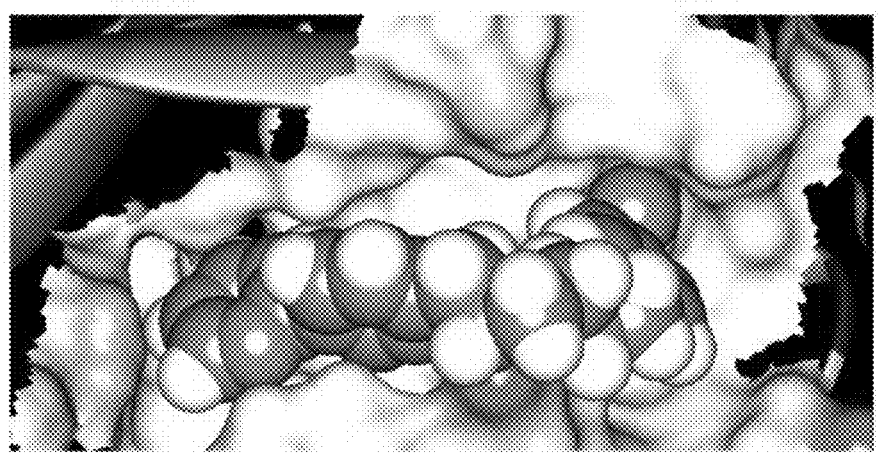
Figure 8D:
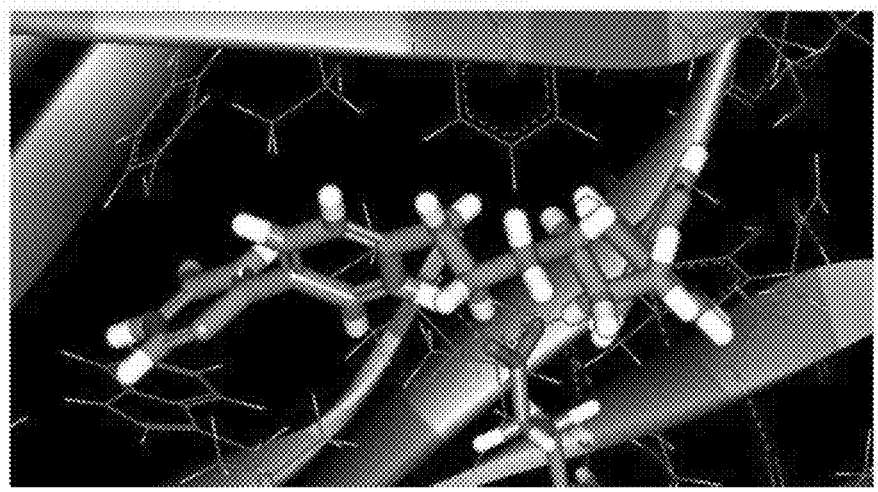

As shown in table 1, forty new compounds were constructed and tested for their IC50, LD50 and therapeutic index (TI). Briefly, compounds were added to human PBMC cells at different concentrations that were exposed to LPS and cytokine secretion was monitored by ELISA to determine the IC50. Compounds were also added to U937 monocytes at different concentrations, and cells were stained with trypan blue to determine the LD50. Several compounds (BC-1207, BC-1215, BC-1241, BC-1250 and BC-1261) scored high in docking studies with the FBXO3-ApaG domain and exhibited high IC50 and low LD50 in vitro. Importantly, several new small molecules, termed BC-1215 and BC-1261, exhibited optimal interactions with FBXO-ApaG based on structural and docking analysis as shown in FIG. 8B-D. These specific agents exhibited remarkable therapeutic indices that warranted further biological testing. Several functional studies were undertaken to assess anti-inflammatory effects focusing on BC-1215.

BC-215 Profoundly Inhibits a Broad Spectrum of Cytokines.

PBMC cells were treated with 2 ug/ml LPS for 16 hrs along with BC-1215 at 10 ug/ml. Cytokine release was monitored by a human cytokine array (R&D systems). The results from FIG. 9 indicate remarkable ability of BC-1215 to significantly suppress the majority of the TH1 panel cytokines including G-CSF, GM-CSF, GROα, 1-309, IL1-α, IL1-β, IL1rα, IL-6, IL-12, IL-23, MIP-1α, MIP-1β and TNFα. These cytokines are tightly linked to the pathogenesis of many pro-inflammatory diseases, some of which have led to the use of blocking cytokine antibodies to reduce disease severity. For example: GM-CSF drives inflammation in rheumatoid arthritis (RA), and currently, GM-CSF blocking antibodies (MOR103) have been tested in Phase 1b/2a trial in patients suffering from RA.

Canakinumab, a human IL1-β blocking antibody has been approved for treatment of cryopyrin-associated periodic syndromes and is being tested in Phase 1 trials for chronic obstructive pulmonary disease. IL-6 has been linked to many auto-immune diseases and cancer, and recently IL-6 blocking antibody was tested in Phase 2 trials in patients suffering from non-small cell lung cancer. IL-12 and IL-23 are linked with autoimmunity; Ustekinumab (commercial name Stelara) is a human monoclonal antibody against IL-12 and IL-23, which has been approved to treat moderate to severe plaque psoriasis. TNFα, a critical TH1 cytokine, also promotes the inflammatory response, and is etiologically linked to many autoimmune disorders such as RA, inflammatory bowel disease, psoriasis, and refractory asthma. Several TNFα blocking antibodies such as infliximab (Remicade), adalimumab (Humira) or certolizumab (Cimzia) have been approved to treat these autoimmune disorders. However, many of the above approaches have a limited spectrum of bioactivity as they target a single cytokine and are directed against a host protein. The data disclosed herein are significant in that they suggest that this new family of F box protein E3 ligase antagonists (e.g. BC-1215) described herein may be more efficacious in inflammatory disorders as they are panreactive to several pro-inflammatory molecules and they target a unique bacterial-like molecular signature in host cells. These unique properties of F box protein E3 ligase antagonists will confer greater anti-inflammatory activities and yet have limited off-target effects.

BC-1215 Inhibits FBXO3 and Decreases TRAF Protein Levels.

To establish a mechanistic link between infection and cytokine release, PBMC cells were treated with LPS, and downstream signaling proteins were assayed by immunoblotting. It was found that LPS increases FBXO3 protein levels, decreases FBXL2 protein levels, and increases TRAF protein levels (FIG. 10A). Thus, pro-inflammatory signaling by endotoxin actions might be mediated though FBXO3 protein. BC-1215 was first tested in in vitro ubiquitination assays using FBXL2 as substrate. BC-1215 was able to inhibit FBXO3 catalyzed FBXL2 polyubiquitination (FIG. 10B). MLE cells were also treated with BC-1215 at different concentrations for 16 h. Cells were collected and assayed for protein immunoblotting. As shown in FIG. 10C, BC-1215 increased FBXL2 protein levels in a dose dependent manner, in turn decreasing TRAF protein levels. Other known FBXL2 substrates including cyclin D2, cyclin D3, and CCTalpha served as positive controls. We also observed that BC-1215 did not significantly alter cell cycle progression of Hela cells in the therapeutic doses (FIG. 10D). BC-1215 did not alter COX-2 activity compared to the positive control, DuP-697 (FIG. 10E). These latter results strongly suggest that BC-1215 and related agents mechanistically represent a new genus of anti-inflammatories that exerts activities independent of mechanisms used by nonsteroidal anti-inflammatory drugs (NSAIDs) which act as COX-2 inhibitors. Based on the novel mechanism of action of BC-1215, the effectiveness of this agent was tested in several different inflammation models in mice.

BC-1215 Potently Inhibits Cytokine Release in a LPS Induced Septic Shock Model.

Compound BC-1215 was first solubilized in water using acetic acid in a 1:2 molar ratio; the stock solution of BC-1215 was 5 mg/ml. 500 ug, 100 ug, 20 ug, 4 ug and 0.8 ug of BC-1215 was administered to mice though an intraperitoneal (IP) injection. 10 min later, mice were given 100 ug of LPS (*E. coli*) through an IP injection. 90 min later, mice were euthanized; blood was collected and tested for IL1-β, IL-6 and TNFα, cytokine assays. The results from FIG. 11 indicate that $IC50_{IL-1\beta}=1$ mg/kg, $IC50_{IL-6}=2.5$ mg/kg, $IC50_{TNF\alpha}=1.2$ mg/kg. These IC50s are considered very low considering that the predicted mouse oral LD50 dose for BC-1215 is 1.135 g/kg; thus BC-1215 exerts bioactivity well below a predicted toxic dose in vivo.

BC-1215 Inhibits Cytokine Release in a Cecal Ligation and Puncture (CLP) Sepsis Model.

Compound BC-1215 was first solubilized as above. 100 ug of BC-1215 was administered to mice though an IP injection. 30 min later, CLP was performed. 6 h later, mice were euthanized; blood was collected and tested for IL1-β, IL-6 and TNFα cytokines. As shown in FIG. 12, CLP treated mice had significantly increased cytokine release compared to sham treated mice. However, BC-1215 was able to significantly attenuate CLP-induced secretion of all three circulating pro-inflammatory cytokines in mice.

BC-1215 Reduces Lung Injury in *Pseudomonas* Induced Pneumonia.

To test the F box inhibitor BC-1215 in pneumonia, 100 ug of BC-1215 was administered to mice though an IP injection, mice were then challenged with *Pseudomonas aeruginosa* strain PA103 ($10^4$ CFU/mouse, i.t.) for an additional 18 h. Interestingly, BC-1215 significantly ameliorated adverse effects of PA103 on lung mechanics. Specifically, BC-1215 increased compliance, decreased lung resistance, and reduced elastance (FIG. 13A-D). BC-1215 also decreased lavage protein concentration, lavage cell counts and cell infiltrates (FIG. 13E, F, G). Further, BC-1215 also significantly decreased lavage pro-inflammatory cytokine levels in PA103 infected mice (FIG. 13H).

BC-1215 Ameliorates H1N1 Influenza Induced Lung Injury In Vivo.

To further test BC-1215 in pneumonia, mice were challenged with H1N1 ($10^5$ PFU/mouse, i.t.) and observed for 9 d. For BC-1215 treatment, a stock solution (5 mg/ml) was added to drinking water (containing 2% sucrose) to the final concentration of 30 ug/ml. Lung mechanics was measured at day 5. Specifically, BC-1215 increased compliance, decreased lung resistance and reduced elastance (FIG. 14A-C) in mice infected with H1N1. Further, BC-1215 significantly increased their survival with H1N1 pneumonia (FIG. 14D). BC-1215 also remarkably decreased lavage protein concentration, lavage cell counts (FIG. 14E, F), lung edema and cell infiltrates (FIG. 14G, H).

BC-1215 Reduces TPA Induced Ear Edema.

Topical application of BC-1215 as an anti-inflammatory agent was tested in a model of 12-O-tetradecanoylphorbol-13-acetate (TPA) induced ear edema (Bralley et. al., J Inflamm (LOnd), 2008. 5:p. 1). Briefly, 20 µl of an ethanol solution of BC-1215 was applied to ears of mice at 8, 40, and 200 ug/ear for 30 min after TPA administration (2 µg/ear). Comparisons included equal volumes of ethanol (vehicle control). 18 h after TPA administration, mice were euthanized; the thickness of the ear was measured using a micrometer. Ear punch biopsies were also taken immediately, weighed, and graphed. As shown in FIG. 15A, ear edema was observed in the TPA-treated animals at 18 h after its treatment. However, BC-1215 was able to significantly resolve edema. As shown in FIG. 15B-C, BC-1215 significantly reduced ear thickness and ear weight in a dose dependent manner compared to the vehicle control. These studies demonstrate for the first time that the FBXO3 inhibitor BC-1215, by inhibiting development of edema, may have topical applicability and thus may have a role in dermatologic inflammatory disorders.

BC-1215 Ameliorates Carrageenan Induced Paw Edema.

BC-1215 also was tested in a mouse paw edema model to confirm its anti-inflammatory activity. Mice received subplantar administration of 25 ul of saline or 25 ul of carrageenan (1% in saline) (Posadas et al., Br J Pharmacol, 2004. 142(2):p. 331-8), followed by an IP injection of 200 ug of BC-1215 daily. 48 h later, mice were euthanized; the thickness and volume of the paw was measured. As shown in FIG. 16A, paw edema was observed in carrageenan-treated animals at 48 h. However, BC-1215 was able to significantly suppress this affect. As shown in FIG. 16B-C, BC-1215 significantly reduced paw thickness and edema compared to vehicle control. Thus, the FBXO3 inhibitor BC-1215 suppresses inflammation in a nonpulmonary model of edema involving the extremities.

BC-1215 Ameliorates DSS Induced Colitis.

BC-1215 was also tested in a mouse colitis model to confirm its anti-inflammatory activity. Briefly, C57BL6 mice were fed with water containing 3.5% dextran sulfate sodium (DSS) for up to five days. Mice were treated with either vehicle or 200 ug of BC-1215 daily (via IP injection). Mice were then euthanized; the length of colons was measured. As shown in FIG. 17A, a significant decrease in colon length was observed with mice treated with DSS, consistent with colonic inflammation. However, mice treated with BC-1215 shown no significant decrease in colon length compared to control. Colonic tissue cytokine levels were analyzed. As shown in FIG. 17B-C, mice treated with BC-1215 showed a remarkable reduction in IL13 and TNFα levels in colon tissues compared to vehicle treated mice. Further, BC-1215 significantly reduced colonic tissue injury in DSS treated mice (FIG. 17D). Thus, the FBXO3 inhibitor BC-1215 suppresses inflammation in chemical induced colitis model in mice.

In summary, disclosed herein is the first evidence in any system that inflammation is mediated in part, by a novel pathway whereby a previously unrecognized E3 ligase component, FBXO3, triggers ubiquitination and degradation of another E3 ligase subunit, FBXL2, thereby increasing levels of TRAF proteins. In essence, FBXL2 appears to be a feedback inhibitor of inflammation. As TRAFs are critical molecular inputs to NF-κB-driven cytokine gene expression, abrogation of FBXO3 is able to prevent induction of TRAF proteins and suppress cytokine production (FIG. 18). Hence, based on the unique molecular structure of FBXO3 as the centerpiece of this discovery, a new phylum of F box ubiquitin-E3 ligase based ApaG small molecule inhibitors was generated that profoundly exert anti-inflammatory activity in human cells and in complementary small animal models of tissue inflammation and injury.

BC-1215 Inhibits *S. aureus* Proliferation.

BC-1215 was tested in antibiotic sensitivity tests using Mueller-Hinton agar as shown in FIG. 19. Briefly, 6 mm filter papers containing different amounts of BC-1215 or gentamicin antibiotic (positive control) were added on the Mueller-Hinton agar pre-exposed to *Staphylococcus aureus*. The plates were incubated at 37 degrees for 24 h. Zone sizes were measured and marked by a red circle indicating positive results. The data here suggests that BC-1215 may inhibit bacterial growth through the bacterial ApaG protein.

FBXO3 Inhibitors Synthesis

General procedure for synthesis of BC-1202. 4-(Benzyl-Oxy)Benzaldehyde (0.01 mol, 2.12 g) were added to a solution of ethylenediamine (0.005 mol, ~350 ul) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1202 were collected, washed with water and dried, followed by recrystallization from ethyl acetate.

General procedure for synthesis of BC-1203. 4-(Dimethylamino)Benzaldehyde (0.01 mol, 1.49 g) were added to a solution of ethylenediamine (0.005 mol, ~350 ul) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1203 were collected, washed with water and dried, followed by recrystallization from ethyl acetate.

General procedure for synthesis of BC-1204. 4-Methoxybenzaldehyde (0.02 mol, 2.72 g) were added to a solution of ethylenediamine (0.01 mol, ~700 ul) in anhydrous ethanol (40 ml). The resulting solution was heated and stirred for 40 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The product BC-1204 was then extracted with EtOAC and the organic layer washed with water, dried over Na2SO4 and concentrated under vacuum.

General procedure for synthesis of BC-1205. 4-(4-Morpholinyl)benzaldehyde (0.01 mol, 1.91 g) were added to a solution of ethylenediamine (0.005 mol, ~350 ul) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1205 were collected, washed with water and dried, followed by recrystallization from ethyl acetate.

General procedure for synthesis of BC-1206. 4-(1-Pyrrolidino)-benzaldehyde (0.01 mol, 1.75 g) were added to a solution of ethylenediamine (0.005 mol, ~350 ul) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1206 were collected, washed with water and dried, followed by recrystallization from ethyl acetate.

General procedure for synthesis of BC-1207. 4-(1H-Imidazol-1-yl)benzaldehyde (0.01 mol, 1.72 g) were added to a solution of ethylenediamine (0.005 mol, ~350 ul) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1207 were collected, washed with water and dried, followed by recrystallization from ethyl acetate.

General procedure for synthesis of BC-1208. 4-Acetylbenzaldehyde (0.01 mol, 1.48 g) were added to a solution of ethylenediamine (0.005 mol, ~350 ul) in anhydrous ethanol (20 ml). The resulting solution was refluxed and stirred for 60 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1208 were collected, washed with water and dried, followed by recrystallization from ethyl acetate.

General procedure for synthesis of BC-1209. 2-Hydroxybenzaldehyde (0.01 mol, 1.22 g) were added to a solution of ethylenediamine (0.005 mol, ~350 ul) in anhydrous ethanol (20 ml). The resulting solution was heated and stirred for 10 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1209 were collected, washed with water and dried, followed by recrystallization from ethyl acetate.

General procedure for synthesis of BC-1210. 4-Hydroxybenzaldehyde (0.01 mol, 1.22 g) were added to a solution of ethylenediamine (0.005 mol, ~350 ul) in anhydrous ethanol (20 ml). The resulting solution was heated and stirred for 10 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1210 were collected, washed with water and dried, followed by recrystallization from ethanol.

General procedure for synthesis of BC-211. 4-Trifluoromethoxy)benzaldehyde (0.01 mol. 1.9 g) were added to a solution of ethylenediamine (0.005 mol, ~350 ul) in anhydrous ethanol (20 ml). The resulting solution was heated and stirred for 60 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The product BC-1211 was then extracted with EtOAC and the organic layer washed with water, dried over Na2SO4 and concentrated under vacuum.

General procedure for synthesis of BC-1212. 4-(Dimethylamino)benzaldehyde (0.01 mol, 1.49 g) were added to a solution of 1,2-Phenylenediamine (0.005 mol, 0.54 g) in anhydrous ethanol (20 ml). The resulting solution was heated and stirred for 30 min. The reaction was cooled down until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1212 were collected, washed with water and dried, followed by recrystallization from ethyl acetate.

General procedure for synthesis of BC-1213. 4-(Dimethylamino)benzaldehyde (0.01 mol, 1.49 g) were added to a solution of (+/−)-trans-1,2-Diaminocyclohexane (0.005 mol, 0.57 g) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1213 were collected, washed with water and dried, followed by recrystallization from ethyl acetate.

General procedure for synthesis of BC-1214. 4-(1-Piperidinyl)benzaldehyde (0.01 mol, 1.89 g) were added to a solution of ethylenediamine (0.005 mol, ~350 ul) in anhydrous ethanol (20 ml). The resulting solution was refluxed and stirred for 30 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1214 were collected, washed with water and dried, followed by recrystallization from ethyl acetate.

General procedure for synthesis of BC-1215. 4-(2-Pyridinyl)benzaldehyde (0.01 mol, 1.83 g) were added to a solution of ethylenediamine (0.005 mol, ~350 ul) in anhydrous ethanol (20 ml). The resulting solution was heated and stirred for 30 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1215 were collected, washed with water and dried, followed by recrystallization from ethyl acetate.

General procedure for synthesis of BC-216. 3,4,5-Trimethoxybenzaldehyde (0.01 mol, 1.96 g) were added to a solution of ethylenediamine (0.005 mol, ~350 ul) in anhydrous ethanol (20 ml). The resulting solution was heated and stirred for 30 min. The reaction was cooled down until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1216 were collected, washed with water and dried, followed by recrystallization from ethyl acetate.

General procedure for synthesis of BC-1217. 4-(1-Pyrrolidino)-benzaldehyde (0.01 mol, 1.75 g) were added to a solution of (+/−)-trans-1,2-Diaminocyclohexane (0.005 mol, 0.57 g) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1217 were collected, washed with water and dried, followed by recrystallization from ethyl acetate.

General procedure for synthesis of BC-1218. 4-(1-Piperidinyl)benzaldehyde (0.01 mol, 1.89 g) were added to a solution of (+/−)-trans-1,2-Diaminocyclohexane (0.005 mol, 0.57 g) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1218 were collected, washed with water and dried, followed by recrystallization from ethyl acetate.

General procedure for synthesis of BC-1220. 4-(4-Morpholinyl)benzaldehyde (0.01 mol, 1.91 g) were added to a solution of (+/−)-trans-1,2-Diaminocyclohexane (0.005 mol, 0.57 g) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1220 were collected, washed with water and dried, followed by recrystallization from ethyl acetate.

General procedure for synthesis of BC-1232. 4-(1-Pyrrolidino)-benzaldehyde (0.01 mol, 1.75 g) were added to a solution of 1,2-Phenylenediamine (0.005 mol, 0.54 g) in anhydrous ethanol (20 ml). The resulting solution was refluxed and stirred for 30 min. The reaction was cooled down until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1232 were collected, washed with water and dried, followed by recrystallization from ethyl acetate.

General procedure for synthesis of BC-1233. 4-(1-Pyrrolidino)-benzaldehyde (0.01 mol, 1.75 g) were added to a solution of (1S,2S)-(+)-1,2-Diaminocyclohexane (0.005 mol, 0.57 g) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1233 were collected, washed with water and dried, followed by recrystallization from ethyl acetate.

General procedure for synthesis of BC-1234. 4-(1-Pyrrolidino)-benzaldehyde (0.01 mol, 1.75 g) were added to a solution of 1,4-Diaminobutane (0.005 mol, 0.44 g) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1234 were collected, washed with water and dried, followed by recrystallization from ethyl acetate.

General procedure for synthesis of BC-1239. 4-(1-Pyrrolidino)-benzaldehyde (0.01 mol, 1.75 g) were added to a solution of 1,3-Diaminopropane (0.005 mol, 0.37 g) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1239 were collected, washed with water and dried, followed by recrystallization from ethyl acetate.

General procedure for synthesis of BC-1241. 4-(2-Pyridinyl)benzaldehyde (0.005 mol, 0.92 g), 4-fluorobenzaldehyde (0.005 mol, 0.62 g) were added to a solution of ethylenediamine (0.005 mol, ~350 ul) in anhydrous ethanol (20 ml). The resulting solution was refluxed and stirred for 60 min. The reaction was cooled down until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1241 were collected, washed with water and dried, followed by recrystallization from ethyl acetate.

General procedure for synthesis of BC-i 248. 4-(2-Pyridinyl)benzaldehyde (0.005 mol, 0.92 g), 2-Pyridinecarboxaldehyde (0.005 mol, 0.53 g) were added to a solution of ethylenediamine (0.005 mol, ~350 ul) in anhydrous ethanol (20 ml). The resulting solution was refluxed and stirred for 60 min. The reaction was cooled down until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1248 were collected, washed with water and dried, followed by recrystallization from ethyl acetate.

General procedure for synthesis of BC-1250. 4-(1H-Pyrazol-1-yl)benzaldehyde (0.004 mol, 0.7 g) were added to a solution of ethylenediamine (0.002 mol, ~140 ul) in anhydrous ethanol (10 ml). The resulting solution was heated and stirred for 20 min until the precipitation of the relevant Schiff base. The Schiff bases were filtered off, and washed with cold ethanol. The Schiff base was then added to 15 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine. The precipitation of BC-1250 were collected, washed with water and dried, followed by recrystallization from ethyl acetate.

General procedure for synthesis of BC-1251. 5-Chloro-2-Hydroxybenzaldehyde (0.01 mol, 1.56 g) were added to a solution of ethylenediamine (0.005 mol, ~350 ul) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1251 were collected, washed with water and dried, followed by recrystallization from ethyl acetate.

General procedure for synthesis of BC-1252. 2-Hydroxy-4-Methoxybenzaldehyde (0.01 mol, 1.52 g) were added to a solution of ethylenediamine (0.005 mol, ~350 ul) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1252 were collected, washed with water and dried, followed by recrystallization from ethyl acetate.

General procedure for synthesis of BC-1253. 2,4-Dihydroxybenzaldehyde (0.01 mol, 1.38 g) were added to a solution of ethylenediamine (0.005 mol, ~350 ul) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1253 were collected, washed with water and dried, followed by recrystallization from ethyl acetate.

General procedure for synthesis of BC-1254. 4-(2-Pyridinyl)benzaldehyde (0.01 mol, 1.83 g) were added to a solution of 1,4-Diaminobutane (0.005 mol, 0.44 g) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1254 were collected, washed with water and dried, followed by recrystallization from ethyl acetate.

General procedure for synthesis of BC-1255. 4-(2-Pyridinyl)benzaldehyde (0.01 mol, 1.83 g) were added to a solution of 1,3-Diamino-2-Propanol (0.005 mol, 0.45 g) in anhydrous ethanol (20 ml). The resulting solution was heated and stirred for 20 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1255 were collected, washed with water and dried, followed by recrystallization from ethyl acetate.

General procedure for synthesis of BC-1256. 2-(2-hydroxyethoxy)benzaldehyde (0.01 mol, 1.66 g) were added to a solution of ethylenediamine (0.005 mol, ~350 ul) in anhydrous ethanol (20 ml). The resulting solution was heated and stirred for 40 min until the precipitation of the relevant Schiff base. The Schiff bases were filtered off, and washed with cold ethanol. The Schiff base was then added to 30 ml absolute methanol. A 10% solution of sodium borohydride (0.02 mol) was dissolved in absolute methanol and added to the Schiff base. When the dropwise addition of sodium borohydride was complete, the reaction solution was refluxed for an additional 15 min. Solvent was then removed through rotary evaporation and 40 ml cold water was added to liberate the secondary amine. The precipitation of BC-1256 were collected, washed with water and dried, followed by recrystallization from ethyl acetate.

General procedure for synthesis of BC-1257. 4-Trifluoromethoxy)Salicaldehyde (0.004 mol, 0.82 g) were added to a solution of ethylenediamine (0.002 mol, ~140 ul) in anhydrous ethanol (20 ml). The resulting solution was heated and stirred for 40 min until the precipitation of the relevant Schiff base. The Schiff bases were filtered off, and washed with cold ethanol. The Schiff base was then added to 15 ml absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine. The precipitation of BC-1257 were collected, washed with water and dried, followed by recrystallization from ethyl acetate.

General procedure for synthesis of BC-1258. 4-(1,3-Thiazol-2-yl)benzaldehyde (0.004 mol, 0.76 g) were added to a solution of ethylenediamine (0.002 mol, ~140 ul) in anhydrous ethanol (20 ml). The resulting solution was heated and stirred for 20 min until the precipitation of the relevant Schiff base. The Schiff bases were filtered off, and washed with cold ethanol. The Schiff base was then added to 15 ml absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine. The precipitation of BC-1258 were collected, washed with water and dried, followed by recrystallization from ethyl acetate.

General procedure for synthesis of BC-1259. 4-(2-Thienyl)Benzaldehyde (0.004 mol, 0.76 g) were added to a solution of ethylenediamine (0.002 mol, ~140 ul) in anhydrous ethanol (20 ml). The resulting solution was heated and stirred for 40 min until the precipitation of the relevant Schiff base. The Schiff bases were filtered off, and washed with cold ethanol. The Schiff base was then added to 15 ml absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine. The precipitation of BC-1259 were collected, washed with water and dried, followed by recrystallization from ethyl acetate.

General procedure for synthesis of BC-1260. 4-(2-furyl)benzaldehyde (0.004 mol. 0.69 g) were added to a solution of ethylenediamine (0.002 mol, ~140 ul) in anhydrous ethanol (20 ml). The resulting solution was heated and stirred for 40 min until the precipitation of the relevant Schiff base. The Schiff bases were filtered off, and washed with cold ethanol. The Schiff base was then added to 15 ml absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine. The precipitation of BC-1260 were collected, washed with water and dried, followed by recrystallization from ethyl acetate.

General procedure for synthesis of BC-1261. 4-(pyrimidin-2-yl)benzaldehyde (0.004 mol, 0.74 g) were added to a solution of ethylenediamine (0.002 mol, ~140 ul) in anhydrous ethanol (20 ml). The resulting solution was heated and stirred for 30 min until the precipitation of the relevant Schiff base. The Schiff bases were filtered off, and washed with cold ethanol. The Schiff base was then added to 15 ml absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine. The precipitation of BC-1261 were collected, washed with water and dried, followed by recrystallization from ethyl acetate.

General procedure for synthesis of BC-1262. 4-Phenylbenzaldehyde (0.004 mol, 0.73 g) were added to a solution of ethylenediamine (0.002 mol, ~140 ul) in anhydrous ethanol (20 ml). The resulting solution was heated and stirred for 20 min until the precipitation of the relevant Schiff base. The Schiff bases were filtered off, and washed with cold ethanol. The Schiff base was then added to 15 ml absolute methanol. A 10% solution of sodium borohydride (0.01 mol) was dissolved in absolute methanol and added to the Schiff base. When the dropwise addition of sodium borohydride was complete, the reaction solution was refluxed for an additional 15 min. Solvent was then removed through rotary evaporation and 20 ml cold water was added to liberate the secondary amine. The precipitation of BC-1262 were collected, washed with water and dried, followed by recrystallization from ethyl acetate.

In view of the many possible embodiments to which the principles of the disclosed invention may be applied, it should be recognized that the illustrated embodiments are only preferred examples of the invention and should not be taken as limiting the scope of the invention.

---

The invention claimed is:

1. A compound, or a pharmaceutically acceptable salt thereof, having a structure of formula II:

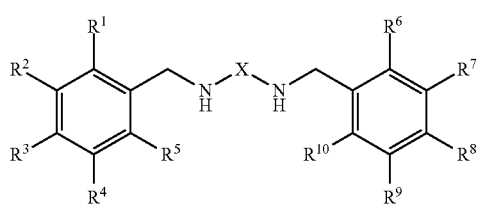

wherein X is an optionally-substituted cycloalkanediyl; and $R^1$-$R^{10}$ are each individually H, optionally-substituted alkyl, optionally-substituted alkoxy, optionally-substituted aryl, optionally-substituted cycloalkyl, optionally-substituted heterocyclic, halogen, amino, or hydroxy, provided that at least one of $R^3$ or $R^8$ is an optionally-substituted N-heterocycle selected from pyrrolyl, H-pyrrolyl, pyrrolinyl, pyrrolidinyl, oxazolyl, oxadiazolyl, isoxazolyl, furazanyl, isothiazolyl, pyrazolyl, pyrazolinyl, pyrazolidinyl, tetrazolyl, dithiazolyl, pyridyl, pyrimidinyl, pyridazinyl, pyrazinyl, piperidinyl, morpholinyl, thiomorpholinyl, piperazinyl, or triazinyl.

2. The compound of claim 1, wherein at least one of $R^3$ or $R^8$ is an optionally-substituted N-heterocycle selected from pyrrolyl, H-pyrrolyl, pyrrolinyl, pyrrolidinyl, oxazolyl, oxadiazolyl, isoxazolyl, furazanyl, isothiazolyl, pyrazolyl, pyrazolinyl, pyrazolidinyl, tetrazolyl, or dithiazolyl.

3. The compound of claim 1, wherein $R^3$ and $R^8$ are each an optionally-substituted N-heterocycle.

4. A pharmaceutical composition comprising at least one compound of claim 1, and at least one pharmaceutically acceptable additive.

5. The compound of claim 1, wherein X is cyclohexanediyl.

6. The compound of claim 2, wherein X is cyclohexanediyl.

7. The compound of claim 1, wherein $R^3$ and $R^8$ are each pyrrolidinyl.

8. The compound of claim 5, wherein $R^3$ and $R^8$ are each pyrrolidinyl.

9. A compound, or a pharmaceutically acceptable salt thereof, having a structure of formula II:

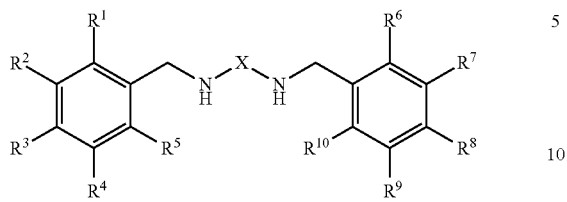

wherein X is an optionally-substituted cycloalkanediyl; and $R^1$-$R^{10}$ are each individually H, optionally-substituted alkyl, optionally-substituted alkoxy, optionally-substituted aryl, optionally-substituted cycloalkyl, optionally-substituted heterocyclic, halogen, amino, or hydroxy, provided that $R^3$ and $R^8$ are each an optionally-substituted N-heterocycle selected from pyrrolyl, H-pyrrolyl, pyrrolinyl, pyrrolidinyl, oxazolyl, oxadiazolyl, isoxazolyl, furazanyl, isothiazolyl, pyrazolyl, pyrazolinyl, pyrazolidinyl, tetrazolyl, dithiazolyl, pyridyl, pyrimidinyl, pyridazinyl, pyrazinyl, piperidinyl, morpholinyl, thiomorpholinyl, piperazinyl, or triazinyl.

10. The compound of claim 9, wherein X is cyclohexanediyl.

11. The compound of claim 10, wherein $R^3$ and $R^8$ are each pyrrolidinyl.

* * * * *